(12) United States Patent
Resnick et al.

(10) Patent No.: US 7,256,260 B1
(45) Date of Patent: Aug. 14, 2007

(54) HUMAN P53 MUTATIONS AND A GENETIC SYSTEM IN YEAST FOR FUNCTIONAL IDENTIFICATION OF HUMAN P53 MUTATIONS

(75) Inventors: Michael A. Resnick, Chapel Hill, NC (US); Alberto Inga, Chapel Hill, NC (US)

(73) Assignee: The United States of America, as represented by the Secretary, Dept. of Health and Human Services, NIH, Washington, DC (US)

(*) Notice: Subject to any disclaimer, the term of this patent is extended or adjusted under 35 U.S.C. 154(b) by 0 days.

(21) Appl. No.: 10/048,502

(22) PCT Filed: Jul. 28, 2000

(86) PCT No.: PCT/US00/20538

§ 371 (c)(1),
(2), (4) Date: Jun. 12, 2002

(87) PCT Pub. No.: WO01/09325

PCT Pub. Date: Feb. 8, 2001

Related U.S. Application Data

(60) Provisional application No. 60/146,634, filed on Jul. 30, 1999.

(51) Int. Cl.
  *C07K 14/00* (2006.01)
  *A61K 38/16* (2006.01)
  *C07H 21/04* (2006.01)
  *C12P 21/02* (2006.01)

(52) U.S. Cl. .................. 530/350; 530/358; 536/23.1; 536/23.5; 435/69.1

(58) Field of Classification Search ............. 530/300, 530/350
See application file for complete search history.

(56) References Cited

FOREIGN PATENT DOCUMENTS

| WO | WO 96/16989 | 6/1996 |
|---|---|---|
| WO | WO 97/41136 | 11/1997 |
| WO | WO 00/22115 | 4/2000 |
| WO | WO 00/68384 | 11/2000 |
| WO | WO 01/09325 A2 | 2/2001 |

OTHER PUBLICATIONS

Schwartz et al. Curr. Opin. Mol. Ther. 2:162-167, 2000.*
Schwarze et al. TICB 10: 290-295, 2000.*
Zhang, W., Development and application of adenoviral vectors for gene therapy of cancer, Cancer Gene Therapy 6(2):113-138.*
Brachmann et al. "Genetic selection of intragenic suppressor mutations that reverse the effect of common p53 cancer mutations" *EMBO J.* 17(7):1847-1859, 1998.
Bullock et al. "Quantiative analysis of residual folding and DNA binding in mutant p53 core domain: definition of mutant states for rescue in cancer therapy" *Oncogene* 19:1245-1256, 2000.
Bulliock et al. "Thermodynamic stability of wild-type and mutant p53 core domain" *Proc. Natl. Acad. Sci. USA* 94:14338-14342, 1997.
Candau et al. "Two tandem and independent sub-activation domains in the amino terminus of p53 require the adaptor complex for activity" *Oncogene* 15:807-816, 1997.
Caron de Fromentel et al. "Restoration of transcriptional activity of p53 mutants in human tumour cells by intracellular expression of anti-p53 single chain Fv fragments" *Oncogene* 18:551-557, 1999.
Chene et al. "Mutations at position 277 Modify the DNA-Binding Specificity of Human p53 in vitro" *Biochem. Biophys. Res. Commun.* 263:1-5 (1999).
Cho et al. "Crystal structures of a p53 tumor Suppressor-DNA Complex: Understanding Tumorigenic Mutations" *Science* 265:346-355, 1994.
Conseiller et al. "CTS1: A p53-derived Chimeric Tumor Suppressor Gene with Enhanced In Vitro Apoptotic Properties" *J. Clin. Invest.* 101(1):120-127, Jan. 1998.
Di Como and Prives "Human tumor-derived p53 proteins exhibit binding site selectivity and temperature sensitivity for transactivation in a yeast-based assay" *Oncogene* 16:2527-2539 (1998).
Flaman et al. "Identification of human p53 mutations with differential effects of the bax and p21 promoters using functional assays in yeast" *Oncogene* 16:1369-1372 (1998).
Flaman et al. "A simple p53 functional assay for screening cell lines, blood, and tumors" *Proc. Natl. Acad. Sci. USA* 92(9):3963-3967, Apr. 1995.
Foster et al. "Pharmacological Rescue of Mutant p53 Conformation and Function" *Science* 286:2507-2510 (1999).
Freeman et al. "Mutation of conserved domain II alters the sequence specificity of DNA binding by the p53 protein" *EMBO J.* 13(22):5393-5400, 1994.
Gagnebin et al. "Use of transcription reporters with novel p53 binding sites to target tumour cells expressing endogenuos or virally transduced p53 mutants with altered sequence-specificity" *Oncogene* 16(5):685-690, 1998.
Greenblatt et al. "Mutations in the p53 Tumor Suppresor Gene: clues to Cancer Etiology and Molecular Pathogenesis" *Cancer Res.* 54:4855-4878, 1994.

(Continued)

*Primary Examiner*—Nancy Vogel
*Assistant Examiner*—Walter Schlapkohl
(74) *Attorney, Agent, or Firm*—Needle & Rosenberg, P.C.

(57) ABSTRACT

The present invention provides isolated polypeptides of human p53 that contain mutations. These mutations can be toxic mutations, supertransactivating mutations or tox-suppressor mutations. Further provided by the invention are methods of identifying toxic, supertransactivating, weak transactivating and tox-suppressor mutations as well as methods of identifying compounds that mimic the toxic, supertransactivating and tox-suppressor mutations in human p53. Also provided are methods of inducing toxicity in a cell by administering a polypeptide comprising a supertransactivating or a toxic mutation.

2 Claims, 18 Drawing Sheets

OTHER PUBLICATIONS

Gualberto et al. "An oncogenic form of p53 confers a dominant, gain-of-function phenotype that disrupts spindle checkpoint control" *Proc. Natl. Acad. Sci. USA* 95:5156-5171, 1998.

Hainaut et al. "IARC Database of p53 gene mutations in human tumors and cell lines: updated compilation, revised formats and new visualisation tools" *Nucl. Acid Res.* 26(1):205-213, 1998.

Hernandez-Boussard et al. "IARC P53 Mutation Database: A Relational Database To Compile and Analyze p53 Mutations In Human Tumors And Cell Lines" *Hum. Mutat.* 14:1-8, 1999.

Inga et al. "N-(2-Chloroethyl)-N-Nitrosourea Tethered To Lexitropsin Induces Mirror Groove Lesion At The p53 Cdna That Are More Cytotoxic Than Mutagenic" *Cancer Res.* 59(3):689-695, 1999.

Ishioka et al. "Mutational analysis of the carboxy-terminal portion of p53 usig both yeast and mammalian cell assays in vivo" *Oncogene* 10:1485-1492, 1995.

Kelly et al. "Relationship between DNA Methylation and Mutational Patterns Induced by a Sequence Selective Minor Groove Methylating Agent" *J. Biol. Chem.* 274(26):18327-18334, 1999.

Kern et al. "Oncogenic Forms of p53 Inhibit p53-Regulated Gene Expression" 256:827-830, 1992.

Ludwig et al. "Differential Activation of Target Cellular Promoters by p53 Mutants With Impaired Apoptotic Function" *Mol. Cell. Biol.* 16(9):4952-4960, 1996.

Matsumura et al. "In vitro evolution of thermostable p53 variants" *Protein Science* 8:731-740, 1999.

Nikolova et al. "Mechanism of rescue of common p53 cancer mutations by second-site suppressor mutations" *EMBO J.* 19(3):370-378, 2000.

Saller et al. "Increased apoptosis induction by 121F mutant p53" *EMBO J.* 18(16):4424-4437, 1999.

Selivanova et al. "Reactivation of Mutant p53 through Interaction of a C-Terminal Peptide with the Core Domain" *Mol. Cell Biol.* 19(5:3395-3402, 1999.

Smith et al. "Novel p53 mutants selected in BRCA-associated tumors which dissociate transformation supression from other wild-type p53 functions" *Oncogene* 18:2451-2459, 1999.

Soussi et al. "Structural Aspects of The p53 Protein In Relation To Gene Evolution: A Second Look" *J. Mol. Biol.* 260:623-637, 1996.

Thukral et al. "Discrimination of DNA Binding Sites by Mutant p53 Proteins" *Mol. Cell. Biol.* 15(9):5196-5202, Sep. 1995.

Venot et al. "Definition of a p53 transactivation function-deficient mutant and characterization of two independent p53 transactivation subdomains" *Oncogene* 18;2405-2410, 1999.

Walker et al. "Evolutionary conservation and somatic mutation hotspot maps of p53: correlation with p53 protein structural and functional features" *Oncogene* 19:211-218, 1999.

Wieczorek et al. "Structure-based rescue of common tumor-derived p53 mutants" *Nat. Med.* 2:1143-1146, 1996.

\* cited by examiner

A                    B

HUMAN P53 MUTATIONS AND A GENETIC SYSTEM IN YEAST FOR FUNCTIONAL IDENTIFICATION OF HUMAN P53 MUTATIONS

This application is the National Stage of PCT/US00/20538, filed Jul. 28, 2000, which claims priority to U.S. provisional application Ser. No. 60/146,634 filed on Jul. 30, 1999.

BACKGROUND OF THE INVENTION

1. Field of the Invention

This invention relates to mutants of human p53 and methods of identifying mutants of p53. Specifically, the invention relates to isolated polypeptides containing human p53 mutations and to isolated nucleic acids encoding the polypeptides. The invention further relates to the methods of detecting human p53 mutations that are toxic, supertransactivating or tox-suppressor mutations as well as to the identification of compounds, agents or interactive factors, such as peptides, that mimic the toxic or the supertransactivating mutations.

2. Background Art

The most commonly inactivated gene target associated with neoplastic transformation is the tumor suppressor gene p53, a key regulator of cellular mechanisms that maintain genome integrity (Prives and Hall). Normally, cellular stresses including DNA damage, hypoxia, suboptimal growth conditions, nucleotide pool unbalance, and activated oncogenes can induce signaling cascades that converge at p53 and result in greater stability of the protein, primarily through post-translational modifications (Giacca and Kastan; Meek). In this process, the p53 half life is increased due to inhibition of the normal MDM2 associated degradation pathway (Freedman and Levine) leading to greater nuclear retention and also through a coordinated regulation of the stability of the p53 tetramer (Stommel). This produces a rapid, transient increase in nuclear levels of active p53 which causes either growth arrest or apoptosis.

The p53 mediated stress responses occur primarily through sequence-specific transcriptional activation (Prives and Hall) involving several p53 functional domains (Ko and Prives). Beginning at the N-terminus of p53, the first 43 amino acids correspond to an acidic region that contains a major transactivation domain; the region between amino acid 43 and 73 represents a second transactivation domain (Venot et al a). The next region (up to amino acid 92) is proline rich and may be involved in apoptosis induction (Venot et al b) and this is followed by a large DNA binding domain (amino acids. 100 to 300) responsible for sequence-specific DNA recognition. The remaining carboxy terminal portion codes for the nuclear localization and export signals, the oligomerization domain, and a basic regulatory region. The p53 monomer recognizes a pentameric DNA sequence (consensus 5'-RRRCW-3'), and a complete binding site consists of two closely spaced head-to-head pentamers (McLure and Lee, Cho et al.,). The transcriptionally active form of the protein is a tetramer.

Several downstream p53 activated genes (reviewed in Ko and Prives) are associated with the induction of programmed cell death (e.g. bax, IGF-BP3, PIG3), regulation of cell cycle through induction of arrest at the G1/S or G2/M checkpoints in response to DNA damage (e.g. p21, GADD45, cyclin G), and modification of p53 stability/activity (MDM2). The number of p53 controlled genes based on a search for putative p53 binding site in the human genome is quite large (>30 genes) (Tokino et al.,). The differential affinity of p53 for different binding sites provides variability in activation of downstream genes (Resnick L. e al, Wang and Prives) and explains why some p53 mutants found in tumors retain partial p53 response (Ludvig et al).

Besides transcriptional activation, p53 can affect gene expression through physical interactions with TATA binding protein and associated factors (Ko and Prives, Oren fos). Other protein-protein interactions are also likely to play an important role in mediating the p53 response. While the number of proteins interacting with p53 is high, the physiological role of these interactions in many cases is unknown (Prives and Hall). In addition p53 may play a direct role in DNA metabolism as evidenced by nuclease activity and p53 binding to recombinant-like structures (Deppert; Griffith).

Loss of p53 function is highly selected during tumor development as evidenced by p53 mutations in nearly 50% of human tumors (Grennblatt). Most alterations result from single missense mutations in the DNA binding domain that prevent or reduce DNA binding and they generally occur at the most p53 invariant residues (Walker et al). These residues usually directly contact DNA or affect the correct folding and stability of the large DNA binding domain (Cho). The strong selection for missense mutations is probably due to dominant-negative interactions with the wild type protein to generate partially inactive heterotetramers, and possibly to gain of function (Gualberto et al.,). In addition, tumor cells generally accumulate high levels of p53 mutant proteins in the nucleus. This is because there is a system for negative feedback control of p53 levels, mediated by MDM2. Loss of p53 function leads to decreased MDM2 gene transcription and accumulation of mutant p53. Functional p53 inactivation can also be achieved by sequestering the protein outside the nucleus, decreasing its stability, or by mutation in genes involved in the upstream or downstream pathways.

In the present invention, several previously identified p53 functional mutants were placed under the control of the galactose inducible GAL1 promoter, whose expression can be variably regulated. Growth inhibition was generally directly correlated with transactivation proficiency in that over-expression of wild type p53 caused severe reduction in colony size while transactivation mutants had a minor impact on growth. Truncated p53, which cannot form tetramers, caused no apparent growth delay while a mutant retaining partial activity had an impact on growth similar to normal p53. Based on this it is expected that certain p53 alleles can exhibit a stronger effect on growth than the wild type, possibly leading to inviability. This might be due to increased DNA binding affinity, altered specificity, increased stability, a shift toward the tetrameric form, or even stronger protein::protein interactions. Such alleles are expected to function more effectively than wild type p53 in mammalian cells as well. This invention has identified such a class of mutants in yeast and novel p53 alleles that cause lethality in yeast and growth suppression in a human tumor cell line. This invention further provides a screening system that can be used to isolate a variety of toxic or novel p53 alleles in yeast that are normally not detectable and these may prove useful in developing new therapeutic approaches.

The invention provides a novel screen in yeast that allows the identification of p53 alleles exhibiting increased transcriptional activation compared to the wild type. p53 alleles showing supertransactivating transcriptional activity are also provided. The invention therefore allows one skilled in the art to tailor p53 functional control for the various promoters recognized by p53 in terms of strength of induction by p53 (from no induction to supertransactivation) and for combinations of p53 responsive genes (i.e. some genes turned on, some genes turned off). This allows the skilled artisan to change the p53 responsive pathways and therefore the biological outcomes in response to environmental challenges. Supertransactivating mutants expected to represent a better choice in p53 gene therapy approaches because they can retain biological activity in the presence of highly expressed endogenous p53 tumor mutants

SUMMARY OF THE INVENTION

In one aspect the invention provides an isolated polypeptide comprising residues 117 to 127 of human p53 containing the mutation V122A, an isolated polypeptide comprising residues 272 to 282 of human p53 containing the mutation C277W, an isolated polypeptide comprising residues 272 to 282 of human p53 containing the mutation C277R, an isolated polypeptide comprising residues 333 to 343 of human p53 containing the mutation F338L, an isolated polypeptide comprising residues 153 to 163 of human p53 containing the mutation V157I, an isolated polypeptide comprising residues 70 to 80 of human p53 containing the mutation A76T, an isolated polypeptide comprising residues 145 to 155 of human p53 containing the mutation T150A, an isolated polypeptide comprising residues 115 to 125 of human p53 containing the mutation S121C, an isolated polypeptide comprising residues 90 to 100 of human p53 containing the mutation S96P, an isolated polypeptide comprising residues 110 to 120 of human p53 containing the mutation H115R, an isolated polypeptide comprising residues 120 to 130 of human p53 containing the mutation C124Y, an isolated polypeptide comprising residues 115 to 125 of human p53 containing the mutation S121F, an isolated polypeptide comprising residues 118 to 128 of human p53 containing the mutation T123A, an isolated polypeptide comprising residues 120 to 130 of human p53 containing the mutation C124F, an isolated polypeptide comprising residues 235 to 245 of human p53 containing the mutation S240N, an isolated polypeptide comprising residues 110 to 120 of human p53 containing the mutation S116T, an isolated polypeptide comprising residues 340 to 350 of human p53 containing the mutation N345S, an isolated polypeptide comprising residues 118 to 128 of human p53 containing the mutation T123S, an isolated polypeptide comprising residues 180 to 190 of human p53 containing the mutation D184G, an isolated polypeptide comprising residues 115 to 125 of human p53 containing the mutation S121F, an isolated polypeptide comprising residues 283 to 293 of human p53 containing the mutation N288K, an isolated polypeptide comprising residues 193 to 203 of human p53 containing the mutation E198V, an isolated polypeptide comprising residues 110 to 120 of human p53 containing the mutation H115R, an isolated polypeptide comprising residues 85 to 95 of human p53 containing the mutation W91R, an isolated polypeptide comprising residues 90 to 100 of human p53 containing the mutation S96P, an isolated polypeptide comprising residues 110 to 120 of human p53 containing the mutation S116T, an isolated polypeptide comprising residues 225 to 235 of human p53 containing the mutation N228K, an isolated polypeptide comprising residues 113 to 123 of human p53 containing the mutation T118A, an isolated polypeptide comprising residues 118 to 128 of human p53 containing the mutation T123P, an isolated polypeptide comprising residues 132 to 142 of human p53 containing the mutation L137R, an isolated polypeptide comprising residues 155 to 165 of human p53 containing the mutation M160T, an isolated polypeptide comprising residues 235 to 245 of human p53 containing the mutation N239Y, an isolated polypeptide comprising residues 280 to 290 of human p53 containing the mutation E285A, an isolated polypeptide comprising residues 50 to 150 of human p53 containing the mutation A76T and the mutation V122A, an isolated polypeptide comprising residues 50 to 200 of human p53 containing the mutation W91C, the mutation C124R, the mutation Q136K, and the mutation T150A, an isolated polypeptide comprising residues 100 to 200 of human p53 containing the mutation C124R, the mutation Q136K, and the mutation T150A. The invention also provides mutant polypeptides of human p53 containing combinations of the above-mentioned mutations.

The present invention further provides isolated nucleic acids encoding any of the mutant polypeptides of this invention.

Also provided by this invention is a method of detecting a supertransactivating mutation in the human p53 gene comprising: a) obtaining a yeast cell comprising a reporter gene, wherein the reporter gene is linked to a DNA sequence to which human p53 binds; b) introducing into the yeast cell a nucleic acid which encodes a human p53, the nucleic acid comprising an inducible promoter comprising GAL 1 linked to a human 53 coding sequence; c) plating the yeast cell on raffinose as a carbon source; and d) identifying colonies on plates, wherein colonies expressing wild type p53 yield red colonies and colonies expressing a supertransactivating mutation in p53 yield white or pink colonies.

The invention also provides a method of detecting a toxic mutation in the human p53 gene comprising: a) obtaining a yeast cell comprising a reporter gene, wherein the reporter gene is linked to a DNA sequence to which human p53 binds; b) introducing into the yeast cell a nucleic acid which encodes an unidentified human p53 in the cell, the nucleic acid comprising an inducible promoter comprising GAL 1 linked to a human p53 coding sequence; c) plating the yeast cell on each of glucose, raffinose or galactose; and d) identifying colonies on plates, wherein colonies expressing wild type p53 yield red colonies on glucose, red colonies on raffinose and white colonies on galactose, and wherein colonies expressing a toxic mutation in p53 yield red colonies on glucose, red colonies or white colonies or no colonies on raffinose, and no colonies on galactose.

Further provided by the present invention is a method of detecting a toxic mutation in the human p53 gene comprising: a) introducing into the yeast cell a nucleic acid which encodes an unidentified human p53 in the cell, the nucleic acid comprising an on-off promoter linked to the human p53 coding sequence; b) incubating the yeast cell in synthetic yeast medium in the presence and absence of an inducer for the promoter; and c) identifying a toxic mutant, wherein yeast expressing wildtype p53 yield growth in the presence or absence of an inducer for the promoter, and wherein yeast expressing a toxic mutation in p53 yields growth in the presence of an inducer for the promoter.

The invention also provides a method of inducing toxicity in a cell by administering to the cell a human p53 that contains a toxic mutation. Further provided by this invention is a method of inducing toxicity in a cell by administering to the cell a human p53 that contains a supertransactivating mutation.

Also provided by this invention is a method of screening for compounds that can mimic a toxic p53 mutation comprising: a) obtaining a yeast cell comprising a reporter gene, wherein the reporter gene is linked to a DNA sequence to which human p53 binds; b) introducing into the yeast cell a nucleic acid which encodes a non-toxic mutant or wildtype human p53 in the cell, the nucleic acid comprising an inducible promoter linked to a non-toxic mutant or wildtype human 53 coding sequence; c) introducing the compound to the yeast cell; d) plating the yeast cell on each of glucose, raffinose or galactose; and e) identifying a compound that mimics a toxic mutation preventing growth of colonies expressing wildtype or non-toxic mutant p53 to yield red colonies on glucose, red colonies or white colonies or no colonies on raffinose, and no colonies on galactose.

The present invention also provides a method of screening for compounds that can mimic a toxic p53 mutation comprising: a) introducing into the yeast cell a nucleic acid which encodes a non-toxic mutant or wildtype human p53 in the cell, the nucleic acid comprising an on-off promoter linked to a non-toxic mutant or wildtype human p53 coding sequence; b) introducing the compound to the yeast cell; c) incubating the yeast cell in artificial yeast medium in the presence and absence of an inducer for the promoter; and d) identifying a compound that mimics a toxic mutation, thereby preventing growth of yeast in the presence of an inducer for the promoter.

Further provided by this invention is a method of screening for a compound that can mimic a supertransactivating mutation in the human p53 gene comprising: a) obtaining a yeast cell comprising a reporter gene, wherein the reporter gene is linked to a DNA sequence to which human p53 binds; b) introducing a nucleic acid into the yeast cell which encodes a wildtype or a non-supertransactivating mutant human p53 in the cell, the nucleic acid comprising an inducible promoter linked to a nonsupertransactivating mutant or wildtype human 53 coding sequence; c) plating the yeast cell and compound on raffinose; and d) identifying a compound that mimics a supertransactivating mutation in p53 to yield white or pink colonies, wherein the compound has no effect in the absence of p53.

Since at high level of expression these p53 alleles prevent growth, raffinose was used as carbon source in order to keep the GAL1 promoter in a de-repressed but not induced state. At this low level of expression wild type p53 appears as a mutant for transactivation. By adding variable amounts of galactose, p53 expression is increased, although not in a linear fashion. Three toxic p53 mutants (# 2, 4, 5) exhibited enhanced transactivation for the p21::ADE2 reporter system: colonies are white on plates containing only raffinose. One mutant (# 2=p53-V122A) shows some enhanced transactivation also for bax::ADE2. All toxic p53 prevent growth at 0.5% or higher galactose (2% is shown). Mutant numbers correspond to Table 3.

Figure 5:
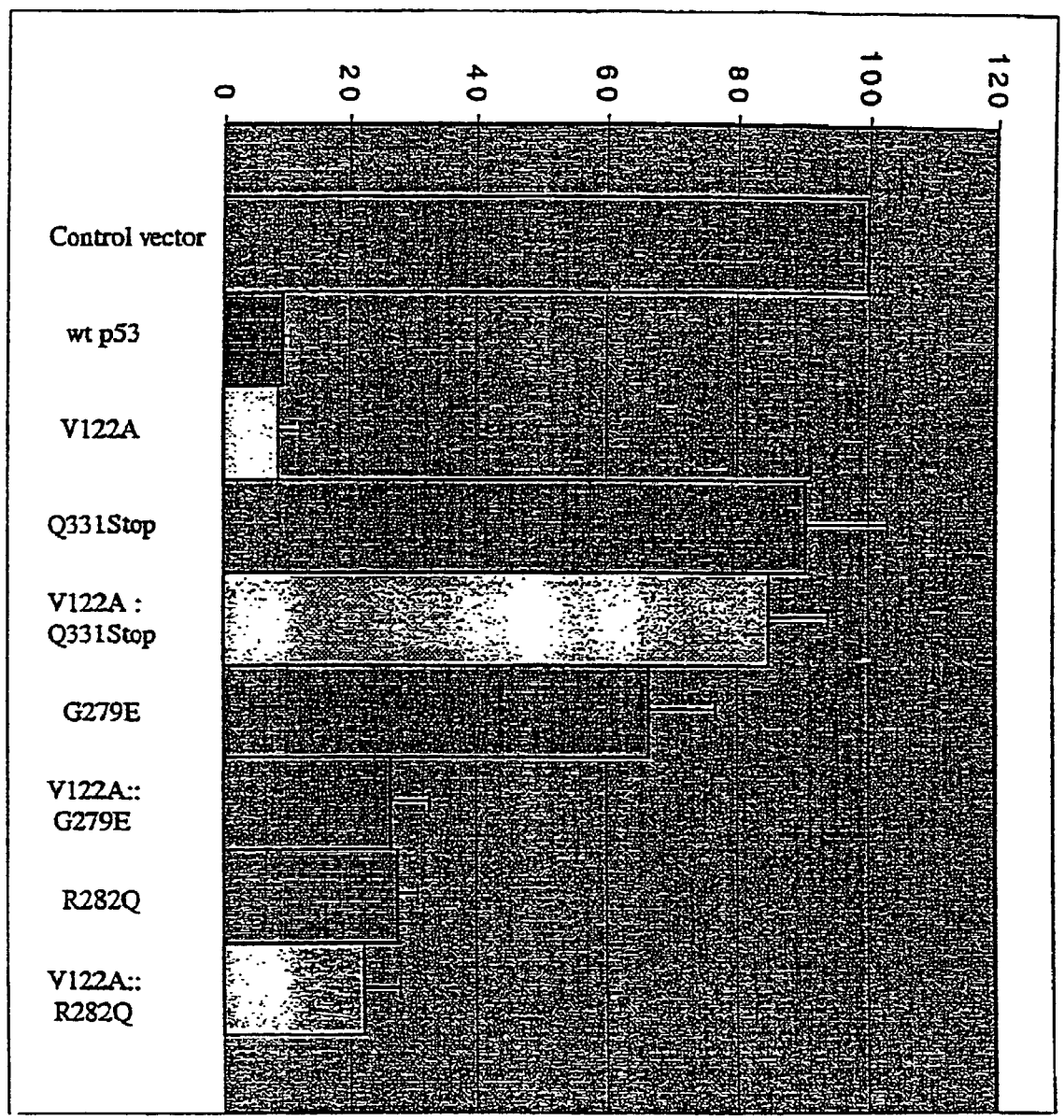

FIG. 5. Growth suppression by expressed p53 in Saos-2 cells. Saos-2 cells were transfected by lipofectin using 1.5 g of pCMV-Neo-Bam based plasmid DNA containing different p53 alleles under the control of a CMV promoter. The relative average number of colonies and standard errors for at least triplicate experiments are presented. Percentages are relative to the number of colonies obtained in transfections with the vector control.

Figure 6:
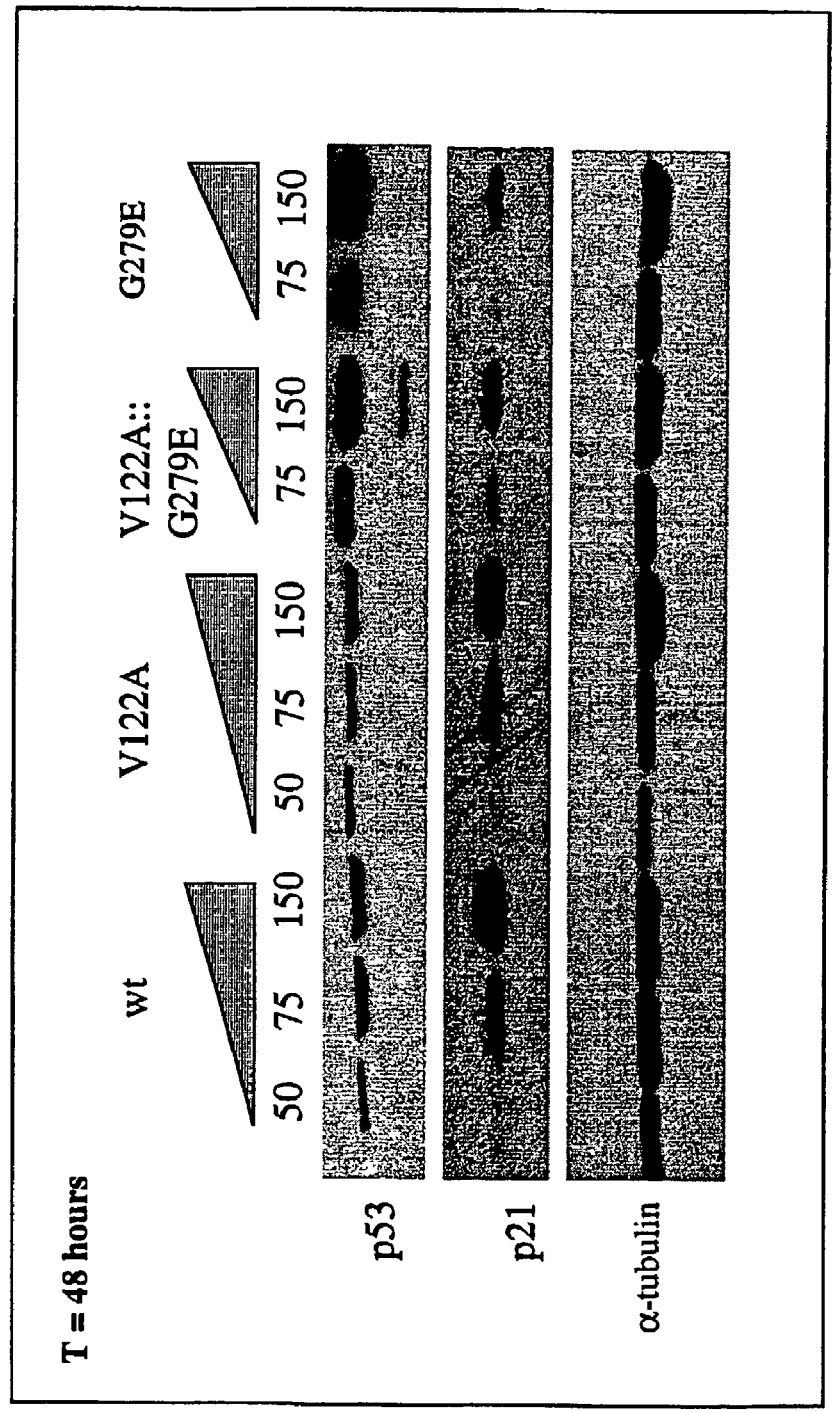

FIG. 6. Analysis of p21 induction by p53 V122A in Saos-2 cells. Saos-2 cells were transiently transfected by pCMV based plasmids containing wild type p53 or mutants using a lipofectin reagent. 100 ng of expression plasmid were transfected. Cells were recovered after 48 hours, extracts were prepared and 50-150 μg of extract was loaded in each lane. After transfer, the membrane was cut at a position corresponding to a 40 KD marker, in order to separately detect induction of p21 and alpha-tubulin. To detect p53 the membrane was stripped and reprobed.

Figure 7:
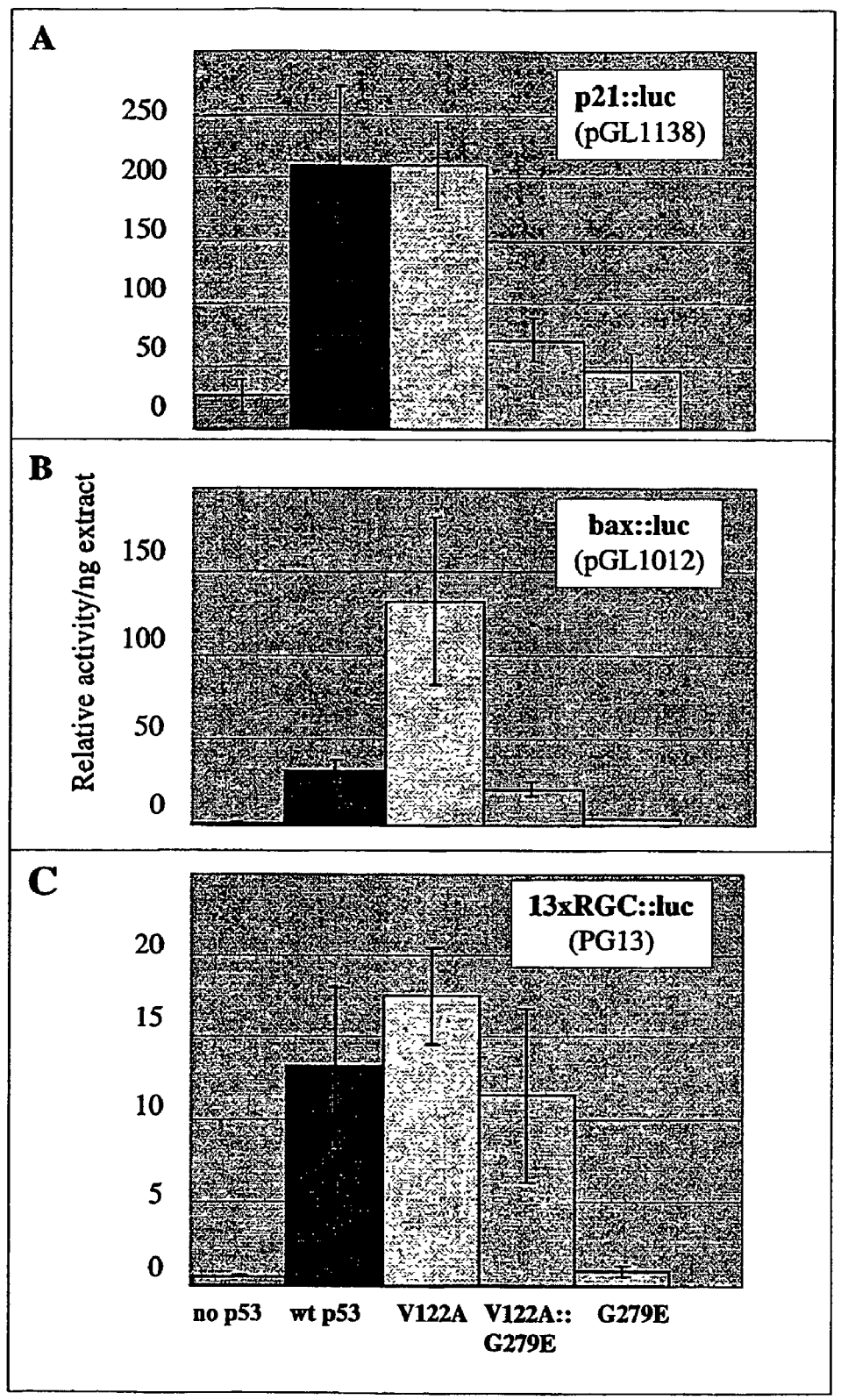

FIG. 7. p53 induction of a luciferase reporter in Saos-2 cells.

A luciferase based gene reporter assay was used to evaluate the transactivation potential of p53-V122A and p53 double mutants. Panels A and B: plasmids pGL1012 and pGL1138 contain the bax and p21 responsive elements next to a minimal promoter for the luciferase gene, respectively. Panel C: plasmid PG13 contains 13 copies of the RGC p53 responsive element. Transient transfections were performed with 50 or 100 ng of p53 expression plasmids and 1 μg of reporter plasmid. Cells were recovered 24 hours after transfection.

Figure 8:
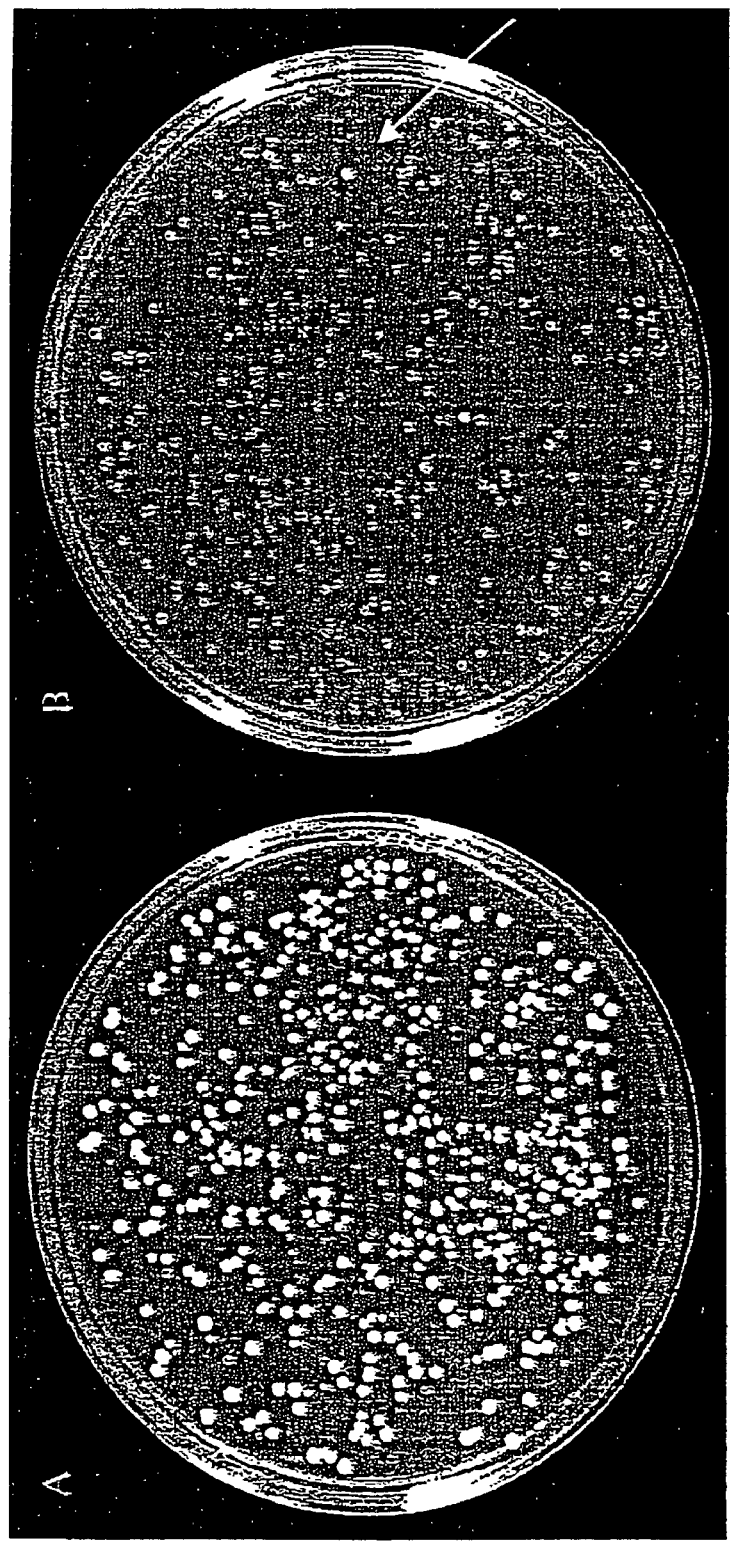

FIG. 8. A novel screen for p53 variants exhibiting increased transactivation. Presented are transformants obtained using PCR generated p53 cDNA directly cloned into a pADH1 (panel A) and a pGAL1 (panel B) expression vectors by recombination in yeast.

Panel A: on glucose plates with low adenine wild type p53 expression under pADH1 leads to white colonies. p53 transactivation mutants produce small red colonies.

Panel B: on raffinose plates containing low adenine expression under pGAL1 is low so that wild type p53 produces red colonies. White colonies (arrow) may reveal p53 alleles with increased transcriptional activation potential.

Figure 9:
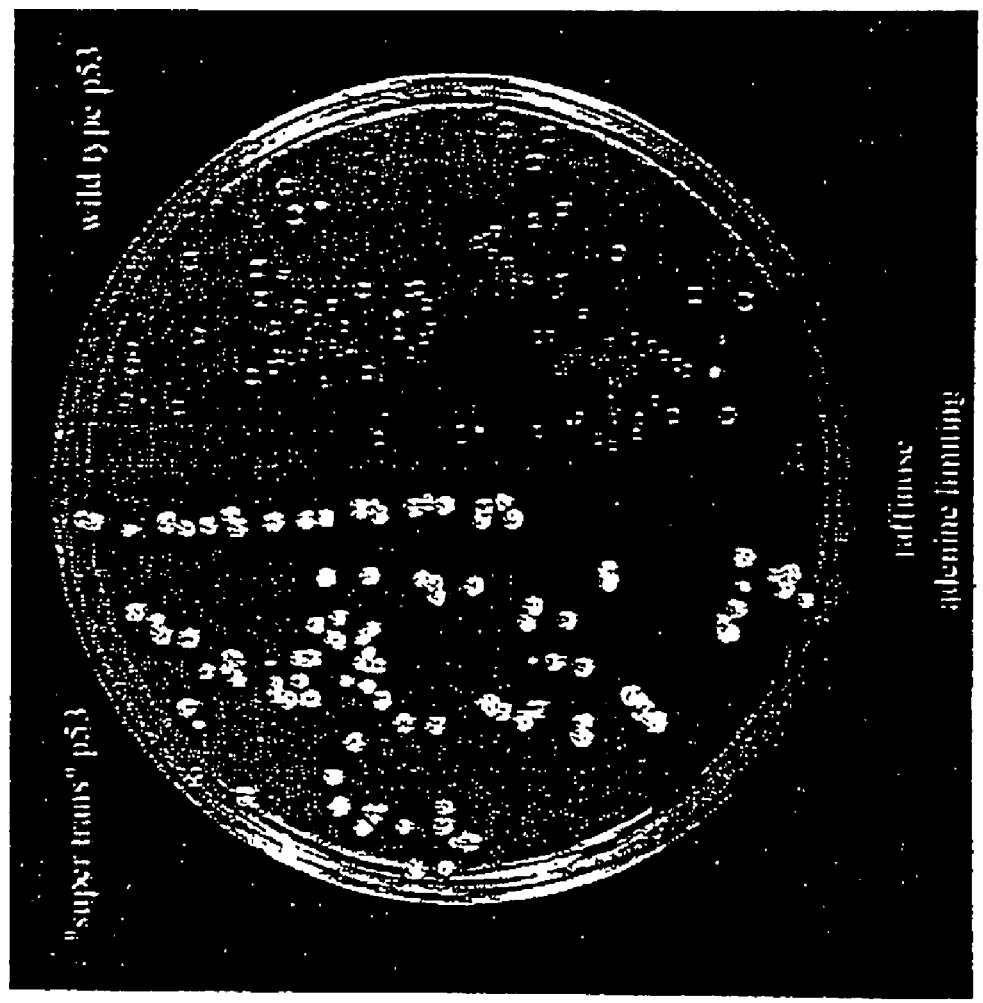

FIG. 9. The p53 cDNA fragment from nucleotide 124 to 1122 is responsible for increased transactivation. Left side: GAP repair cloning in pGAL1 plasmid of a PCR fragment generated using as template a rescued p53 plasmid showing increased transactivation in yeast. Right side: wild type p53 was used as template for the same kind of experiment. Cells are grown on raffinose as the carbon source, so that expression is low.

Figure 10:
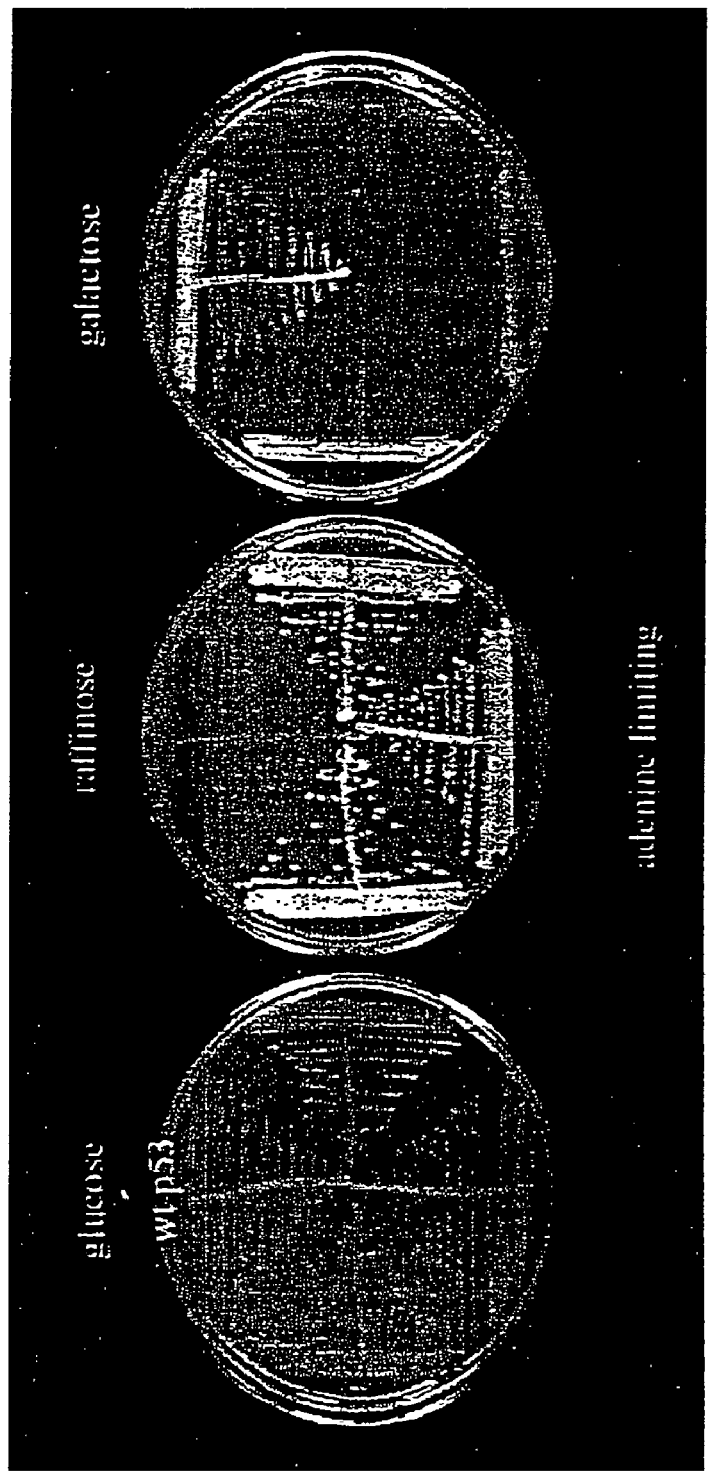

FIG. 10. Phenotypic analysis of variable expression of p53 variants disclosing increased transactivation compared to wild type p53. Transformants with pGAL1 plasmids expressing wild type p53 (top) or with three different "supertrans" alleles were tested on glucose (left), raffinose (center), and galactose (right) plates. "Supertrans" alleles are more growth inhibitory than wild type p53.

Figure 11:
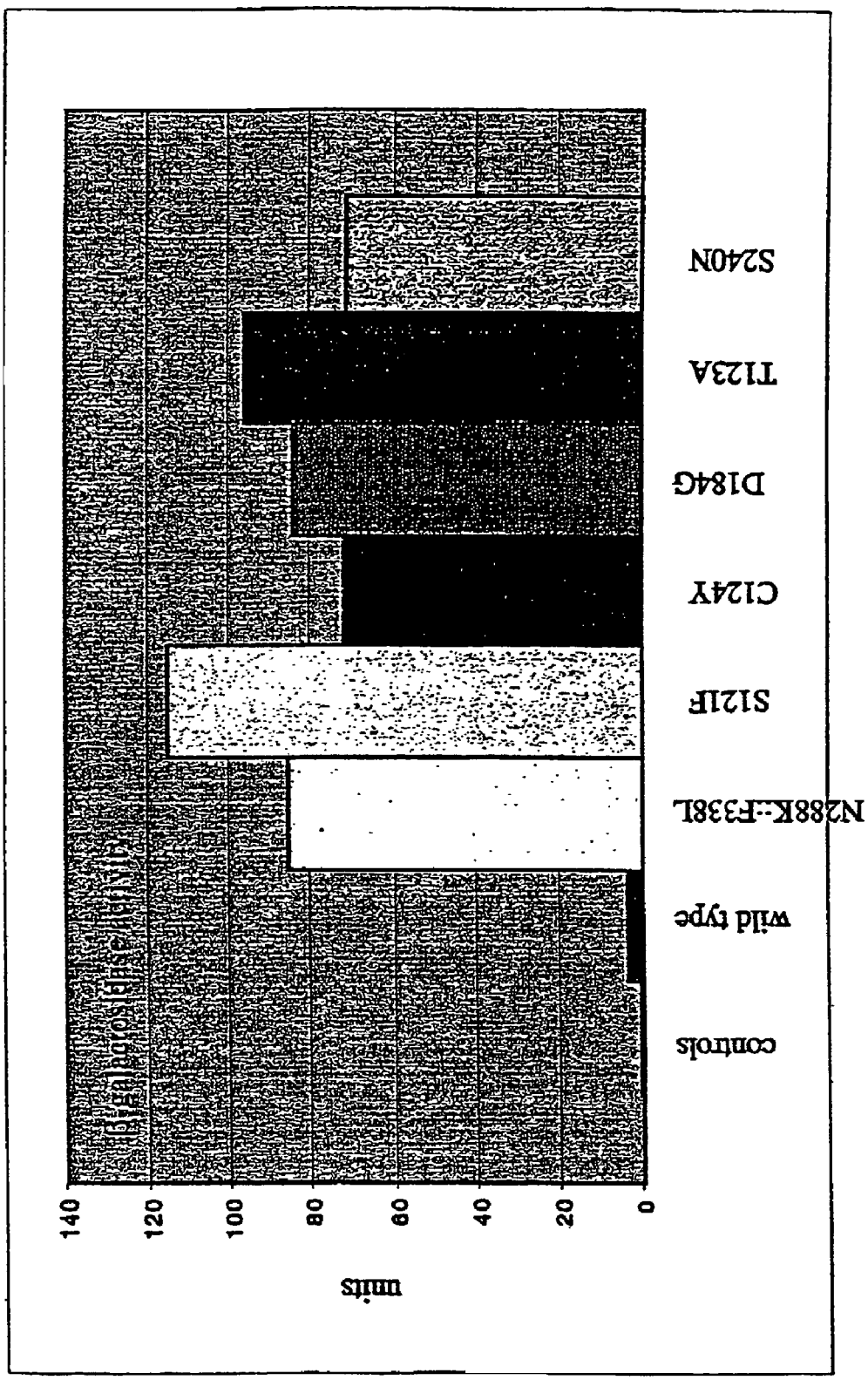

FIG. 11. β-galactosidase induction confirms the increased transactivation potential of the novel p53 alleles. β-galactosidase activity was measured after 8 hours of growth in raffinose liquid culture.

Figure 12:
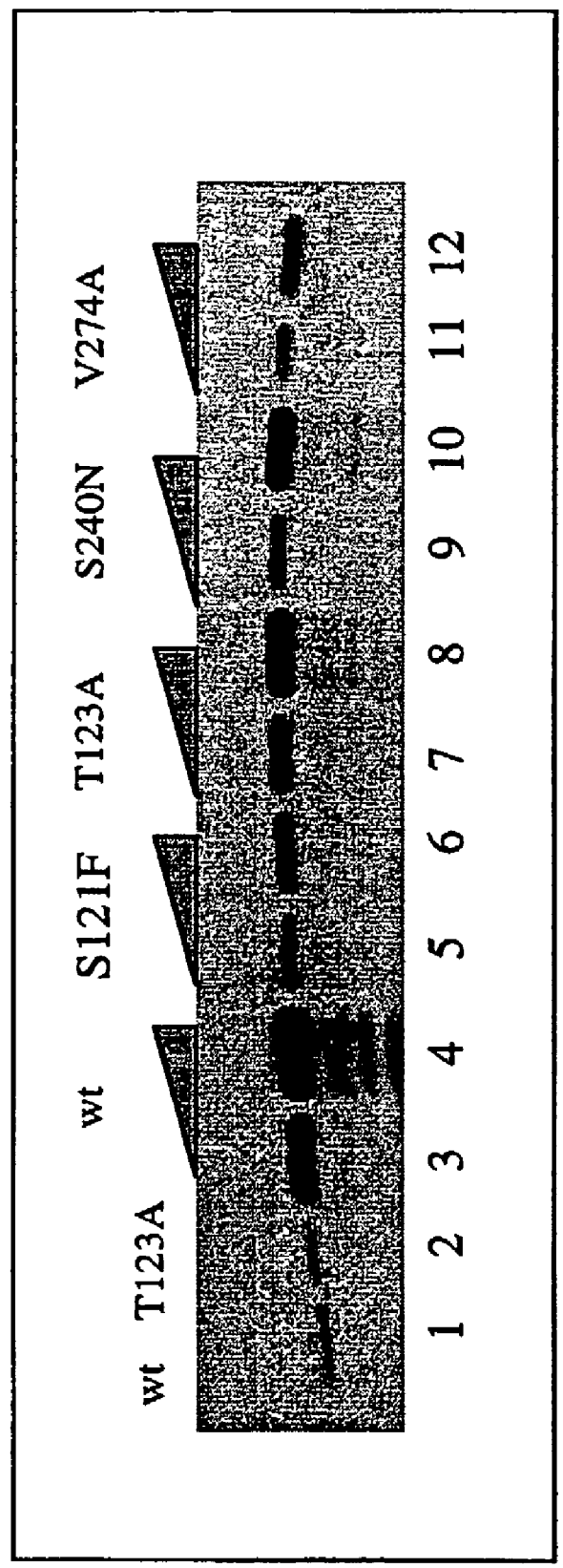

FIG. 12. Comparison of wild type p53 and supertrans mutant p53 protein expression levels.

Protein extracts were prepared from glucose (lane 1,2) or raffinose (lanes 3-12) cultures of yIG397 transformants containing pGAL1 p53 expression plasmids. 10 μg of protein extract was loaded on lanes 3, 5, 7, 9, 11. 50 μg were loaded on lanes 1, 2, 4, 6, 8, 10, 12. p53 was detected by DO-1 and pAb-1801 antibodies.

Figure 13:
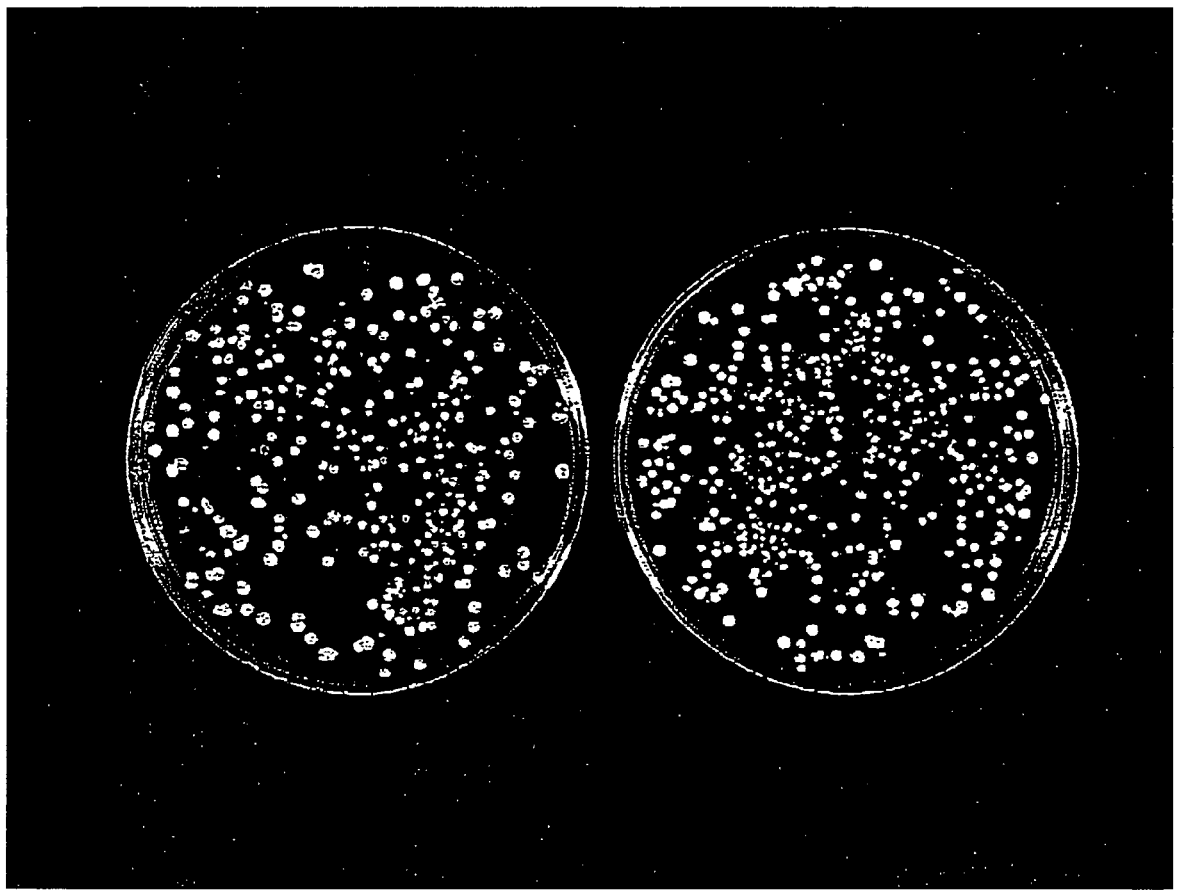

FIG. 13. p53-T123A is resistant to the dominant negative phenotype of p53-G279E. Panel A. yeast transformants with two vectors expressing wild type and p53-G279E under the ADH1 promoter. Pink colonies reflects the dominant negative phenotype of the mutant.

Panel B. yeast transformants with two vectors expressing p53-T123A and p53-G279E under the ADH1 promoter. Colonies are white, indicating wild type p53 activity.

Figure 14:
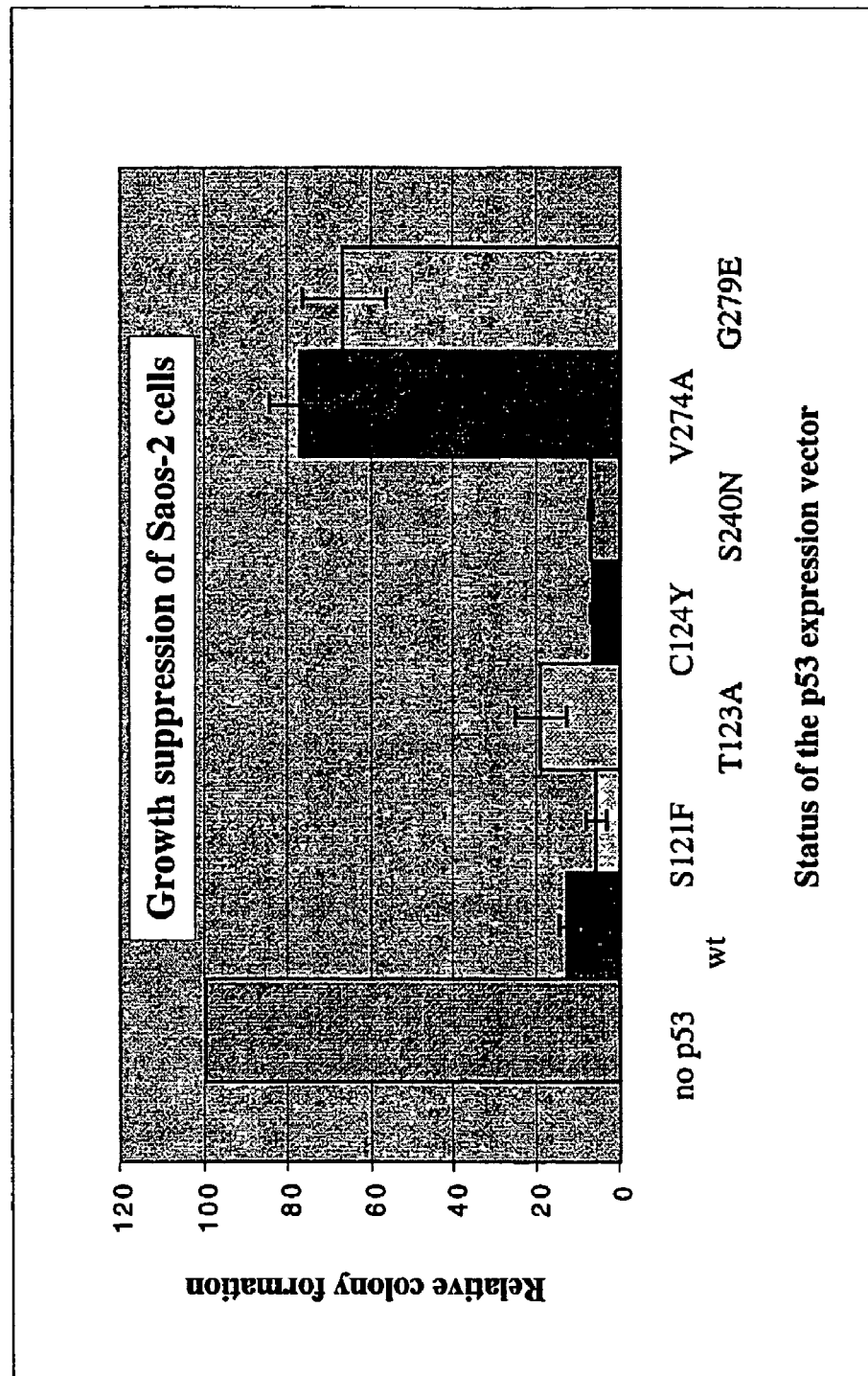

FIG. 14. Growth suppression by wild type and supertrans p53 alleles in human Saos-2 cells.

Saos-2 cells were transfected by lipofectin using 1 μg of vectors containing the different p53 alleles under the control of a CMV promoter. The relative average number of G418 resistant colonies and the standard errors for at least three experiments are presented.

Figure 15:
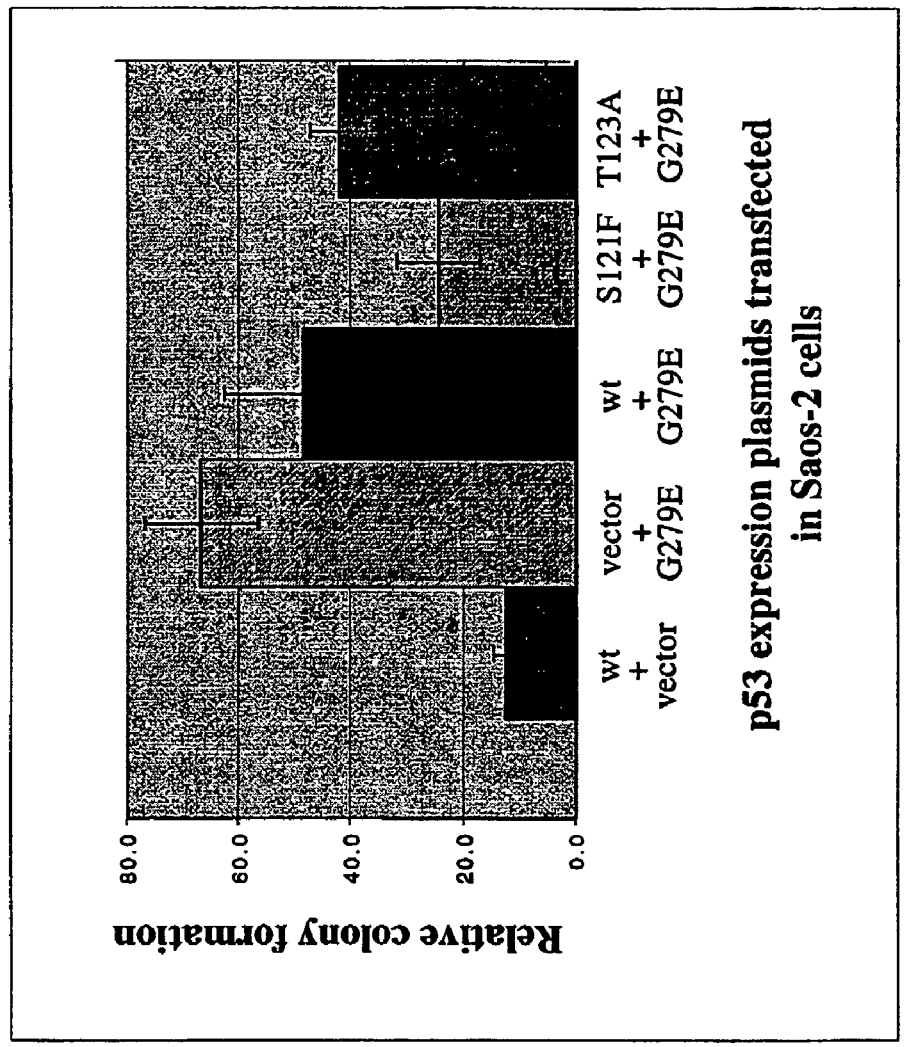

FIG. 15. Growth suppression by wild type and supertrans p53 alleles in the presence of a dominant negative tumor mutant.

Saos-2 cells were co-transfected with 250 ng of an identical vector expressing the indicated p53 alleles and with 1 μg of a pCMV-based vector expressing the G279E mutant (i.e., 1:4) and G418 resistant colonies were selected. The relative average number and the standard errors for three independent experiments are presented.

Figure 16:
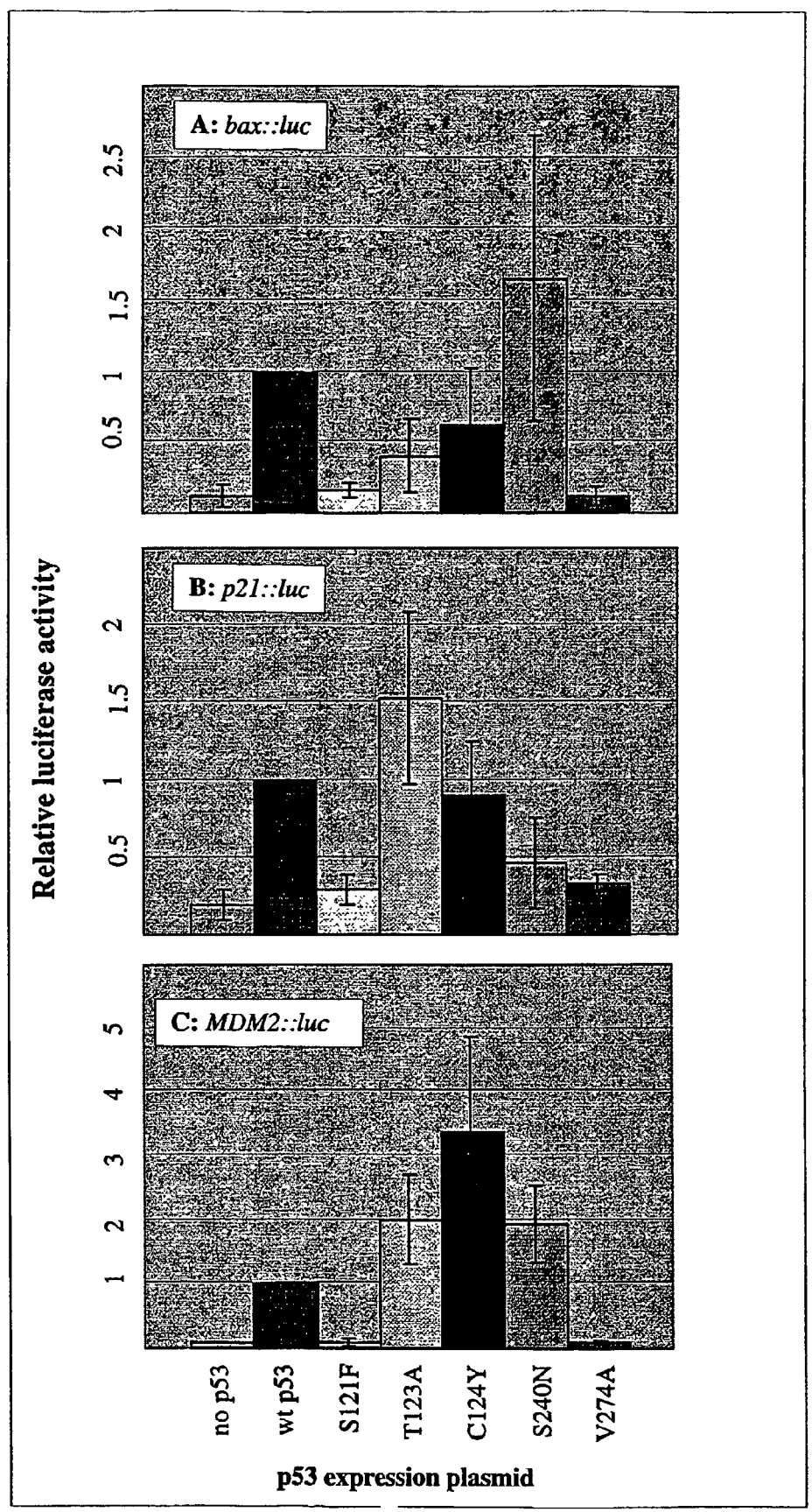

FIG. 16. Analysis of transactivation by supertrans p53 alleles by a luciferase reporter assay in Saos-2 cells.

Luciferase activity for each mutant and control vector is expressed relative to that obtained with wild type p53. The MDM2 and p21 promoters and the bax responsive elements were tested in panels A, B and C, respectively. Transient transfections using Fugene were performed with 20 ng of p53 expression plasmid and 500 ng of reporter plasmid in 12-well plate clusters. Cells were recovered 48 hours after transfection.

Figure 17:
Figure 17:
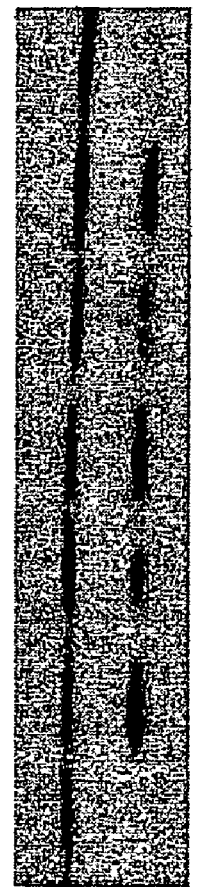

FIG. 17. p53 levels and endogenous p21 induction by wild type and supertrans p53 alleles in Saos-2 cells.

p53 and p21 protein levels in the same extracts used in the luciferase assays of FIG. 7 were determined by Western Blots. 100 μg of protein were loaded in each lane. After transfer, the membrane was cut at a position corresponding to a 40 KD marker in order to detect p21 and p53 separately.

Figure 18:
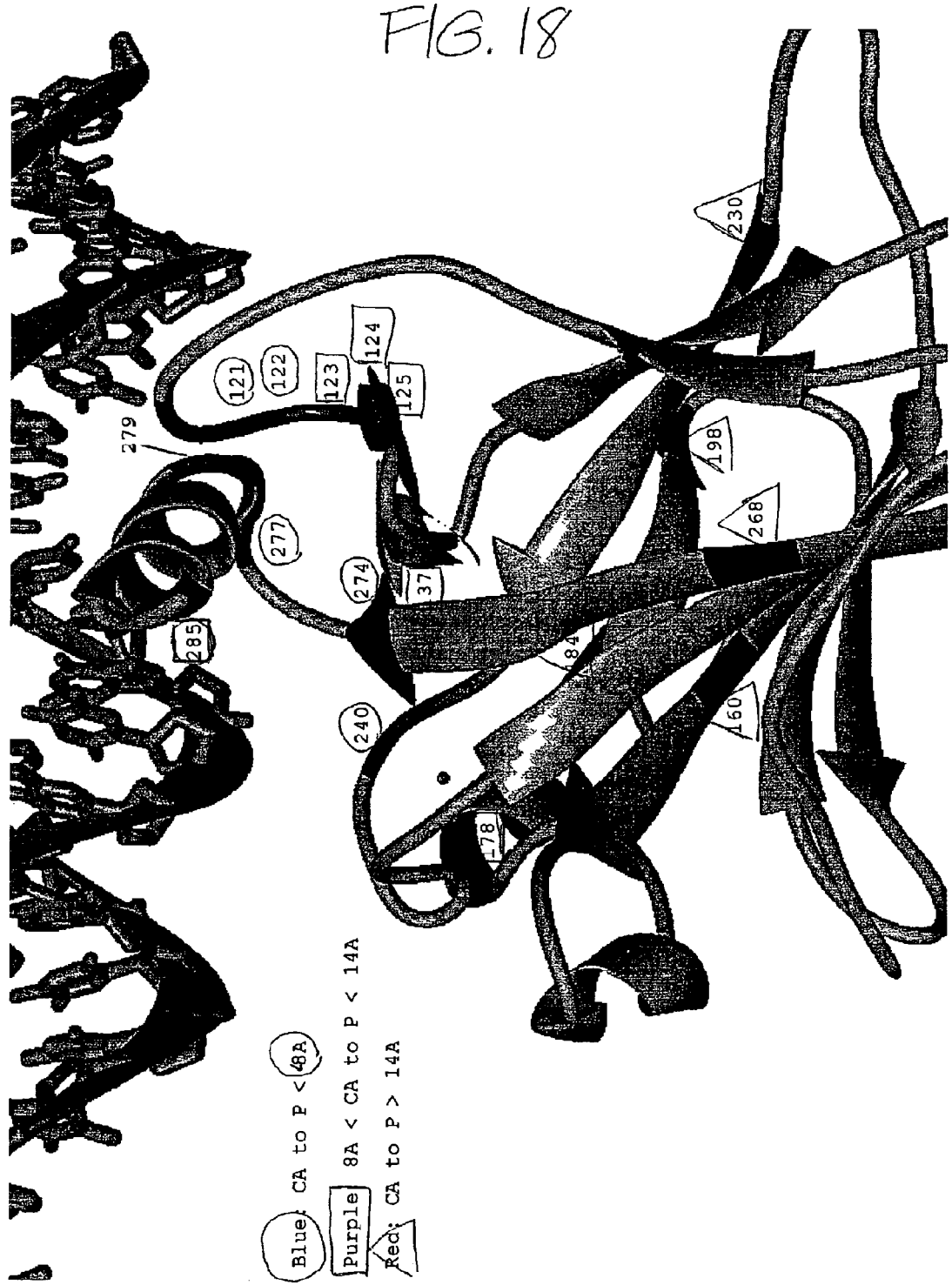

FIG. 18. Localization of the supertrans mutants in the p53 DNA binding domain. The position of the supertrans mutants described in Table 1 is shown on a ribbon representation of the monomeric DNA binding domain based on the crystal structure.

DETAILED DESCRIPTION OF THE INVENTION

The present invention may be understood more readily by reference to the following detailed description of the preferred embodiments of the invention and the Example included therein.

Before the present compounds and methods are disclosed and described, it is to be understood that this invention is not limited to specific proteins or specific methods. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise.

In the present invention "comprising" means that at least the elements specified are present. By "containing" is meant that at least the elements specified are present.

Human p53 Mutants

The present invention provides mutant forms of human p53. These mutations can cause certain phenotypes and may exert their effects via increased DNA binding affinity, alterations of DNA, altered specificity for p53 responsive elements, increased stability, a shift toward the tetrameric form of p53 or even via stronger or unidentified protein:protein interactions.

These mutants can include a toxic mutation of human p53. By "toxic" is meant a mutated human p53 that exhibits stronger growth inhibition of cells than wildtype p53 and could lead to cell death. The toxic mutation may exhibit strong growth inhibition or lead to cell death with or without the transactivating activity, i.e. the ability to induce transcription of a reporter gene via binding of the mutant to a promoter element containing p53 binding domains, for example, as measured in the yeast expression system of this invention. Cell death may occur via apoptosis, the transcription of genes involved in apoptosis, inappropriate transcription of genes possibly leading to necrosis, or other mechanisms of cell death, or DNA damage.

As used herein "apoptosis" refers to programmed cell death that has distinctive morphological and structural features that are different from those of pathological cell death or necrosis. The apoptotic process is characterized by nuclear fragmentation and cytoplasmic budding that lead to the formation of apoptotic bodies. These bodies are phagocytosed and destroyed by nearby macrophages. The fragmentation of the cells does not lead to the release of cellular contents, and the phagocytosis of the apoptotic bodies does not lead to inflammation. As a result, cell death can occur without damage to adjacent cells or tissues.

Another class of mutants identified by the present invention is the supertransactivating mutations or the supertransactivators. By "supertransactivating" or "supertransactivators" is meant a mutant p53 that possesses increased transcriptional activation in comparison to wildtype p53. These supertransactivating mutants may lead to stronger growth inhibition in cells when compared to wildtype p53 and could also lead to cell death. Therefore, some supertransactivating mutants are also toxic mutants.

The activity of supertransactivators can be modulated under certain conditions such as variations in the levels of supertransactivator protein expression as well as the type of responsive elements present for interaction with the supertransactivator. Examples of this activity are shown in Table 7, where it is shown that several supertransactivators possess varying levels of activity depending on the level of expression and/or selectivity for responsive elements.

The supertransactivating mutations can be dominant over the dominant negative effects that common tumor mutants exhibit, i.e. the supertransactivating mutation overcomes the dominant negative effect on transactivation that common tumor mutants exhibit over wild-type p53. By "dominant negative" is meant that in the presence of both the wild-type p53 and a mutant p53, the phenotype resulting from the mutant p53 is observed.

Further provided by this invention are tox-suppressor mutations. By "tox-suppressor" is meant a mutation in p53 that is capable of suppressing the toxic phenotype in cells produced by a toxic mutation in p53. By "suppressing" is meant a range of effects, ranging from a decrease in the effects of the toxic p53 mutation to complete reversal of the toxic phenotype where the toxic effects are no longer apparent. The tox-suppressor mutation can be a second mutation on a toxic p53 or a mutation on another p53 that leads to the suppression of the toxic mutant's effects on the cell. For example, if a toxic p53 is identified that results in cell death upon administration to cells, a second mutation can be introduced in the toxic mutant p53. If the second mutation suppresses the toxic p53 mutant's effects, cell growth should be observed, thus suppressing the toxic mutation's effects, i.e. strong growth inhibion or cell death.

Other mutations include mutant p53s that retain their transcriptional capabilities similar to wildtype p53, and trans-minus mutations of p53 which are mutant p53s that are not able to transactivate, i.e. bind to the p53 DNA binding element and induce the transcription of a gene, e.g. a reporter gene in a yeast expression assay.

The present p53 mutants provide opportunities to address structure-function relationships of p53. For example, several L1 loop mutations have defined different activities, including loss of transcriptional activity, supertransactivity (supertrans), toxicity and suppression of known mutations. These p53 mutants are also useful in analyzing functional domains and interactions. For example, super-trans or toxic mutants can be altered by the presence of a second mutations, such as a truncation in the same gene. In addition, toxic or supertransactivating mutations in different regions of the DNA binding domain or in the tetramerization domain could be combined to provide additional active variants.

The mutants also provide opportunities to examine dominance. This invention shows that levels of dominance can be investigated by varying the level of expression of the mutants. This was done for intragenic suppression. This invention also demonstrates intergenic suppression dominance, but this was only at one expression level. Mutants with varying levels of dominance are revealed using variable expression of the mutants. Furthermore, the mutants can be used to examine p53 mutants from human tissue. For example, a chimera can be generated (by transformation associated recombination) that contains one of the identified mutants (such as a supertransactivating or toxic) and a potential mutation from human tissue. Thus, naturally occurring mutations can be examined (or screened) in terms of their ability to reverse or modify the identified mutant. This intragenic suppressor/dominance screen provides an important tool for examining p53 cancer mutations.

The mutants can also be used to generate even stronger mutants of the same type. Once a mutant is identified, it is anticipated that subsequent second-site mutations can be generated that can further enhance the impact of the first mutation. For example, a supertransactivating mutation can be enhanced by a second mutation which would permit it to be detected at even lower levels of transcription than the single-mutation supertrans mutant thus resulting in a super-supertransactivating mutant. Similarly, a growth-inhibiting toxic mutant may be further mutated to generate a lethal mutant or result in lethality at lower expression levels.

The mutants also provide opportunities to examine chemical or drug interactions with wildtype or mutant p53, possibly relieving toxic effects, creating toxic effects, or creating or removing a supertransactivating effect.

Specifically, the present invention provides mutant polypeptides of human p53. These polypeptides can range in size from 10 amino acids in length to the full-length human p53. Particularly, the invention provides an isolated polypeptide comprising residues 117 to 127 of human p53 containing the mutation V122A, an isolated polypeptide comprising residues 272 to 282 of human p53 containing the mutation C277W, an isolated polypeptide comprising residues 70 to 80 of human p53 containing the mutation A76T, an isolated polypeptide comprising residues 272 to 282 of human p53 containing the mutation C277R, an isolated polypeptide comprising residues 145 to 155 of human p53 containing the mutation T150A, an isolated polypeptide comprising residues 115 to 125 of human p53 containing the mutation S121C, an isolated polypeptide comprising residues 120 to 130 of human p53 containing the mutation C124Y, an isolated polypeptide comprising residues 120 to 130 of human p53 containing the mutation C124F, an isolated polypeptide comprising residues 283 to 293 of human p53 containing the mutation N288K, an isolated polypeptide comprising residues 333 to 343 of human p53 containing the mutation F338L, an isolated polypeptide comprising residues 118 to 128 containing the mutation T123S, an isolated polypeptide comprising residues 193 to 203 of human p53 containing the mutation E198V, an isolated polypeptide comprising residues 110 to 120 of human p53 containing the mutation H115R, an isolated polypeptide comprising residues 50 to 150 of human p53 containing the mutation A76T and the mutation V122A, an isolated polypeptide comprising residues 50 to 200 of human p53 containing the mutation W91C, the mutation C124R, the mutation Q136K, and the mutation T150A, and an isolated polypeptide comprising residues 100 to 200 of human p53 containing the mutation C124R, the mutation Q136K, and the mutation T150A. The invention also provides mutant polypeptides of human p53 containing combinations of the above-mentioned mutations. The coordinates used herein to define the mutant p53 polypeptides of the invention are based on the published sequence of the human p53 (Zakut-Houri R., Bienz-Tadmor B., Givol D., Oren M. 1985. "Human p53 cellular tumor antigen: cDNA sequence and expression in COS cells" EMBO J. 4:1251-1255). The Zakut-Houri et al. reference is hereby incorporated in its entirety by this reference.

With regard to the polypeptides of this invention, as used herein, "isolated" and/or "purified" means a polypeptide which is substantially free from the naturally occurring materials with which the polypeptide is normally associated in nature. Also as used herein, "polypeptide" refers to a molecule comprised of amino acids which correspond to those encoded by a nucleic acid. The polypeptides of this invention can consist of the entire amino acid sequence of the mutant human p53 protein or fragments thereof of at least 5 amino acids in length. The polypeptides or fragments thereof of the present invention can be obtained by isolation and purification of the polypeptides from cells where they are produced naturally or by expression of exogenous nucleic acid encoding the mutant human p53 polypeptide.

These polypeptides can also be obtained in any of a number of procedures well known in the art. One method of producing a polypeptide is to link two peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to a particular protein can be synthesized by standard chemical reactions. For example, a peptide or polypeptide can be synthesized and not cleaved from its synthesis resin whereas the other fragment of a hybrid peptide can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form a larger polypeptide. (Grant, ASynthetic Peptides: A User Guide, W.H. Freeman and Co., N.Y. (1992) and Bodansky and Trost, Ed., A Principles of Peptide Synthesis, Springer-Verlag Inc., N.Y. (1993)). Alternatively, the peptide or polypeptide can be independently synthesized in vivo as described above. Once isolated, these independent peptides or polypeptides may be linked to form a larger protein via similar peptide condensation reactions.

For example, enzymatic ligation of cloned or synthetic peptide segments can allow relatively short peptide fragments to be joined to produce larger peptide fragments, polypeptides or whole protein domains (Abrahmsen et al. Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. A Synthesis of Proteins by Native Chemical Ligation, *Science,* 266:776-779 (1994)). The first step is the chemoselective reaction of an unprotected synthetic peptide-%-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Clark-Lewis et al. FEBS Lett., 307:97 (1987), Clark-Lewis et al., J. Biol. Chem., 269:16075 (1994), Clark-Lewis et al. Biochemistry, 30:3128 (1991), and Rajarathnam et al. Biochemistry, 29:1689 (1994)).

Alternatively, unprotected peptide segments can be chemically linked where the bond formed between the peptide segments as a result of the chemical ligation is an unnatural (non-peptide) bond (Schnolzer et al. Science, 256:221 (1992)). This technique has been used to synthesize analogs of protein domains as well as large amounts of relatively pure proteins with full biological activity (deLisle Milton et al. Techniques in Protein Chemistry IV, Academic Press, New York, pp. 257-267 (1992)).

Fragments of the mutant human p53 polypeptide can be obtained by standard chemical synthesis of peptides, by proteolytic cleavage of the polypeptide and by synthesis from nucleic acid encoding the portion of interest. For example, fragments of the human p53 polypeptide can comprise the amino acid sequence comprising residues 117 to 127 comprising the mutation V122A. Similarly, other fragments of mutant human p53 polypeptides can be obtained that contain a desired mutation. The polypeptide may include conservative substitutions where a naturally occurring amino acid is replaced by one having similar properties.

Thus, it is understood that, where desired, modifications and changes may be made in the nucleic acid and/or amino acid sequence of the mutant human p53 polypeptides of the present invention and still obtain a protein having like or otherwise desirable characteristics. Such changes may occur in natural isolates or may be synthetically introduced using site-specific mutagenesis, the procedures for which, such as mis-match polymerase chain reaction (PCR), are well known in the art.

For example, certain amino acids may be substituted for other amino acids in a mutant human p53 polypeptide without appreciable loss of functional activity. Since it is the interactive capacity and nature of a protein that defines that protein's biological functional activity, certain amino acid sequence substitutions can be made in a mutant human p53 amino acid sequence (or, of course, the underlying nucleic acid sequence) and nevertheless obtain a mutant human p53 polypeptide with like properties. It is thus contemplated that various changes may be made in the amino acid sequence of the mutant human p53 polypeptide (or underlying nucleic acid sequence) without appreciable loss of biological utility or activity and possibly with an increase in such utility or activity.

Also provided herein are purified antibodies that selectively or specifically bind to the polypeptides provided and contemplated herein The antibody (either polyclonal or monoclonal) can be raised to any of the polypeptides provided and contemplated herein, both naturally occurring and recombinant polypeptides, and immunogenic fragments, thereof. The antibody can be used in techniques or procedures such as diagnostics, treatment, or vaccination.

p53-Encoding Nucleic Acids

The present invention further provides nucleic acids encoding mutant human p53 polypeptides. As used herein, the term "nucleic acid" refers to single- or multiple stranded molecules which may be DNA or RNA, or any combination thereof, including modifications to those nucleic acids. The nucleic acid may represent a coding strand or its complement, or any combination thereof. Nucleic acids may be identical in sequence to the sequences which are naturally occurring (except for the presently mutated codons) for any of the novel genes discussed herein or may include alternative codons which encode the same amino acid (for the non-mutated amino acids) as that which is found in the naturally occurring sequence. These nucleic acids can also be modified from their typical structure. Such modifications include, but are not limited to, methylated nucleic acids, the substitution of a non-bridging oxygen on the phosphate residue with either a sulfur (yielding phosphorothioate deoxynucleotides), selenium (yielding phosphorselenoate deoxynucleotides), or methyl groups (yielding methylphosphonate deoxynucleotides).

Similarly, one skilled in the art will recognize that compounds comprising the, nucleic acids, and fragments of the nucleic acids as disclosed and contemplated herein are also provided. For example, a compound comprising a nucleic acid can be a derivative of a typical nucleic acid such as nucleic acids which are modified to contain a terminal or internal reporter molecule and/or those nucleic acids containing non-typical bases or sugars. These reporter molecules include, but are not limited to, isotopic and non-isotopic reporters. Therefore any molecule which may aid in detection, amplification, replication, expression, purification, uptake, etc. may be added to the nucleic acid construct.

Once a nucleic acid encoding a particular protein of interest, or a region of that nucleic acid, is constructed, modified, or isolated, that nucleic acid can then be cloned into an appropriate vector, which can direct the in vivo or in vitro synthesis of that wild-type and/or modified protein. The vector is contemplated to have the necessary functional elements that direct and regulate transcription of the inserted gene, or nucleic acid. These functional elements include, but are not limited to, a promoter, regions upstream or downstream of the promoter, such as enhancers that may regulate the transcriptional activity of the promoter, an origin of replication, appropriate restriction sites to facilitate cloning of inserts adjacent to the promoter, antibiotic resistance genes or other markers which can serve to select for cells containing the vector or the vector containing the insert, RNA splice junctions, a transcription termination region, or any other region which may serve to facilitate the expression of the inserted gene or hybrid gene. (See generally, Sambrook et al.).

There are numerous *E. coli* (*Escherichia coli*) expression vectors known to one of ordinary skill in the art which are useful for the expression of the nucleic acid insert. Other microbial hosts suitable for use include bacilli, such as *Bacillus subtilis*, and other enterobacteriaceae, such as *Salmonella, Serratia*, and various *Pseudomonas* species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences for example, for initiating and completing transcription and translation. If necessary, an amino terminal methionine can be provided by insertion of a Met codon 5' and in-frame with the downstream nucleic acid insert. Also, the carboxy-terminal extension of the nucleic acid insert can be removed using standard oligo-nucleotide mutagenesis procedures.

Additionally, yeast expression can be used. There are several advantages to yeast expression systems. First, evidence exists that proteins produced in a yeast secretion systems exhibit correct disulfide pairing. Second, post-translational glycosylation is efficiently carried out by yeast secretory systems. The *Saccharomyces cerevisiae* pre-pro-alpha-factor leader region (encoded by the MF"-1 gene) is routinely used to direct protein secretion from yeast. (Brake, et al. "∝-Factor-Directed Synthesis and Secretion of Mature Foreign Proteins in *Saccharomyces cerevisiae*." Proc. Nat. Acad. Sci., 81:4642-4646 (1984)). The leader region of pre-pro-alpha-factor contains a signal peptide and a pro-segment which includes a recognition sequence for a yeast protease encoded by the KEX2 gene: this enzyme cleaves the precursor protein on the carboxyl side of a Lys-Arg dipeptide cleavage signal sequence. The nucleic acid coding sequence can be fused in-frame to the pre-pro-alpha-factor leader region. This construct is then put under the control of a strong transcription promoter, such as the alcohol dehydrogenase I promoter or a glycolytic promoter. The nucleic acid coding sequence is followed by a translation termination codon which is followed by transcription termination signals. Alternatively, the nucleic acid coding sequences can be fused to a second protein coding sequence, such as Sj26 or β-galactosidase, used to facilitate purification of the fusion protein by affinity chromatography. The insertion of protease cleavage sites to separate the components of the fusion protein is applicable to constructs used for expression in yeast. Efficient post translational glycosylation and expression of recombinant proteins can also be achieved in Baculovirus systems.

Mammalian cells permit the expression of proteins in an environment that favors important post-translational modifications such as folding and cysteine pairing, addition of complex carbohydrate structures, and secretion of active protein. Vectors useful for the expression of active proteins in mammalian cells are characterized by insertion of the protein coding sequence between a strong viral promoter and a polyadenylation signal. The vectors can contain genes conferring hygromycin resistance, gentamicin resistance, or other genes or phenotypes suitable for use as selectable markers, or methotrexate resistance for gene amplification. The chimeric protein coding sequence can be introduced into a Chinese hamster ovary (CHO) cell line using a methotrexate resistance-encoding vector, or other cell lines using suitable selection markers. Presence of the vector DNA in transformed cells can be confirmed by Southern blot analysis. Production of RNA corresponding to the insert coding sequence can be confirmed by Northern blot analysis. A number of other suitable host cell lines capable of secreting intact human proteins have been developed in the art, and include the CHO cell lines, HeLa cells, myeloma cell lines, Jurkat cells, etc. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc. The vectors containing the nucleic acid segments of interest can be transferred into the host cell by well-known methods, which vary depending on the type of cellular host. For example, calcium chloride transformation is commonly utilized for prokaryotic cells, whereas calcium phosphate, DEAE dextran, or lipofectin mediated transfection or electroporation may be used for other cellular hosts.

Alternative vectors for the expression of genes or nucleic acids in mammalian cells, those similar to those developed for the expression of human gamma-interferon, tissue plasminogen activator, clotting Factor VIII, hepatitis B virus surface antigen, protease Nexinl, and eosinophil major basic protein, can be employed. Further, the vector can include CMV promoter sequences and a polyadenylation signal available for expression of inserted nucleic acids in mammalian cells (such as COS-7).

Insect cells also permit the expression of mammalian proteins. Recombinant proteins produced in insect cells with baculovirus vectors undergo post-translational modifications similar to that of wild-type proteins. Briefly, baculovirus vectors useful for the expression of active proteins in insect cells are characterized by insertion of the protein coding sequence downstream of the *Autographa californica* nuclear polyhedrosis virus (AcNPV) promoter for the gene encoding polyhedrin, the major occlusion protein. Cultured insect cells such as *Spodoptera frugiperda* cell lines are transfected with a mixture of viral and plasmid DNAs and the viral progeny are plated. Deletion or insertional inactivation of the polyhedrin gene results in the production of occlusion negative viruses which form plaques that are distinctively different from those of wild-type occlusion positive viruses. These distinctive plaque morphologies allow visual screening for recombinant viruses in which the AcNPV gene has been replaced with a hybrid gene of choice.

Alternatively, the genes or nucleic acids of the present invention can be operatively linked to one or more of the functional elements that direct and regulate transcription of the inserted gene as discussed above and the gene or nucleic acid can be expressed. For example, a gene or nucleic acid can be operatively linked to a bacterial or phage promoter and used to direct the transcription of the gene or nucleic acid in vitro. A further example includes using a gene or nucleic acid provided herein in a coupled transcription-translation system where the gene directs transcription and the RNA thereby produced is used as a template for translation to produce a polypeptide. One skilled in the art will appreciate that the products of these reactions can be used in many applications such as using labeled RNAs as probes and using polypeptides to generate antibodies or in a procedure where the polypeptides are being administered to a cell or a subject.

Expression of the gene or nucleic acid, either in combination with a vector or operatively linked to an appropriate sequence, can be by either in vivo or in vitro. In vivo synthesis comprises transforming prokaryotic or eukaryotic cells that can serve as host cells for the vector. Alternatively, expression of the gene or nucleic acid can occur in an in vitro expression system. For example, in vitro transcription systems are commercially available which are routinely used to synthesize relatively large amounts of mRNA. In such in vitro transcription systems, the nucleic acid encoding the desired gene would be cloned into an expression vector adjacent to a transcription promoter. For example, the Bluescript II cloning and expression vectors contain multiple cloning sites which are flanked by strong prokaryotic transcription promoters. (Stratagene Cloning Systems, La Jolla, Calif.). Kits are available which contain all the necessary reagents for in vitro synthesis of an RNA from a DNA template such as the Bluescript vectors. (Stratagene Cloning Systems, La Jolla, Calif.). RNA produced in vitro by a system such as this can then be translated in vitro to produce the desired protein. (Stratagene Cloning Systems, La Jolla, Calif.).

If ex vivo methods are employed, cells or tissues can be removed and maintained outside the body according to standard protocols well known in the art. The nucleic acids of this invention can be introduced into the cells via any gene transfer mechanism, such as, for example, virus-mediated gene delivery, calcium phosphate mediated gene delivery, electroporation, microinjection or proteoliposomes. The transduced cells can then be infused (e.g., in a pharmaceutically acceptable carrier) or homotopically transplanted back into a subject per standard methods for the cell or tissue type. Standard methods are known for transplantation or infusion of various cells into a subject.

The nucleic acids of this invention can also be utilized for in vivo gene therapy techniques (U.S. Pat. No. 5,399,346). With regard to gene therapy applications, the nucleic acid can comprise a nucleotide sequence which encodes a gene product which is meant to function in the place of a defective gene product and restore normal function to a cell which functioned abnormally due to the defective gene product. Alternatively, the nucleic acid may encode a gene product which was not previously present in a cell or was not previously present in the cell at a therapeutic concentration, whereby the presence of the exogenous gene product or increased concentration of the exogenous gene product imparts a therapeutic benefit to the cell and/or to a subject.

For in vivo administration, the cells can be in a subject and the nucleic acid can be administered in a pharmaceutically acceptable carrier. The subject can be any animal in which it is desirable to selectively express a nucleic acid in a cell. In a preferred embodiment, the animal of the present invention is a human. In addition, non-human animals which can be treated by the method of this invention can include, but are not limited to, cats, dogs, birds, horses, cows, goats, sheep, guinea pigs, hamsters, gerbils and rabbits, as well as any other animal in which selective expression of a nucleic acid in a cell can be carried out according to the methods described herein.

In the method described above which includes the introduction of exogenous DNA into the cells of a subject (i.e., gene transduction or transfection), the nucleic acids of the present invention can be in the form of naked DNA or the nucleic acids can be in a vector for delivering the nucleic acids to the cells for expression of the nucleic acid inside the cell. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as Lipofectin®, Lipofectamine® (GIBCO-BRL, Inc., Gaithersburg, Md.), Superfect® (Qiagen, Inc. Hilden, Germany) and Transfectam® (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a Sonoporation machine (ImaRx Pharmaceutical Corp., Tucson, Ariz.).

As one example, vector delivery can be via a viral system, such as a retroviral vector system which can package a recombinant retroviral genome. The recombinant retrovirus can then be used to infect and thereby deliver nucleic acid to the infected cells. The exact method of introducing the nucleic acid into mammalian cells is, of course, not limited to the use of retroviral vectors. Other techniques are widely available for this procedure including the use of adenoviral vectors, adeno-associated viral (AAV) vectors, lentiviral vectors, pseudotyped retroviral vectors, and pox virus vectors, such as vaccinia virus vectors. Physical transduction techniques can also be used, such as liposome delivery and receptor-mediated and other endocytosis mechanism. This invention can be used in conjunction with any of these or other commonly used gene transfer methods.

The nucleic acid and the nucleic acid delivery vehicles of this invention, (e.g., viruses; liposomes, plasmids, vectors) can be in a pharmaceutically acceptable carrier for in vivo administration to a subject. By "pharmaceutically acceptable" is meant a material that is not biologically or otherwise undesirable, i.e., the material may be administered to a subject, along with the nucleic acid or vehicle, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The nucleic acid or vehicle may be administered orally, parenterally (e.g., intravenously), by intramuscular injection, by intraperitoneal injection, transdermally, extracorporeally, topically or the like. The exact amount of the nucleic acid or vector required will vary from subject to subject, depending on the species, age, weight and general condition of the subject, the severity or mechanism of any disorder being treated, the particular nucleic acid or vehicle used, its mode of administration and the like.

Screening Methods

The present invention further provides screening methods for identifying toxic, supertransactivating, and tox-suppressor mutations in human p53.

Specifically, this invention provides a method of detecting a supertransactivating mutation in the human p53 gene comprising: a) obtaining a yeast cell comprising a reporter gene, wherein the reporter gene is linked to a DNA sequence to which human p53 binds; b) introducing into the yeast cell a nucleic acid which expresses a human p53, the nucleic acid comprising an inducible promoter comprising GAL 1 linked to the human p53 coding sequence; c) plating the yeast cell of step b) on raffinose as the carbon source; and identifying colonies on plates, wherein colonies expressing wild type p53 yield red colonies and colonies expressing a supertransactivating mutation in p53 yield white or pink colonies.

In this invention the GAL 1 promoter can be GAL 1 or any other fragment or unit of the GAL1-10 promoter. In this invention, "plating" can also include replica plating. The yeast strains of this invention can be incubated on plates containing a carbon source as well as in liquid culture containing a carbon source. By utilizing raffinose as a carbon source is meant that raffinose is the main carbon source, but the media, either in plates or in liquid culture could contain trace amounts of other carbon sources without significantly affecting the results obtained.

In this screening method, variable expression of p53 is achieved using the GAL1 promoter and by changing the carbon source in the medium. In particular, the GAL1 promoter allows a basal level of expression when raffinose is used as a unique carbon source, because the glucose repression system is removed, but the promoter is not induced. In this situation p53 levels are so low that the wildtype cannot activate transcription of the reporter gene (in this case ADE2) efficiently and the color of the colonies remains red. Thus, p53 supertransactivating mutants that, either because of increased stability or stronger binding to the ribosomal gene cluster (RGC) sequence, perform transactivation more efficiently than wildtype, and can produce white yeast colonies and be easily identified on raffinose. Also contemplated by this invention is the use of other inducible promoter systems such as PHO5 and the glucocorticoid resposive element system in the methods of the invention (Vectors for Expression of cloned genes in yeast: regulation, overproduction and underproduction. Jane. C. Schneider and Leonard Guarente in Guide to Yeast Genetics and Molecular Biology; Methods in Enzymology Edited by Christine Guthrie and Gerald R. Fink; Volume 194 pp 373-388.) The methods of the present invention can be adapted to utilize any inducible promoter system in the presence of the appropriate inducer.

Other reporter genes that can be utilized include HIS3, LEU2, URA3 in yeast strains that are deficient for HIS3, LEU2 and URA3, respectively. When utilizing these reporter genes, the screening can be performed by selecting colonies expressing p53 variants at very low levels of induction (under control of GAL1 and on raffinose medium) and looking for growth on plates lacking histidine, leucine, and uracil, respectively. The following methods are provided for detecting a supertransactivating mutation by utilizing different reporters. A method of detecting a supertransactivating mutation in the human p53 gene comprising, obtaining a yeast cell comprising a HIS3 reporter gene, wherein the reporter gene is linked to a DNA sequence to which human p53 binds; introducing into the yeast cell a nucleic acid which encodes a human p53, the nucleic acid comprising an inducible promoter comprising GAL 1 linked to a human 53 coding sequence; plating the yeast cell on raffinose as a carbon source; and raffinose plus a small amount of galactose in synthetic medium lacking histidine; identifying colonies on plates, wherein normal size colonies expressing a transactivating mutation in p53 grow on raffinose or on raffinose plus a small amount of galactose medium without histidine and wherein cells expressing wild type p53 do not grow or grow poorly.

Also provided is a method of detecting a supertransactivating mutation in the human p53 gene comprising: obtaining a yeast cell comprising a URA3 reporter gene, wherein the reporter gene is linked to a DNA sequence to which human p53 binds; introducing into the yeast cell a nucleic acid which encodes a human p53, the nucleic acid comprising an inducible promoter comprising GAL 1 linked to a human 53 coding sequence; plating the yeast cell on raffinose as a carbon source; and raffinose plus a small amount of galactose in synthetic medium lacking uracil; identifying colonies on plates, wherein normal size colonies expressing a transactivating mutation in p53 grow on raffinose or on raffinose plus a small amount of galactose medium without uracil and wherein cells expressing wild type p53 do not grow or grow poorly.

Further provided is a method of detecting a supertransactivating mutation in the human p53 gene comprising: obtaining a yeast cell comprising a LEU2 reporter gene, wherein the reporter gene is linked to a DNA sequence to which human p53 binds; introducing into the yeast cell a nucleic acid which encodes a human p53, the nucleic acid comprising an inducible promoter comprising GAL 1 linked to a human 53 coding sequence; plating the yeast cell on raffinose as a carbon source; and raffinose plus a small amount of galactose in synthetic medium lacking leucine; identifying colonies on plates, wherein normal size colonies expressing a transactivating mutation in p53 grow on raffinose or on raffinose plus a small amount of galactose medium without leucine and wherein cells expressing wild type p53 do not grow or grow poorly.

By utilizing the present screening method for detecting supertransactivating mutant p53s, mutants exhibiting altered sequence specificity can be isolated and analyzed. These mutants might possess a supertransactivating activity toward some p53 responsive elements and a defect in DNA recognition of other slightly different p53 responsive elements. Those alleles may be useful in functionally dissecting the p53 downstream pathway to understand the components that are most relevant in tumor suppression or for specific activation of genes such as apoptosis genes. These supertransactivating mutants could also be used in therapies that combine restoration of wildtype-like p53 activity and apoptosis to tumor cells along with chemotherapy. The ability to supertransactivate specific genes is particularly useful, since some genes are much more relevant to cell inactivation, such as apoptosis genes. The supertransactivating dominance can be used to counteract the dominant negative impact of various tumor mutations.

Determination of transactivation by supertransactivating p53 mutants at different expression levels and with different p53 responsive elements can be achieved by: obtaining a first yeast cell comprising a reporter gene, wherein the reporter gene is linked to a first DNA sequence to which human p53 binds; introducing into the first yeast cell a nucleic acid which encodes a human p53, the nucleic acid comprising an inducible promoter comprising GAL 1 linked to a human p53 coding sequence; obtaining a second yeast cell comprising a reporter gene, wherein the reporter gene is linked to a second DNA sequence to which human p53 binds; introducing into the second yeast cell a nucleic acid which encodes a human p53, the nucleic acid comprising an inducible promoter comprising GAL 1 linked to a human p53 coding sequence; plating the first and second yeast cell on each of glucose, raffinose, raffinose and galactose, and raffinose and more galactose; identifying colonies on plates, wherein white or pink colonies indicate transactivation has occurred; and determining the level of supertransactivaton of the first and the second DNA sequence under different levels of expression by the p53. A control can also be included wherein the reporter is linked to the 3XRGC element.

The assay can be set up with more than two responsive elements. For example, an assay that compares the effects of a p53 mutant on 3, 4, 5, 6, 7, 8, 9, 10, 11, 12, 13, 14, 15, 16 or more responsive elements can be performed utilizing the above method. In fact, any p53 responsive element can be used in the present screening method. For example, the DNA sequences to which p53 binds can be the 3xRGC responsive element, the PIG3 responsive element, the p21 responsive element, the bax responsive element or any other DNA sequence which p53 binds. The yeast cells are plated on glucose, raffinose, raffinose and galactose, and raffinose and more galactose in order to measure transactivation under conditions of varying expression levels. Expression levels are lowest in glucose, higher in raffinose and much higher in raffinose plus galactose. By raffinose and more galactose is meant a concentration of galactose that is higher than the concentration of raffinose and galactose. The amount of galactose added to raffinose containing plates can be varied from trace amounts to 2.0% galactose in order to obtain variable amounts of p53 expression. For example, the yeast cells can be plated on glucose, glucose and raffinose, glucose and 0.003% galactose, and glucose and 0.015% galactose. In this example, 0.015% galactose is more than 0.003% galactose. In another example, the yeast cells can be plated on glucose, glucose and raffinose, glucose and 0.005% galactose and glucose and 0.016% galactose. By varying expression levels, the skilled artisan can detect differences in the transactivation of a responsive element such as 3xRGC, PIG3, p21 or bax. This assay will allow one skilled in the art to determine if a particular p53 mutant is supertransactivating for one responsive element at lower expression levels and supertransactivating for another responsive element at higher expression levels. Also, this assay allows for the identification of mutants that are selective for a particular responsive element or subset of responsive elements. This screening assay can also be performed with other inducible promoter systems in order to determine selectivity of supertransactivators for p53 responsive elements.

For example, if the skilled artisan conducted the above-mentioned assay and looked at the plates corresponding to mutant S121F (Table 7), they would note that: 1) white colonies are seen for the 3XRGC responsive element in the 2% raffinose plates, the 2% raffinose+0.003% galactose plates and in the 2% raffinose+0.015% galactose plates; 2) white colonies are seen for the PIG3 element in the 2% raffinose plates, the 2% raffinose+0.003% galactose plates and in the 2% raffinose+0.015% galactose plates; 3) white colonies are seen for the p21 responsive element in the 2% raffinose+0.015% galactose plates; and 4) pink colonies are seen for the bax element in the 2% raffinose plates and white colonies are seen in the 2% raffinose+0.003% galactose plates and in the 2% raffinose+0.015% galactose plates. Thus, one skilled in the art would conclude that the S121F mutant is supertransactivating for the 3XRGC element, the PIG3 element and the bax element at lower levels of expression as compared to wildtype, but not for the p21 responsive element. Based on this information, one skilled in the art can select particular mutant p53s to target specific pathways based on their ability to transactivate a particular responsive element. For example, a mutant exhibiting increased or supertransactivation activity for the PIG3 pathway can be used to modulate that pathway and one exhibiting supertransactivation activity for the p21 pathway can be utilized to modulate the p21 pathway. Since the same supertransactivating mutation can transactivate one responsive element at low levels of expression and another responsive element at higher levels, one skilled in the art could target more than one responsive element with the same mutation by varying the amount of supertransactivator.

Also, as described above for the identification of p53 mutants, this screening method can also be accomplished by utilizing a yeast strain containing a reg1-501 mutation. Therefore, this invention provides a method of determining transactivation by supertransactivating p53 mutants at different expression levels and with different p53 responsive elements by: obtaining a first reg1-501 mutant yeast cell comprising a reporter gene, wherein the reporter gene is linked to a first DNA sequence to which human p53 binds; introducing into the first reg1-501 mutant yeast cell a nucleic acid which encodes a human p53, the nucleic acid comprising an inducible promoter comprising GAL 1 linked to a human p53 coding sequence; obtaining a second reg1-501 mutant yeast cell comprising a reporter gene, wherein the reporter gene is linked to a second DNA sequence to which human p53 binds; introducing into the second reg1-501 mutant yeast cell a nucleic acid which encodes a human p53, the nucleic acid comprising an inducible promoter comprising GAL 1 linked to a human p53 coding sequence; plating the first and second yeast cell on each of glucose, and glucose and increasing concentrations of galactose, identifying colonies on plates, wherein white or pink colonies indicate supertransactivation has occurred; and determining the level of supertransactivaton of the first and the second DNA sequence under different levels of expression by the p53. A control can also be included wherein the reporter is linked to the 3XRGC element. The yeast cells are plated on glucose and increasing concentrations of galactose in order to measure transactivation under conditions of varying expression levels. This assay can be performed by plating the cells on glucose, glucose and a first concentration of galactose, glucose and a second selected concentration of galactose of galactose higher than the first concentration; glucose and a third selected concentration of galactose higher than the second concentration; glucose and a fourth selected concentration of galactose higher than the third concentration; glucose and a fifth selected concentration of galactose higher than the fourth concentration; glucose and a sixth selected concentration of galactose higher than the fifth concentration etc. such that the cells are plated on glucose and plates containing increasing concentrations of galactose.

The supertransactivators can be subdivided into those that affect growth when moderately expressed or alternatively have no apparent effect on growth (e.g. using ADH1 promoter). The present invention also provides evidence that the supertransactivators can act in a dominant fashion over previously identified dominant transactivation defective mutants. Therefore, the supertransactivator can lead to induction of a reporter gene even when it is in the presence of an induction defective p53 where the induction defective p53 would normally prevent induction by wildtype p53. The following table illustrates the effects that a supertransactivating mutation under ADH 1 control, i.e. moderate expression can have:

| | |
|---|---|
| supertransactivator | high induction of reporter |
| supertransactivator + wildtype p53 | high induction of reporter |
| transactivation defective p53 | No induction of reporter |
| transactivation defective p53 + wildtype p53 | low induction of reporter |
| supertransactivator p53 + transactivation defective p53 | high induction of reporter |

These approaches can be applied to p53s that are expressed from promoters other than ADH1 (i.e. different levels of expression).

According to the present method several supertransactivating mutants have been identified. A detailed description of certain examples of the protocol and results for the supertransactivating mutations is provided in the Examples.

The invention further provides a method of detecting a toxic mutation in the human p53 gene comprising: a) obtaining a yeast cell comprising a reporter gene, wherein the reporter gene is linked to a DNA sequence to which a human p53 binds; b) introducing into the yeast cell a nucleic acid which expresses a human p53, the nucleic acid comprising an inducible GAL 1 promoter linked to a human p53 coding sequence; c) plating the yeast cell of step b) on each of glucose, raffinose or galactose and; d) identifying colonies on plates wherein colonies expressing wildtype p53 yield red colonies on glucose plates, red colonies on raffinose plates and white colonies on galactose plates, and wherein colonies expressing a toxic p53 yield red colonies on glucose plates, red colonies or white colonies or no colonies on raffinose plates and no colonies on galactose plates. The toxic mutants may produce white or red colonies at levels of expression where the wild type is red. These mutants are considered supertrans and toxic.

In the method for detecting a toxic mutation, toxic mutants can produce red colonies or white colonies or no colonies on raffinose plates. The toxic mutations may produce white colonies on raffinose that are smaller than the white colonies produced by the wildtype p53 on raffinose.

Alternatively, the method for detecting a toxic mutation can be performed by plating the yeast cell of step b) described above on each of glucose or galactose. If a toxic mutation is present, no colonies will appear on the galactose plates.

The toxic p53 mutations can also be detected by utilizing other promoter systems such as an on-off promoter. For example, the present invention provides a method of detecting a toxic mutation in the human p53 gene comprising: introducing into the yeast cell a nucleic acid which encodes an unidentified human p53 in the cell, the nucleic acid comprising an on-off promoter linked to the human p53 coding sequence; b) incubating the yeast cell in synthetic yeast medium in the presence and absence of an inducer for the promoter; and c) identifying a toxic mutant, wherein yeast expressing wildtype p53 yield growth in the presence or absence of an inducer for the promoter, and wherein yeast expressing a toxic mutation in p53 yields growth in the presence of an inducer for the promoter. An example of an on-off promoter than can be used to detect the toxic mutation include the CUP1 on-off promoter where the induction level is 50-100 fold and the promoter is induced by addition of copper in the medium. If the CUP1 promoter is used, copper acts as the inducer of the promoter linked to the human p53 coding sequence. Similarly, any inducible promoter and inducer of the promoter can be utilized in the methods of the present invention.

According to the present methods several mutations have been identified as toxic. A detailed description of an example of a protocol and results for the toxic p53 mutants is provided in the Examples.

The present invention further provides a method of detecting a toxic suppressor mutation in the human p53 gene wherein a toxic mutation is detected by the method described above and further comprising introducing into a yeast a second nucleic acid, wherein the second nucleic acid expresses a mutant p53, the second nucleic acid comprising a promoter operably linked to a human p53 coding sequence. If the mutation in the second nucleic acid reverses the toxic phenotype, the second nucleic acid contains a toxic suppressor mutation.

Alternatively, a second mutation can be introduced into the nucleic acid containing the toxic mutation detected. This nucleic acid containing both mutations can then be introduced into the yeast cell. If the second mutation in the nucleic acid containing the toxic mutation reverses the toxic phenotype, the second mutation is a toxic suppressor mutation.

The present invention further provides a method of detecting a dominant mutation in the human p53 gene wherein a mutation in p53 is detected and further comprising introducing into the yeast cell a second nucleic acid, the second nucleic acid comprising a promoter operably linked to a wildtype human p53 coding sequence, wherein the second nucleic acid expresses wild-type human p53 in the cell, whereby the mutation is determined to be dominant or recessive. If the phenotype observed is that of the mutation, the mutation is determined to be a dominant mutation.

The present approach provides for direct isolation of p53 variants that can overcome the dominant negative effect on transactivation of the main p53 tumor hotspots. This could be achieved by transforming a strain already expressing a p53 dominant mutant with randomly generated p53 variants and selecting for a wild type phenotype at low level of p53 expression. This would be very useful in the development of p53 alleles to counteract dominant p53 mutations.

The screening methods of the present invention can also be accomplished by utilizing a yeast strain containing a reg1-501 mutation (Hovland et al). This mutation is defective in glucose repression of the GAL promoter so that strains can be grown in standard amounts of glucose and approximately linear increases in the levels of induction are accomplished by adding increasing amounts of galactose. This mutation has been used to control expression levels in yeast of a variety of genes including a heterologous EcoR1 endonuclease (Lewis et al.). The Lewis et al. reference is incorporated herein in its entirety.

For example, the invention provides a method of detecting a supertransactivating mutation in the human p53 gene comprising: obtaining a reg1-501 mutant yeast cell comprising a reporter gene, wherein the reporter gene is linked to a DNA sequence to which human p53 binds; introducing into the yeast cell a nucleic acid which encodes a human p53, the nucleic acid comprising an inducible promoter comprising GAL 1 linked to a human p53 coding sequence; plating the yeast cell on glucose and glucose and increasing concentrations of galactose; identifying colonies on plates, wherein colonies expressing supertransactivating mutation in p53 yield white or pink colonies.

This assay can be performed by separately plating the cells on glucose, glucose and a first selected concentration of galactose, glucose and a second selected concentration of galactose of galactose higher than the first concentration; glucose and a third selected concentration of galactose higher than the second concentration; glucose and a fourth selected concentration of galactose higher than the third concentration; glucose and a fifth selected concentration of galactose higher than the fourth concentration; glucose and a sixth selected concentration of galactose higher than the fifth concentration etc. such that the cells are plated on glucose and plates containing glucose plus increasing concentrations of galactose.

Also provided by this invention is a method of detecting a toxic mutation in the human p53 gene comprising: obtaining a reg1-501 mutant yeast cell comprising a reporter gene, wherein the reporter gene is linked to a DNA sequence to which human p53 binds; introducing into the yeast cell a nucleic acid which encodes an unidentified human p53 in the cell, the nucleic acid comprising an inducible promoter comprising GAL 1 linked to a human p53 coding sequence; plating the yeast cell on each of glucose, or glucose and selected concentrations of galactose; identifying colonies on plates, wherein colonies expressing wild type p53 yield red colonies on glucose, red colonies on glucose and selected concentrations of galactose and white colonies on glucose and higher concentrations of galactose, and wherein colonies expressing a toxic mutation in p53 yield red colonies on glucose, red colonies or white colonies or no colonies on glucose and selected concentrations of galactose, and no colonies on glucose and higher concentrations of galactose.

By utilizing the reg1-501 mutant yeast cell, increases in levels of p53 induction can be controlled by adding increasing concentrations of galactose. One skilled in the art can perform the above-mentioned screening assay by plating the cells on glucose and glucose and selected concentrations of galactose. The selected concentrations can be increasing concentrations of galactose. In doing so, the skilled artisan can vary the concentration of galactose, as necessary, to observe the toxic mutation. For example, the cells can be plated on glucose, glucose and a selected concentration of galactose, and glucose and higher concentrations of galactose. If the skilled artisan observes red colonies on glucose, red or white colonies on glucose and galactose, and no colonies on glucose and higher concentrations of galactose, a toxic mutation has been identified. If the skilled artisan observes, red colonies on glucose, no colonies on glucose and the selected concentration of galactose and no colonies on glucose and higher concentrations of galactose, a toxic mutation has also been identified. However, in order to observe the progression of the toxic effect, the skilled artisan can vary the selected concentration to observe a less toxic effect at lower expression levels of p53. By plating the same toxic mutant on glucose, glucose and a lower selected concentration of galactose, and glucose and higher concentrations of galactose, the skilled artisan can observe the gradual progression of the toxic phenotype, by observing red colonies on glucose, red or white colonies glucose and galactose, and no colonies on glucose and higher concentrations of galactose. The selected concentration can be varied until the skilled artisan discerns which concentration of galactose is sufficient to produce enough p53 such that cell growth can be observed without killing the cells. This assay can be performed by plating the cells on glucose, glucose and a first concentration of galactose, glucose and a second selected concentration of galactose of galactose higher than the first concentration; glucose and a third selected concentration of galactose higher than the second concentration; glucose and a fourth selected concentration of galactose higher than the third concentration; glucose and a fifth selected concentration of galactose higher than the fourth concentration; glucose and a sixth selected concentration of galactose higher than the fifth concentration etc. such that the cells are plated on glucose and glucose plates plus increasing concentrations of galactose.

The invention also provides for the recognition of p53 mutants with reduced transactivation capability, which are referred to as weak p53 mutants, as opposed to normal, suprtransactiviating mutants or nonfunctional mutants. For example, a mutation P250L exhibits low transactivation for promoter 3xRGC and very little transactivation for a BAX promoter when this mutant is expressed at high constitutive levels from an ADH1 promoter. Upon identifying a p53 mutant, either by the screening methods of this invention or via sequencing of mutant p53 identified in tumors, this mutant can be screened for weak transactivating activity by obtaining a yeast cell comprising a reporter gene, wherein the reporter gene is linked to a DNA sequence to which human p53 binds, introducing into the yeast cell a nucleic acid which encodes a human p53, the nucleic acid comprising an constitutive promoter, such as ADH1 linked to a human p53 coding sequence, plating the yeast cell on glucose, and identifying colonies on plates, wherein colonies expressing weak transactivating mutations result in pink colonies when compared to wildtype p53 which produces white colonies under ADH1 constitutive expression. The weak mutations may result in white colonies if expression is higher. The higher level of p53 expression can also be accomplished using the GAL1 promoter and high levels of galactose induction. For example, the GAL 1 promoter can be used such that when induced in the presence of increasing concentrations of galactose, a weak transactivator can be identified because it is unable to transactivate even at high concentrations of galactose, i.e. on glucose plates containing a high concentration of galactose which induce high levels of expression. The DNA sequence to which p53 binds can be 3xRGC, p21, bax or any other sequence to which p53 binds. Other constitutive promoters that can be utilized in the methods of the present invention are also contemplated. These include PGK and the high level GPD system (Vectors for constitutive and inducible gene expression in yeast. Mark Schena, Didier Picard and Keith R. Yamamoto in Guide to Yeast Genetics and Molecular Biology; Methods in Enzymology Edited by Christine Guthrie and Gerald R. Fink; Volume 194 pp 378-398). Any constitutive promoter can be adapted for use in the methods of the present invention.

In the present study standard PCR reactions were chosen to generate p53 variants to decrease the occurrence of multiple mutations in the same PCR fragment. The use of mutagenic PCR conditions could allow the generation of a broader spectrum of "supertrans" alleles. The use of this screen might also lead to a better understanding of the functional properties of p53 mutants observed in some tumor samples.

The present invention further provides a method of screening for compounds that can mimic a toxic p53 by: obtaining a yeast cell comprising a reporter gene, wherein the reporter gene is linked to a DNA sequence to which human p53 binds, introducing into the yeast cell a nucleic acid which encodes a non-toxic mutant or wildtype human p53, the nucleic acid comprising an inducible promoter comprising GAL 1 linked to a human p53 coding sequence, introducing the compound to the yeast cell, plating the yeast cell on each of glucose, raffinose, or galactose, and identifying a compound that mimics a toxic mutation, preventing growth of colonies expressing wildtype or non-toxic mutant p53 to yield red colonies on glucose, red colonies or white colonies or no colonies on raffinose, and no colonies on galactose.

Alternatively, a compound that mimics a toxic mutation can be identified by plating the yeast cell on each of glucose and galactose, wherein a compound that mimics a toxic mutation will result in no growth of colonies in galactose and cells without p53 can grow on galactose.

The detection of compounds that mimic a toxic mutation can also be accomplished through the use of on-off promoter. An example of this would be a method of screening for compounds that can mimic a toxic p53 mutation comprising: a) introducing into the yeast cell a nucleic acid which encodes a non-toxic mutant or wildtype human p53 in the cell, the nucleic acid comprising an on-off promoter linked to a non-toxic mutant or wildtype human p53 coding sequence; b) introducing the compound to the yeast cell; c) incubating the yeast cell in artificial yeast medium in the presence and absence of an inducer for the promoter; and d) identifying a compound that mimics a toxic mutation, thereby preventing growth of yeast in the presence of an inducer for the promoter.

As previously mentioned, a suitable on-off promoter would be the CUP1 promoter which is inducible in the presence of copper. Any inducible promoter can be utilized with the methods of the present invention.

The present invention also provides a method for screening a compound that can mimic a supertransactivating mutation in the human p53 gene comprising: obtaining a yeast cell comprising a reporter gene, wherein the reporter gene is linked to a DNA sequence to which human p53 binds, introducing into the yeast cell a nucleic acid which encodes a wildtype or mutant human p53, the nucleic acid comprising an inducible GAL 1 promoter linked to a human non-supertransactivating mutant or wildtype p53 coding sequence, plating the yeast cell and compound on raffinose, and identifying a compound that mimics a supertransactivating mutation in p53 to yield white or pink colonies, wherein the compound has no effect in the absence of p53.

The yeast cells of this invention can be obtained by generating the yeast strain, purchasing the yeast strain or receiving the yeast strain form any other source. The nucleic acid which encodes human p53 can be introduced by targeted integration into a yeast chromosome or alternatively via methods such as plasmid transformation that results in expression of nucleic acids. The reporter gene of this invention can be stably integrated into the genome of the cell or alternatively, the reporter gene can be introduced via a plasmid that does not contain sequences for stable integration of the reporter gene and results in expression of the reporter gene.

To identify protein-protein interactions between the mutant p53s contemplated in this invention and other proteins, conventional yeast two hybrid assays can be utilized. These procedures employ commercially available kits (e.g., Matchmaker* from Clontech, Palo Alto, Calif.) and involve fusing the "bait" (in this example, all or part of a mutant p53 nucleic acid) to a DNA binding protein, such as GAL4, and fusing the "target" (e.g. a cDNA library) to an activating protein, such as the activation element domain of VP-16. Both constructs are then transformed into yeast cells containing a selectable marker gene under the control of, in this example, a GAL4 binding element. Thus, only those yeast colonies containing cDNAs of proteins or protein fragments that interact with the GAL4-bait constructs will be detected. The cDNA of the target construct is isolated from positive clones and conventional methods used to isolate the cDNA encoding the protein or protein fragment that interacts with the GAL4-bait construct.

Treatment Methods

The invention also provides a method of inducing toxicity in a cell by administering to the cell a human p53 that contains a toxic mutation or a supertransactivating mutation to the cell. The human p53 that contains a toxic mutation to the cell can be selected from the group consisting of V122A, V274I, C277W, C277R, F338L, V157I, or G279R. The human p53 that contains a toxic mutation to the cell can also be a mutant p53 that contains the mutation V122A and the mutation A76T or a mutant p53 that contains the mutation W91C, the mutation C124R, the mutation Q136K, the mutation T150A and the mutation T150A or a mutant p53 that contains the mutation C124R, the mutation Q136K and the mutation T150A. The human p53 that contains a supertransactivating mutation can be selected from the group consisting of S96P, H115R, S121C, S121F, T123A, C124Y, C124F, Q167R, E171K, H178Y, S183L, D184Y, T231I, P191L, S240N, S116T, N288K, F338L, S215T, T123S, N345S, D184G, E198V, T230I, V274A, W91R, H115R, S96P, S1116T, N228K, T118A, T123P, L137R, A159T, M160T, I162V, D184G, N210S, S215T, T230I, I232V, N239Y, N268S, E285A, C124R, Q136K, T150A, A76T.

The invention also provides a method of inducing toxicity in a cell by introducing into the cell a nucleic acid that encodes the toxic mutant p53 linked to a promoter, whereby the toxic mutant p53 is expressed in the cell and causes growth inhibition or cell death. The invention further provides a method of inhibiting growth or inducing toxicity in a cell by introducing into the cell a nucleic acid that encodes the supertransactivating mutant p53 linked to a promoter, whereby the supertransactivating mutant p53 is expressed in the cell and causes cell death or prevent growth. The nucleic acids encoding the toxic mutants or supertransactivating mutants that prevent growth at high expression can comprise a nucleic acid that encodes a mutation selected from the group consisting of: V122A, V274I, C277W, C277R, F338L, V157I, W91C, C124R, Q136K, T150A, or G279R. The nucleic acid that encodes the toxic mutants can comprise a nucleic acid that encodes the mutation V122A and the mutation A76T or a nucleic acid that encodes the mutation W191C, the mutation C124R, the mutation Q136K and the mutation T150A or a nucleic acid that encodes the mutation C124R, the mutation Q136K and the mutation T150A. The nucleic acids encoding the supertransactivating mutants can comprise a nucleic acid that encodes a mutation selected from the group consisting of: S96P, H115R, S121C, S121F, T123A, C124Y, C124F, Q167R, E171K, H178Y, S183L, D184Y, T231I, P191L, S240N, S116T, N288K, F338L, S215T, T123S, N345S, D184G, E198V, T230I, V274A, W91R, H115R, S96P, S116T, N228K, T118A, T123P, L137R, A159T, M160T, I162V, D184G, N210S, S215T, T230I, I232V, N239Y, N268S, E285A, C124R, Q136K, T150A, A76T.

The toxic or the supertransactivating mutations can be used to overcome known tumor mutations or known dominant negative mutations. For example, the toxic or supertransactivating mutations can be used to overcome a mutation present in a cancer patient or a mutation that causes cancer and thereby lead to growth inhibition or lethality of the cancer cells.

As previously described, the nucleic acids of this invention can be utilized in in vivo gene therapy techniques. There are numerous examples in the literature of the administration of p53 to cells (Gallagher and Brown, 1999 Annual Review of Oncology, 10(2) 139-150). The nucleic acids encoding the toxic mutants can be delivered to cells via viral delivery systems, non-viral delivery systems, as naked DNA or liposomes. Examples of viral delivery include retroviral delivery in which viral vectors integrate stably into the genome of the infected cells and require cell division for transduction. Retroviral vectors are used in the majority of approved gene transfer clinical protocols (Roth and Cristiano, 1997 J. Natl. Cancer Inst., 89:21-39).

Another viral delivery method that has been utilized in p53 replacement therapy is the adenoviral delivery method (Roth and Cristiano), based on adenovirus type 5. In addition to adenovirus type 5, other adenoviruses can be utilized such as AAV1, AAV2, AAV3, AAV4, and AAV6. Adenoviruses are capable of high efficiency transduction of a wide range of cells types and are not limited to actively proliferating cells. Since adenoviruses do not integrate into the genome of the host cell, they are transient expression vectors and therefore do not carry the same risk to causing insertional mutagenesis as in retroviral transduction. Since the expression is transient, delivery of toxic mutant p53 to cells can be achieved that result in cell death or irreversible growth arrest without the possibility of continued expression of the toxic mutant that may be deleterious to the organism.

Other viral vectors such as the herpes simplex virus (HSV) can be utilized for gene therapy as well. There are reports in the literature of utilization of HSV for gene therapy of brain tumors (McKie et al. 1996 British Journal of Cancer, 74:745-752) and the HSV protin VP22 alone was sufficient to mediate intercellular delivery of functional p53 protein, formulated as a fusion protein with the virion protein (Phelan et al. 1998: Nature Biotechnology 16: 440-443.

Non-viral delivery methods include direct DNA injection and cationic lipid mediated gene transfer. Phase I clinical trials have employed direct percutaneous intratumour injection of DNA, more specifically, naked (i.e. without viral or synthetic vector) wildtype p53 into patients having either primary or secondary liver tumors (Habib et al. 1996 Cancer Detection and Prevention 20:103-107; Fricker J. 1996 Molec. Med. Today 2: 361; Habib N A. 1997 4: 329-330).

Cationic lipid mediated delivery involves the use of cationic liposomes complexed with plasmid DNA carrying the transgene of interest which can be efficiently endocytosed by mammalian cells. Cationic delivery is relatively non-toxic and perhaps non-immunogenic which would allow multiple administrations of the mutant p53s, which may be necessary in the treatment of metastatic tumours. Studies in which liposome-p53 complexes were directly injected into human breast tumors grown on nude mice caused not only regression of the primary tumour but also prevention of tumour relapse and metastasis (Nu et al. 1997 Human Gene Therapy 8: 177-185).

The present invention further provides a method of inducing toxicity in a cell by administering a toxic human p53, or a nucleic acid encoding a toxic p53 further comprising administering an anticancer therapy. Anti-cancer therapy can include surgery, chemotherapy, radiotherapy, immunotherapy or any combination thereof. Examples of chemotherapeutic agents include cisplatin, 5-fluorouracil and S-1. Immunotherapeutics methods include administration of interleukin-2 and interferon-α.

The present invention is more particularly described in the following examples which are intended as illustrative only since numerous modifications and variations therein will be apparent to those skilled in the art.

EXAMPLES

Toxic Mutants

Yeast Strains, Plasmids, Media and Reagents

The haploid S. cerevisiae strain yIG397 (Mata ade2-1 leu2-3, 112 trp1-1 his3-11,15 can1-100 ura3-1 URA3 3xRGC::CYC1::ADE2) was originally constructed to assess p53 transactivation by Richard Iggo (Flaman et al). The strain contains an integrated copy of ADE2 under control of a minimal CYC1 promoter. 3 copies of the human p53 responsive DNA element found at the ribosomal gene cluster (RGC) are inserted in the upstream region of the promoter. Thus, ADE2 is under p53 transcriptional control and transactivation by p53 alleles can be easily scored based on the color of yeast transformants on suitable plates. Colonies expressing wild type p53 grow like adenine prototrophs yielding white colonies on plates containing a limiting amount of adenine while small red colonies appear when a nonfunctional p53 is expressed. Strains T334 (Sclafani) and S1 (Tran et al.,) were used in some experiments to test the effect of p53 on growth and to obtained diploids by crossing them with yIG397 derivatives. The haploid strains, YPH-p21 (MATα ura3-52 lys2-801 ade2-101 trp1-Δ63 his3-Δ 200 leu2-Δ 1 URA3p21::pCYC1::ADE2) (p21 p53 binding site is a 20 mer sequence found 2.4 kb upstream of the p21 promoter), and YPH-bax (MAT α ura3-52 lys2-801 ade2-101 trp1-Δ 63 his3-Δ 200 leu2-Δ 1 URA3 bax::pCYC1::ADE2) (bax p53 binding site is a 39mer sequence found 486-448 bp upstream of the bax promoter) were also utilized in the present invention. They allow the evaluation of p53 transactivation function as in yIG397, but the p53 responsive element controlling ADE2 transcription has been changed into the p21 and bax promoter elements, respectively (Flaman et al.).

Plasmid pLS76 encodes the complete human p53 cDNA under the control of the constitutive ADH1 promoter. The plasmid is based on pRS315 (LEU2). pLS89 is a yeast expression vector coding for the p53 cDNA under control of the strong inducible GAL1 promoter. Plasmid pRDI22-identical to pLS76 except for the BsmI::StuI deletion at p53-and pLS89 (after BsmI::StuI digestion and gel purification) were used for gap repair cloning, as previously described (Flaman et al). Briefly, PCR amplifications of a p53 cDNA fragment between positions 124 and 1122 were co-transformed in yIG397 together with the linear gapped plasmid. Since both ends of the PCR product and of the linear plasmid overlaps (75 and 80 bp, respectively at the 5' and the 3') in vivo homologous recombination can reconstitute the complete p53 cDNA and a circular expression vector.

Plasmids pCMV-Neo-Bam and pC53-SN3 (Baker et al., (1990) "Suppression of human colorectal carcinoma cell growth by wild type p53". Science 249: 912-915) coding for the human p53 cDNA under CMV promoter were used for expression studies in mammalian cells. Specific mutant p53s were constructed replacing the SgraI-StuI p53 portion with the same fragment of pLS89 derivatives. The plasmid PG13 contains 13 copies of a p53 responsive element that allow the p53 transcriptional control of the luciferase gene. The plasmid MG15 is a control vector with mutated copies of the p53 binding site (Kern et al.,). PG13 and MG15 were used to test p53 transactivation in mammalian cells. Plasmids pGL1012 and 1138 contain respectively the bax responsive element and a 2.4 kb region from the p21 promoter and the luciferase gene.

Yeast strains were cultured in (1% yeast extract, 2% peptone, 2% dextrose (YPD) or with the addition of 200 mg/l adenine (YPDA) or on selective medium when appropriate. p53 transactivation was generally determined in synthetic medium containing 5 mg/l of adenine. Growth inhibition was analyzed in plates containing galactose at 2% as a carbon source (YPGAL). To determine the transcriptional potential of the p53 toxic allele, plates containing raffinose at 2% (Sigma) as a carbon source and variable low amount of galactose were used. In the presence of raffinose the GAL1 promoter is derepressed and can be induced by galactose addition.

Random Mutagenesis Experiments, PCR Integration in Yeast, DNA Recovery and Analysis Plasmid pLS89 was used as a template for PCR reactions using the TAQ Long Plus polymerase mix (Stratagene) under optimal reaction conditions. Universal primers pRSa and pRSc were used to generate a 5 kb fragment that included the sequence for the p53 cDNA, its GAL1 promoter and the yeast selection marker TRP1. The primers also had 50 bp tails corresponding to LYS2 sequence to allow specific chromosomal integration of the fragment. PCR reactions were purified by precipitation and used to transform yIG397 competent cells by the LiAc protocol. Transformants were selected on synthetic medium lacking tryptophan and tested for lysine auxotrophy. Purified TRP1-lys2 clones were then tested on galactose plates with low adenine to test p53 dependent growth inhibition and transactivation.

Genomic DNA was prepared by standard methods and the p53 fragment between 124 and 1122 was PCR amplified, cloned using gap repair in pLS89 to confirm the phenotype in yeast, and sequenced using an ABI373 automated sequencer.

Western Blots yIG397 derivatives with integrated p53, or transformants with p53 expression plasmids, were cultured overnight in selective glucose medium. Cells were washed and diluted in galactose-containing medium to induce the GAL1 promoter. Aliquots were collected at various times. Protein extracts were prepared in lysis buffer (100 mM NaPhosphate pH 7.0; 1 mM EDTA; 0.1% SDS; 1× protease inhibitor cocktail, Roche) with the aid of sterile acid-washed glass beads (0.45-0.6 mm). Protein concentration was measured by the Bradford assay (Biorad) according to the standard protocol. Precast SDS-PAGE gels (PAGE-ONE, Owl Separation Systems) were used for electrophoresis. Proteins were transferred to PVDF membrane (Immobilon-P, Millipore) using a semi-dry electroblotter (Owl Separation Systems) according to instructions. p53 was detected by using both pAb1801 and DO-1 monoclonal antibodies (Santa Cruz) at 1:2000 dilution. Immunodetection was performed using the ECL kit (Amersham) according to protocol.

Transfections in Saos-2 Cells, Luciferase Assays and Western Blots

The osteosarcoma derived p53 null cell line SAOS-2 was used for p53 expression experiments. Cells were cultured in McCoy's 5A medium with 15% FBS serum (GIBCO). T25 cm$^2$ cell cultures flasks were seeded and transfected at 60% confluence by lipofectin reagent (GIBCO). For stable transfections, 1.5 g of purified plasmid DNA was used. Selection by G418 (GIBCO) at 0.5 mg/ml was applied after one day of recovery in complete medium following removal of lipofectin. Colonies were stained after 2-3 weeks.

p53 transactivation assays in transient transfections were done using 50 to 100 ng of p53 expression plasmid and 1.5 g of PG13 or MG15. Cells were recovered, lysed and protein extracts were quantified. Luciferase activity was measured by scintillation counting using the single photon monitor program using the Luciferase Assay System (Promega). The same or similarly obtained protein extracts were used for Western blot analysis. p21 was detected using c-19 monoclonal antibody (Santa Cruz).-tubulin was used as an internal loading and transfer control and detected by a monoclonal antibody (Sigma)

Wild Type and Mutant p53's Under GAL1 Control: Identification of a Toxic p53 Mutant The expression of p53 in yeast can result in reduced growth when highly expressed. This invention sought to identify p53 mutants that could enhance this phenotype, even under conditions of reduced expression. To do this, p53 mutants were generated using mutagenic PCR methods. The complete human p53 cDNA was amplified along with a GAL1 promoter and yeast DNA regions that would allow for targeted integration into a yeast chromosome. The p53 fragment was integrated into a chromosome (at the LYS2 locus) rather than being recovered on a plasmid because overexpression of p53 leads to plasmid loss. Conditions in which approximately 15% of the recovered p53 genes would exhibit reduced transactivation (i.e. less than an average of one detectable mutation per gene) were used.

Figure 1:
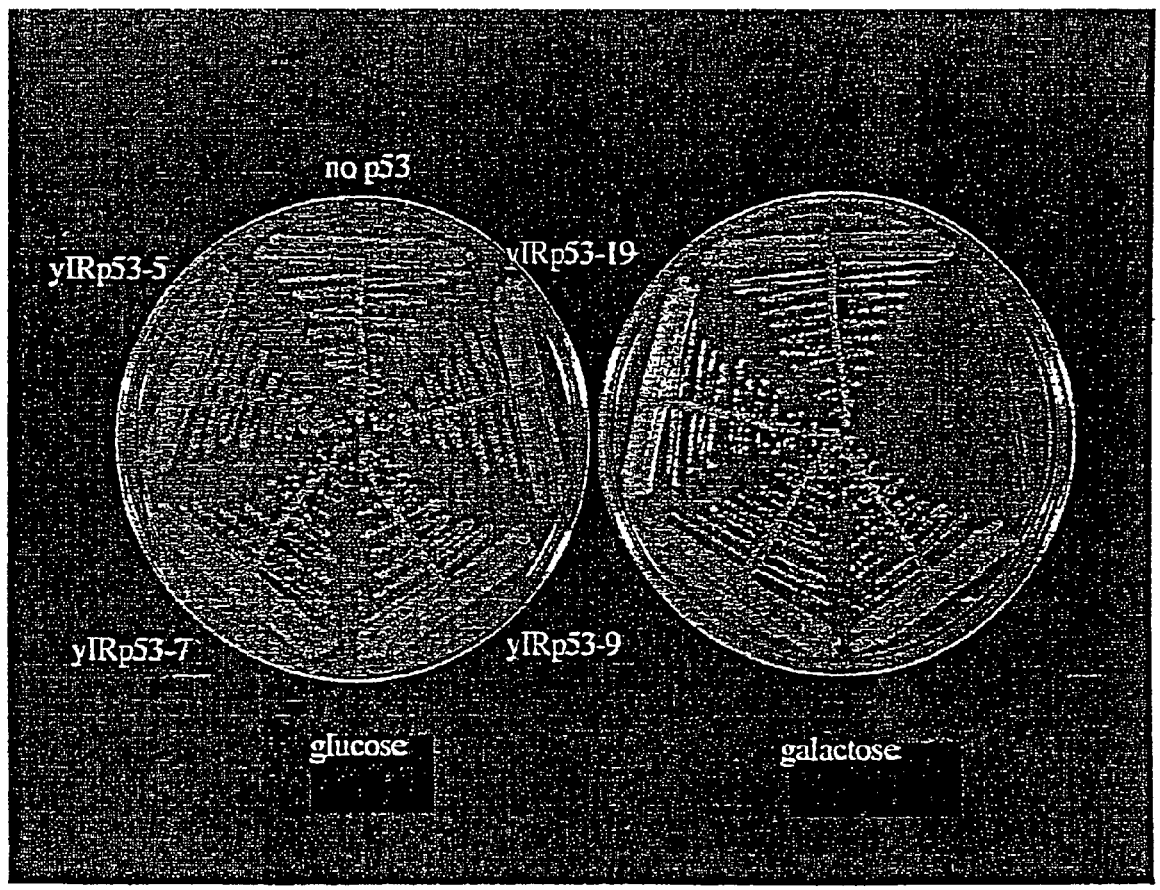
FIG. 1. Phenotypic analysis of p53 alleles integrated in yeast. Transformants of yIG397 that had p53 or mutant p53 under GAL1 control integrated into the LYS2 were streaked onto YPD and YPGAL plates and incubated at 30° C. for three days. Clone yIRp53-5 shows the wild-type p53 phenotype in that it becomes white on galactose due to the ability of p53 to transcriptionally activate the promoter next to the ADE2 reporter gene. Clones 7 and 9 behave like p53 mutants (red colonies and very limited growth delay). Clone yIRp53-19 cannot grow on galactose.

Most of the transformants examined gave rise to small white colonies when cells were plated to rich medium containing galactose (and a small amount of adenine) consistent with induction of wild type p53. Larger red colonies were observed in about 10% of the clones. Those isolates may have been expressing a mutant p53 or possibly had no p53 cDNA. A small number of isolates (about 1 per 1000 transformants) did not give rise to colonies when plated to medium containing galactose as the only carbon source. These latter clones exhibited growth when cells were transferred to raffinose medium, which allows for a low level of induction of the GAL1 promoter. Addition of galactose to the raffinose medium also resulted in a no-growth phenotype. One of these isolates (yIRp53-19, FIG. 1) was examined further.

Figure 2:
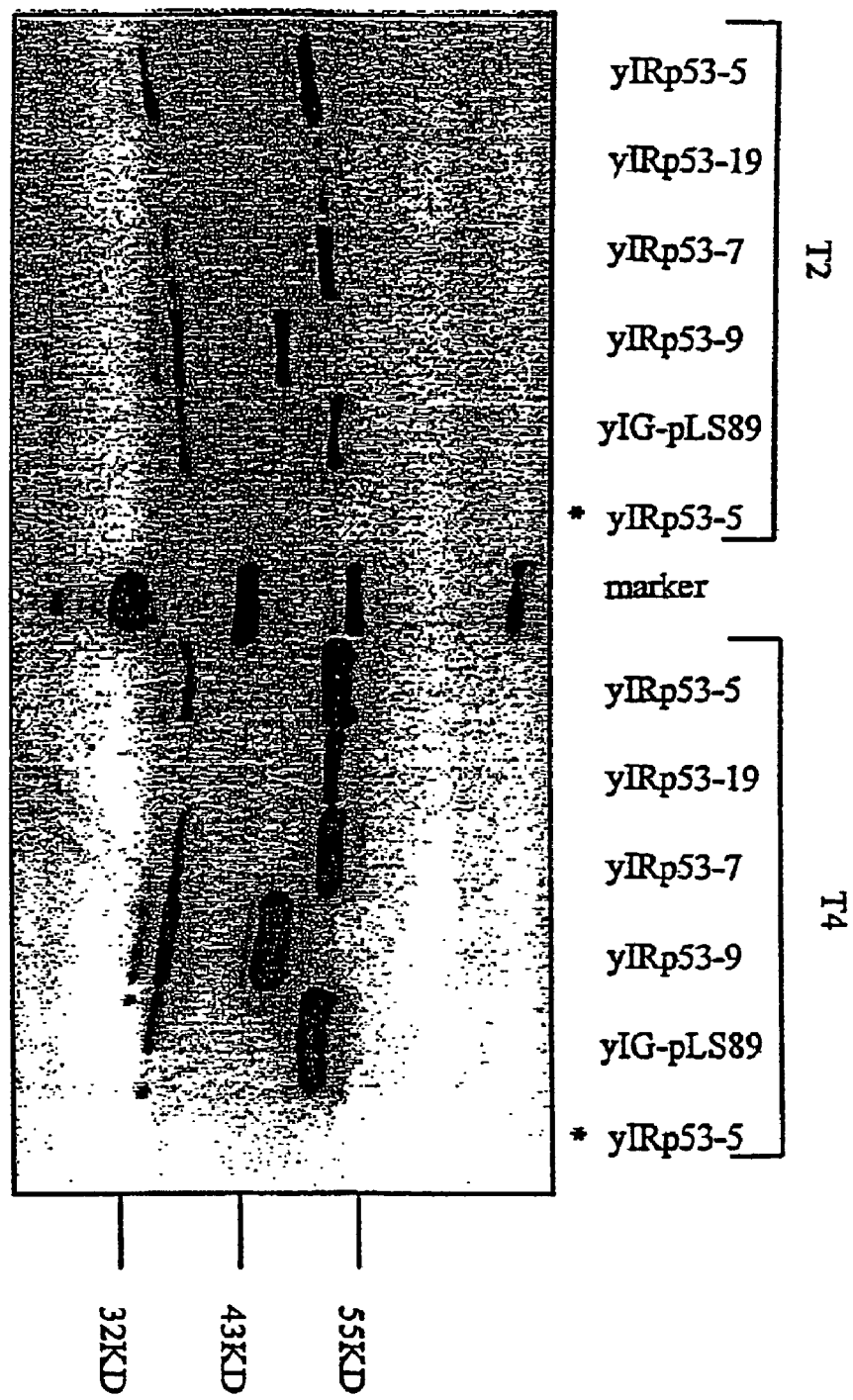
FIG. 2. The toxic p53 protein is full length and has a slightly reduced expression compared to wild type p53. Cells containing the toxic mutant p53 were incubated in galactose medium and extracts were prepared two or four hours later. 20 g of protein extract were loaded per lane. p53 was detected using antibodies pAb1801 and DO-1 (Santa Cruz). YIRp53-5, 7 and 19 showed full size p53 whereas p53 was truncated in clone-9. The lower bands are likely due to degradation since there is much less material in extracts obtained from a protease deficient strain.

Southern analysis revealed that the no-growth p53 mutant (yIRp53-19) was integrated correctly into the LYS2 locus. Induction of p53 was also normal. This mutant along with two other transactivation deficient mutants (yIRp53-7 and -9), a wild type isolate (yIRp53-5), and a clone expressing wild type p53 from a pLS89 plasmid were grown in galactose for two or four hours and p53 protein levels were determined by western blotting using a combination of p53 monoclonal antibodies (FIG. 2). yIRp53-19 showed a full length p53 but its expression level was slightly reduced. This may be related to the toxic effect of the protein. This result suggests that the lack of growth was not due to excessive induction of p53. In addition, the degradation bands that were visible in overexposed films were also comparable between strains suggesting that differences in protein stability were not responsible for the lack of growth. The degradation is not due to the extraction procedure since it is markedly reduced in extracts obtained from a protease deficient strain.

It is unlikely that the integration process generated a mutation in the yeast genome that might prevent growth when galactose was used as carbon source. To check this, yIRp53-19 was crossed with another strain. Similar to the haploids, diploid cells failed to grow on galactose. However, unlike the original haploid clone, revertants were frequent, consistent with an opportunity for homozygosis of the LYS2 gene (i.e., loss of the deleterious p53 mutation).

The region of p53 gene in the yIRp53-19 isolate between nucleotides 124 and 1122 was amplified by PCR from genomic DNA. Gap repair into yIG397 cells was then used to reconstitute GAL1 p53 expression plasmids containing the PCR sequence. Transformants were selected on glucose. No growth was observed on galactose plates after 5 days, whereas cells with wild type p53 on a plasmid did exhibit growth. Thus it was concluded that the p53 fragment amplified by PCR was responsible for the no-growth phenotype. However, when examined under the microscope cells underwent a small number of divisions on galactose compared to the original isolate and gave rise to irregular microcolonies containing approximately 50-100 cells. This phenotype was likely due to plasmid instability and possibly cross-feeding.

Figure 3:
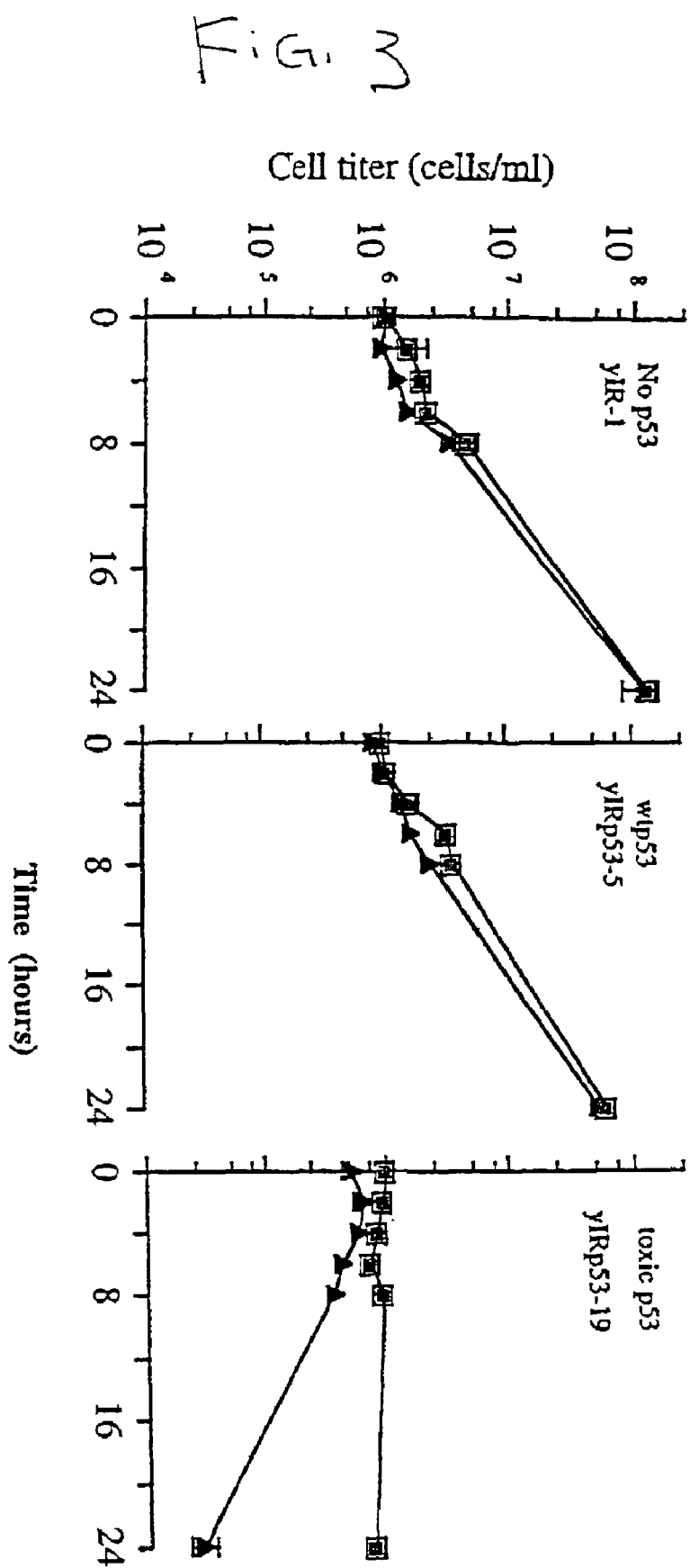
FIG. 3. Lethal effects of expressed mutant p53. Clones yIRp53-5, yIRp53-19 and the parental strain lacking a p53 integrant were grown overnight in glucose medium, washed and diluted to $10^6$ cells/ml and grown in galactose medium for 24 hours. Aliquots were taken at the indicated times, titers were determined, and cells were plated to glucose to assess viability. The curves identify the mean and standard errors for a triplicate set of experiments. Squares correspond to cell number; triangles correspond to viability.

Expression of the No-Growth p53 Allele yIRp53-19 Prevents Cell Division and Results in Lethality In order to determine if induction of p53 resulted simply in growth arrest or alternatively in cell death, survival under conditions of galactose induction was determined. Cells containing the integrated yIRp53-19 were grown on galactose and plated to glucose plates at various times to repress the induction of p53. In the first 24 hours, the wild type p53 cells (yIRp53-5) showed a modest growth inhibition compared to the control strain without p53 and a high plating efficiency on glucose (FIG. 3). On the contrary, yIRp53-19 cells showed no increase in cell titer and a clear reduction in the absolute number of viable cells (FIG. 3). After 24 hours of incubation in galactose only 7% of the cells gave rise to colonies.

Cell growth and division on galactose medium were also examined microscopically. Cells from freshly grown colonies on glucose were suspended in water, washed, briefly sonicated and plated on galactose plates. Cell division and colony formation was observed using a Singer microscope system and pictures were taken at various times after plating. Cells expressing wild type p53 underwent 2-3 divisions in 10 hours and eventually formed small colonies, characteristic of the inhibitory effect of over-expressed p53. This contrasted with the yIG53-19 cells. Most of the cells did not divide although they increased in size. There was no distinctive terminal arrest phenotype. A few cells showed bud emergence at 10 hours, but no further division was observed. These results indicated that the inducible expression system had isolated a toxic mutant of the p53 gene.

The Toxic Mutation p53-19 Lacks Transactivation

To examine the ability of yIRp53-19 to transactivate a standard reporter system, expression of p53 was greatly reduced in order to prevent lethality. Cells were grown on plates containing 2% raffinose as a carbon source and a small amount of galactose (0.006% and 0.015%) and limiting adenine. This would allow for growth and provide the opportunity to detect possible transactivation function, based on the color of the colonies that would arise. Under these conditions, the wild type p53 of yIRp53-5 clone led to transcription of the ADE2 reporter gene as evidenced by the appearance of white colonies. Only red colonies were observed with yIRp53-19. Thus, it appears that p53-19 alters the transactivation ability of p53 at a promoter containing a ribosomal gene cluster (RGC) responsive element. (As noted below, the p53-19 mutant does retain some transactivation capabilities based on results in human cells).

DNA sequencing of the region from nucleotide 124 to 1122 of p53-19 revealed two base pair substitutions, a T to C at position 365 and an A to G at position 887 resulting in the following amino acid changes: V122A and H296R. In order to identify whether the phenotype was due to a single change or to the combination, the mutations were tested separately. The corresponding regions were PCR amplified and cloned by gap repair into a GAL1 expression plasmid (see above). When cells were incubated on galactose, expression of the H296R mutant resulted in reduced growth as found for expressed wild type p53. However, the p53-V122A mutant totally prevented growth, similar to the phenotype of the original isolate. To ascertain whether the observed phenotype was strain dependent, the effect of p53-V122A expression was tested in three different strain backgrounds (one was protease deficient) and comparable results were obtained.

The impact of the individual p53-V122A and p53-H296R mutations were investigated further by cloning them into a plasmid containing the ADH1 constitutive promoter. This leads to a moderate level of p53 expression and no growth inhibition by wild type p53. H296R exhibited normal transactivation of the ADE2 reporter (the transformants were white) and no growth inhibition. Attempts to clone the p53-V122A region by gap repair did not yield any normal size colonies. Instead, only micro-colonies were visible that could be detected after 4-5 days of incubation. As an alternative approach a plasmid was constructed in which the p53 V122A gene was placed under the control of the ADH1 promoter. Transformation by this plasmid resulted in only microcolonies containing less than 50 cells, many of which were enlarged, after 4-5 days. The ability to undergo transformation was not affected since the frequency of these microcolonies was comparable to the frequency of normal colonies obtained with a control plasmid. Thus, the p53-V122A mutant is toxic in yeast even under moderate expression.

The p53 V122A Toxic Mutation is Dominant Over Wild Type p53.

Interactions and dominance of the V122A mutant protein with wild type and other p53 mutant proteins were examined. Transformants were generated containing pairs of differentially marked GAL1 expression plasmids. The following p53 functional mutations as well as wild type p53 were tested in combination with V122A: P151S, P152L, P177H, R213Stop, S241F, C242Y, G279E, Q331Stop. Co-expression of V122A with wild type p53 also resulted in the no-growth phenotype. The two truncations, which could not form tetramers, did not relieve the V122A toxicity. All the missense mutations, which are defective in transactivation, provided only a small relief from the V122A toxic effect. When these mutant proteins are expressed on their own, they have little effect on growth. (Table 1).

While reduced growth was observed, suggesting dominance of the V122A mutation, it is also possible that sufficient homotetramers of the toxic 53 protein are formed to prevent growth. In order to reduce the amount of p53 protein, transformants were generated containing p53 under the control of the ADH1 promoter. The V122A toxicity was dominant over the wild type p53 in that transformants containing both expression plasmids could not be recovered. However, the two DNA binding mutants P177H and G279E relieved V122A toxicity, allowing the appearance of slightly irregular red colonies. This indicates that interactions with defective protein can counteract the toxic effect of V122A (Table 1). This along with the results with the wild type p53 indicates that the toxic effect of V122A requires DNA binding and that this can occur when the protein is a homotetramer or when associated with normal DNA binding p53 protein.

Second Site DNA Binding Mutations Can Relieve V122A Toxicity

Second site mutations were introduced into the p53 V122A allele in order to examine the importance of DNA binding and transactivation on its toxic impact. The double mutants were cloned into the high expression GAL1 plasmid or the moderate expression ADH1 plasmid. A double mutation formed with the Q331 Stop mutation resulted in alleviation of much of the growth defect when expression was from the GAL1 promoter. All the double mutants formed between V122A and P177H, M246L, E258K, G279E, R282Q reduced the toxic effect of V122A when expressed from the GAL1 promoter (Table 2). There was no inhibition with the reduced expression from the ADH1 promoter. These transactivation mutations do not inhibit growth when expressed on their own. The double mutants with P177H and G279E exhibited colony growth comparable to that observed with wild type p53. These colonies were red, demonstrating that the double mutant proteins could not transactivate the ADE2 reporter. Even the double mutant V122A::R282Q which greatly reduced colony growth (compared to wild type p53) also yielded red microcolonies. We conclude that the V122A mutation causes growth inhibition even when combined in cis with other transactivation mutations. Also it does not restore transactivation to other known transactivation mutants.

Identification of Additional p53 Mutants Toxic to Yeast

Given that the toxic effect could also be seen when the mutant was expressed from a low-copy centromere plasmid in yIG397 cells, the search for toxic p53 mutants was expanded by cloning PCR products corresponding to the p53 cDNA region between nucleotides 124 and 1122 (amino acid 42 to 374) into a centromere plasmid using gap repair. Among 5000 transformants, 5 isolates were identified that exhibited a "no-growth" phenotype when highly expressed from the GAL1 promoter and these are presented in Table 3. Similar to the V122A mutant, attempts to place the growth inhibitory p53 mutant genes under the control of the moderately-expressing constitutive ADH1 promoter (i.e., gap repair into plasmid pRDI-22) were unsuccessful. Thus, these mutant p53s clones are also toxic to yeast.

Clones 2 and 3 contained the V122A mutation. The mutant clone 4 contained two mutations, one at codon 274 and the other at 277. Even though p53 missense mutations have been found in vivo at both codons, the V274I amino acid change appears only twice in the p53 tumor database and C277W is novel. Mutant clone 5 also contained two base pair substitutions resulting in amino acid changes at codon 277 in the DNA binding domain (C277R) and codon 338 in the tetramerization domain (F338L). Both changes are novel in the p53 tumor database, but C277R has been previously described as affecting in vitro and in vivo DNA binding specificity (Thukral et al.; Saller et al.). The mutant clone 6 had a single base pair substitution resulting in the G279R amino acid change. Codon 279 mutations have been identified in tumors and there are 6 cases of the G279R amino acid change in the p53 tumor database. In other studies, it was found that a G279E change is a transactivation mutant that has almost no effect on growth when over-expressed from a galactose inducible promoter.

The two amino acid changes in clone 5 (C277R and F338L) were examined further. Centromere plasmids that contained the individual mutant p53s under GAL1 promoter control were constructed. Expression of the C277R mutant on galactose resulted in growth inhibition nearly equal to that of the double mutant. The over-expression of F338L mutant was phenotypically similar to that of wild type p53 (white colonies and modest growth inhibition).

Transactivation Capability of Toxic p53 Mutants on Various Response Elements

Figure 4:
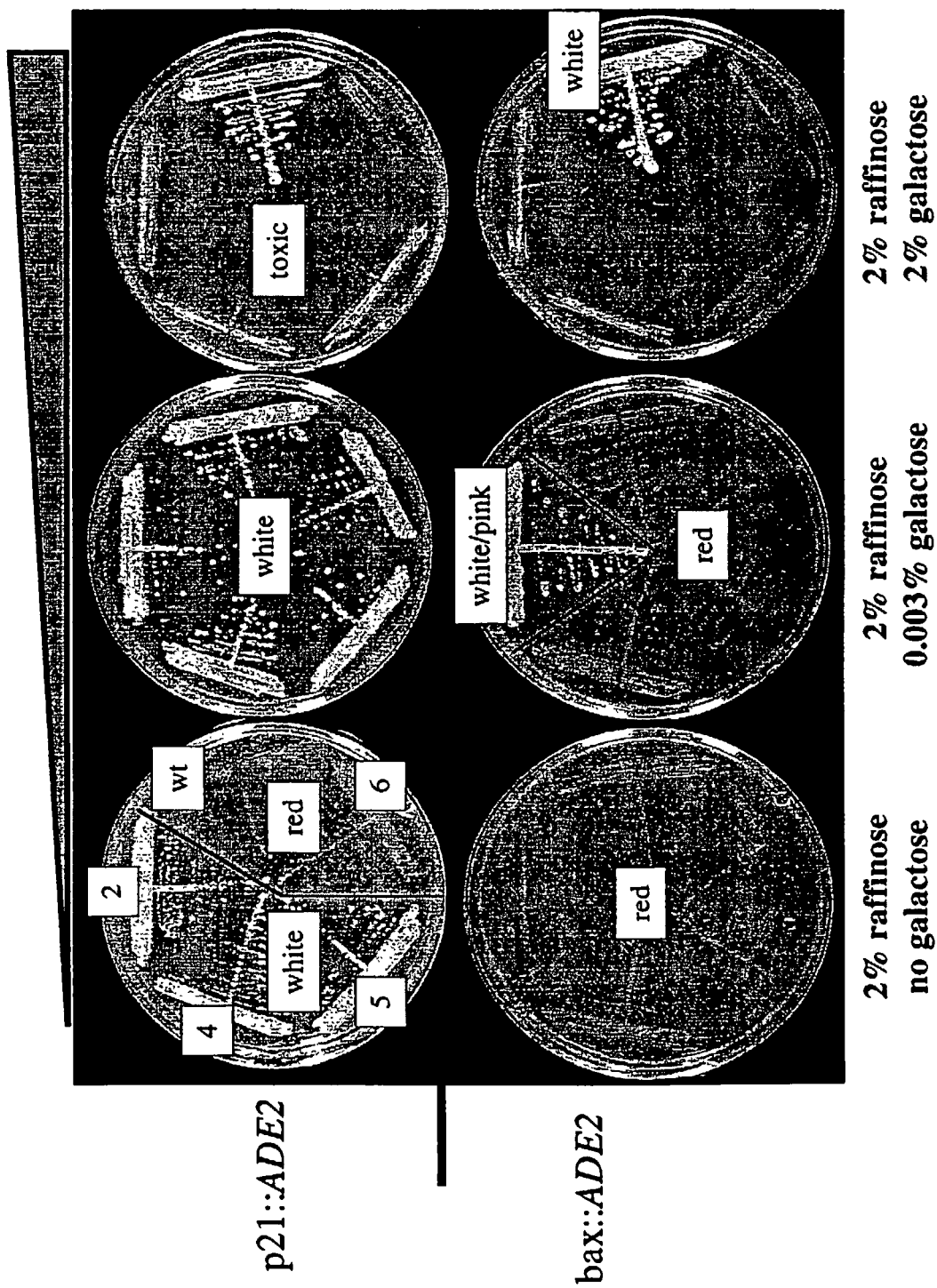
FIG. 4. Evaluation of the transactivation capabilities of toxic p53 mutants in yPH-bax and yPH-p21 strains.

None of the toxic mutants could activate transcription of an artificial minimal yeast promoter containing three copies of the RGC responsive element when expressed at low non-toxic levels. This result contrasts with the observation of a direct link between DNA binding, transactivation and growth inhibition/toxicity. The possibility that the recovered toxic alleles possess altered sequence recognition was examined. For example, they might exhibit a defect in transactivation for some promoter elements but show wild type or even enhanced activity for others. The toxic p53 alleles were expressed under the control of the GAL1 promoter in strains containing p21::ADE2 or bax::ADE2 reporters. As observed in yIG397, moderate to high level of expression of all mutants was toxic. In order to evaluate transactivation, transformants with GAL1 expression plasmids were plated on selective media containing low adenine and raffinose as unique carbon source or raffinose and variable amount of galactose (FIG. 4). Glucose plates with low adenine and raffinose plates without adenine were used to check that transactivation actually reflected protein expression and that white/pink colonies were phenotypically adenine prototrophs. Surprisingly, in yPH-p21, all toxic p53 alleles, except p53-G279R, activated transcription on raffinose plates. These mutants were considered supertrans for p21, since there was no activation by wild type p53 at the same low expression. p53-G279R can also activate transcription but at higher level of protein expression (raffinose+0.003% galactose) and is not distinguishable from wild-type p53. At much higher levels of expression ($\geq 0.5\%$ galactose) growth was completely suppressed by all the toxic mutants.

The toxic mutants were also examined for their ability to transactivate the bax::ADE2 reporter. Unlike for p21, none of the mutants exhibited activation of ADE2 under conditions of low expression (on raffinose only). However, in the presence of a small amount of galactose (0.003%) the p53-V122A mutant gave rise to light pink colonies, while the wild type as well as the other mutants only gave rise to red colonies. At a much higher level of expression the wild type p53 yielded white colonies.

The present invention shows that subtle differences in transactivation capabilities between the various toxic mutants can be characterized using three different p53 responsive elements (RGC, p21 and bax) and variable expression of p53. While toxic at high levels of expression, the p53 alleles exhibit promoter selectivity and enhanced transactivation for some p53 responsive elements. It also appears that the difference in relative DNA binding affinity of wild type p53 for the bax and p21 responsive elements observed in vitro (Wieczorek et al.) and with human cells (Ludwig et al.; Thornborrow et al.) is recapitulated in this yeast system using conditions of low protein expression.

Intragenic Suppression of p53 Tumor Mutants for p21 and Bax Transactivation by p53-V122A Since p53-V122A exhibited enhanced transactivation of a minimal yeast promoter containing either the p21 or the bax responsive elements, this amino acid change might be expected to counteract p53 tumor mutations elsewhere in the DNA binding domain that cause a loss of transactivation. Several double mutants were expressed under the GAL1 promoter at high level of expression in the yPH-p21 and yPH-bax strains. Only the double mutants p53-V122A::P252L and p53-V122A::R282Q could transactivate the bax::ADE2 reporter; they also exhibited a small colony phenotype. On the contrary, several double mutants produced white or pink colonies in yPH-p21 (Table 4), consistent with the supertrans nature of V122A p53 toward the p21 response element. Surprisingly, the truncated p53-V122A::Q331Stop also produced pink colonies. The relative binding affinity of p53 for the p21 and bax responsive elements may explain the different ability to reactivate various p53 mutations. In light of the transactivation results in yPH strains, the observation that p53-V122A retains growth inhibition when overexpressed in combination with p53 tumor mutants suggests that this allele may tolerate dominant-negative p53 mutants in mixed tetramers and retain DNA binding and transactivation function.

Expression of p53-V122A Prevents Growth of Human Cells.

The unusual phenotype of p53-V122A in yeast led us to investigate whether this novel p53 mutant might result in a similar phenotype in mammalian cells. The consequences of expression in transient and in stable transfections of the human p53-null cell line SAOS-2 were examined. A series of expression vectors based on plasmid pC53-SN3 (reference) were constructed for the expression of the V122A allele and other mutations. A truncated monomeric form (V122A::Q331 Stop) and two double mutants (V122A::G279E; V122A::R282Q) were included in the analysis. Cells were transfected using standard procedures and p53 expression was confirmed by Western blots (see FIG. 6).

Growth suppression by the p53 V122A plasmid was high and comparable to that with the wild type p53 (FIG. 5). The monomeric derivative (V122A::Q331 stop) did not exhibit growth suppression, suggesting that the V122A impact required tetramerization. Interestingly, the double mutant V122A::G279E caused inhibition of colony formation to a level close to that of wild-type p53, while the G279E mutation on its own did not significantly reduce colony formation as compared to the control plasmid. Thus, similar to results in yeast, a defect in transactivation (due to the G279E change) does not suppress, but only slightly reduces the V122A impact on growth. The p53 tumor mutant R282Q and the double mutant V122A::R282Q were also examined in the growth suppression assay. R282Q was previously shown to retain partial function as judged by the ability to induce p21. Consistent with that observation, the R282Q mutant exhibited high growth suppression. The double mutant V122A::R282Q and R282Q alone conferred comparable growth suppression (FIG. 5).

The ability of p53V122A to act in a dominant fashion was also examined by co-transfection with a large excess (ratio of 1:4) of various mutant p53 proteins. Neither the V122A mutant nor wild type p53 showed a significant dominant effect over G279E and R282Q.

The similarity between the wild type and the p53 V122A proteins in mammalian cells led to further investigation as to whether they act similarly on induction of the p21 gene (FIG. 6). The wild type p53 led to considerable induction of p21. The p53-V122A mutant exhibited much less induction. As expected the G279E mutant alone resulted in almost no induction of p21 and a similar result was obtained with the V122A::G279E mutant. It should be pointed out that this double mutant led to high growth suppression as noted above (see FIG. 5 and Table 5). Thus, the p53-V122A mutant differs considerably from the wild type protein in ability to induce the p21 target gene. A moderate level of p21 was induced by the R282Q mutant protein, while the double mutant V122A::R282Q showed a reduced induction (FIG. 6). This result suggests that V122A is at least partially defective in transcriptional activation in Saos-2 cells and that it suppresses cellular growth on its own, or in double mutants, in a p21 independent fashion.

The transactivation potential of p53-V122A was also tested using plasmid-based luciferase reporter assays. Saos-2 cells were co-transfected with both the luciferase reporters and the p53 expression plasmids and protein extracts were prepared 24 hours after transfection. When tested with the p21 promoter, p53-V122A exhibited a wild type activity and the double mutant p53-V122A::G279E was not re-activated (FIG. 7, panel A). However, p53-V122A induced luciferase at a higher level compared to wild type p53 with the bax responsive element (FIG. 7, panel B). This effect is not due to a difference in p53 expression, as the western blots showed similar or somewhat reduced p53 protein for the V122A allele. Surprisingly, p53-V122A was as effective as wild type p53 in inducing luciferase activity with PG13 (13xRGC-RE::luc) (FIG. 7, panel C). Moreover, while p53-G279E was inactive in this assay, p53-V122A::G279E was active. p53-V122A and the double mutant with G279E were as active as wild type when tested with a MDM2::luciferase reporter system.

A summary of comparisons between results of various toxic and supertrans mutants in yeast and human cells is presented in Table 5. There is a general correlation between responses in yeast and mammalian cells, especially given the differences between the response elements when placed in yeast and in human cells and differences in expression systems.

Lethal Impact of the p53 V122A Mutation

Yeast has proven to be a useful system for the functional evaluation of wild type p53 and various p53 mutants from tumor cells. The use of reporter systems in yeast that utilize promoter elements from human genes recognized by p53 has enabled the dissection of functional domains of p53 (i.e., transactivation and DNA binding). Previously it was shown that p53 could inhibit growth of wild type yeast and that the inhibition was related to its DNA binding capabilities (30). With the isolation of several toxic mutants in different regions of the DNA binding domain, this invention shows that p53 mutants can be generated with a greater ability to inhibit growth not only in yeast, but also in mammalian cells. Previous studies of p53 mutants generally involved protein expression under control of the constitutive ADH1 promoter.

No lethal p53 mutants in yeast have been reported prior to the present invention. The rapid loss of ability to divide in response to the expressed mutant p53 was followed by loss of viability. Characterization of p53 mutations generated in vitro or recovered from tumors has generally involved cloning p53 into a constitutive promoter cassette. As shown herein, this level of expression would likely prevent growth of a toxic p53 mutant. Thus, it is only possible to isolate such mutants using either conditions of low expression or by using an inducible promoter. Even the modest level of expression with the constitutive ADH1 promoter prevented cell growth, which explains why this p53 class of mutants had not been isolated previously. The GAL1 promoter has proven ideal since its level of expression can be varied by the sugar supplement used for growth. This feature is also used herein to characterize novel p53 mutants that are super inducers of transcription.

The expressed protein is normally stable in yeast and human cells based on Western blot analysis. The consequences of co-expression of the V122A mutant protein together with various p53 functional mutations in yeast indicates that it can interact with wild type and mutant p53's. The V122A mutant has a strong dominant effect on growth when co-expressed with wild type p53, but much less of an effect in the presence of DNA binding mutations. Similarly, a double mutant that is V122A and lacks the tetramerization domain is not toxic. Double mutants that have altered amino acids at sites involved in DNA contacts or correct folding also reduced the lethal impact of V122A.

The p53-V122A mutant is completely defective in transcription in the RGC yeast reporter system that was used. This was shown under conditions of low levels of transcription and with double-mutants where growth was not completely abolished. Since the reporter system utilized an RGC binding site, which has a lower binding affinity than promoter elements such as p21, it is possible that the V122A mutation leads to altered specificity. If there was simply reduced binding ability, then it is unlikely that the mutant would have a greater than wild type p53 impact on growth. A mutant, S121F, had been described near this position; however, it exhibited only a subtle change in sequence specificity (Freeman et al.).

Surprisingly, all of the toxic mutant alleles identified in this study appeared to be defective in transactivation of a minimal yeast promoter containing 3 copies of the RGC p53 responsive element. If the only effect of the mutations were to reduce p53 DNA binding capacity, then toxicity would be an unlikely result, based on the phenotypic correlation between DNA binding transactivation and growth inhibition by wild type and mutant p53. The analysis of transactivation with the bax and the p21 responsive elements revealed that all the toxic p53 mutants not only retain transactivation potential with some promoter elements, but also appear to possess an enhanced "supertrans" activity compared to wild type p53. In particular, p53-V122A activated transcription of bax::ADE2 and p21::ADE2 at very low level of expression unlike wild type p53. p53-G279R did not show enhanced transactivation with any of the promoter elements tested, but showed normal transactivation with p21::ADE2 and it clearly caused toxicity at moderate or high expression. This mutant may possess high DNA binding affinity for a different p53 responsive element.

A p53 variant with enhanced transactivation may be able to intragenically suppress non-functional mutations elsewhere in the DNA binding domain. The extent of suppression is also likely to be affected by the relative affinity of p53 for a given responsive element and the degree of perturbation introduced by the non-functional mutation. p53-V122A was indeed able to re-activate a number of non functional tumor mutants for p21::ADE2 (see Table 6). Only two mutations were partially or completely re-activated for bax::ADE2 transactivation, and as expected no double mutant was active with RGC::ADE2 (see Table 1).

The present invention shows that the selection for toxic variants of p53 in yeast allows easy isolation of p53 mutants that exhibit relevant altered functional properties. The p53 functional assay in yeast has repeatedly been demonstrated reliable and sensitive at characterizing inactivating mutations isolated from human tumors. However, the predictability of the yeast assays on the impact of subtle or enhanced function mutations in human cells needed to be evaluated. These experiments in a human tumor cell line show that p53-V122A mutant retains biological function, partially reactivates a tumor p53 mutant and exhibits enhanced transactivation in transient luciferase assays with a bax responsive element.

The V122A single mutant was not distinguishable from wild type p53 in terms of ability to prevent colony formation of the human Saos-2 cells. It is interesting that, similar to results in yeast, this mutation when combined with G279E as a double mutation resulted in decreased colony forming ability compared to G279E alone. The p53-V122A protein retained some ability to induce synthesis of p21 as compared to wild type p53, while the V122A::G279E double mutant exhibited almost no p21 induction. The double mutant V122A::R282Q also had decreased synthesis of p21, whereas there was a near normal level when R282Q was expressed. The effect of p53-V122A expression both in yeast and in human cells is summarized in Table 5.

p53-V122A did not show higher induction of endogenous p21 compared to wild type p53 in the Saos-2 cells and did not completely re-activate p53-G279E. However, the double mutant showed some induction of p21at 48 hours after transfection. Luciferase assays with a p21 responsive element confirmed the western blot results in that no enhanced activity for p53-V122A was observed. The p21 reporter system in yeast and mammalian cells differed in that mammalian cells contained a large fragment of the p21 promoter that includes two different p53 responsive elements and can also be regulated in a p53 independent way. The yeast system instead utilizes only the 5' p21 responsive element. The affinity of p53 for these two responsive elements is different (Thornborrow et al.) and the relative contribution of each to p21 expression is not well characterized.

In luciferase assays, p53-V122A retained full transactivation activity with the 13xRGC::luc and re-activated the G279E mutation. No such effect was seen in yeast with a 3xRGC::ADE2. This difference may be explained by the different copy number of p53 responsive element and by the high copy number of the mammalian reporter plasmid. The reporter system in yeast is integrated as a single copy in the genome. p53-V122A showed about 4 fold higher luciferase activity than wild type p53 for the bax::luc reporter system. The level of p53 proteins in the same extract was similar. p53-V122A did not reactivate the G279E mutation for bax::luc. In this case the same p53 binding sequence is used in the mammalian and yeast reporter and the transactivation results with both single and double mutant are very similar. Thus, the suggestion that V122A retains some DNA binding activity and possibly altered sequence selectivity is consistent with both the yeast and the mammalian cell results.

Rare p53 Mutations and Implications

Position V122 is invariant among p53 protein sequences analyzed from 20 different species (Soussi and May). Based on the crystal structure of the p53 DNA binding domain from (Cho et al), it is contained within the large L1 loop. Residue 120 in this loop provides an essential contact with DNA. While residues in this region of the protein are highly conserved, few human tumor-associated p53 mutants are found in this region. This is surprising, since there is generally a strong correlation between sequence conservation and the incidence of p53 alterations in tumors (Walker et al.). No V122A tumor mutations have been identified (based on a search of the p53 database, containing more than 10.000 entries, Hainaut at al.,), although a single V122L mutant has been reported. However, it has been possible to generate p53 variants in the L1 loop that are functionally altered.

Mutations at codon 277 and 279 also caused toxicity. The amino acids C277 and G279 are invariant among p53 protein sequences. Cysteine 277 directly contacts the DNA sequence in the major groove based on p53/DNA crystal structure (Cho et al.), and amino acid changes at this codon exhibit altered DNA binding specificity (Gagnebin et al.; Thukral et al.; and Saller et al.). Neither C277R nor C277W changes have been identified in tumors. A p53 mutant with a C277R alteration was shown recently to activate transcription of p21 and MDM2 when expressed transiently in mammalian cells; however, its impact on growth was not reported. The mutant exhibited a defect in transactivation from specific synthetic p53 responsive elements and had a defect in apoptosis induction in Saos-2 cells (Saller et al.). The in vitro DNA binding activity of p53-C277W mutant protein has been evaluated in bandshift assays using only the distal p21 responsive element; no defect was observed (Chene et al.).

It is interesting that the G279R was isolated as a toxic p53 variant in these studies since this mutation appears several times in the p53 tumor database. One possibility is that p53-G279R lethality in yeast results from altered sequence recognition that in mammalian cells activates a partially defective p53 response that is compatible with tumor progression. No transactivation of RGC or bax by p53-G279R was observed in the present studies, but there was normal transactivation of p21::ADE2. Several tumor mutations have been identified at G279 that can impair p53 transactivation function (44) including the G279E used in this study. Clearly, different amino acid changes at the same G279 position can have dramatically different effects on yeast. For example, unlike G279R the over-expressed p53-G279E had only a small growth inhibitory effect.

Utility of Toxic p53 Mutations

This study has revealed a class of mutants that can be useful in various approaches that investigate and utilize tumor mutations.

One approach is to identify p53 mutants that would greatly increase the impact of p53 in yeast. The V122A mutation is not the only p53 mutation that is toxic. Additional single amino acid changes have been found that result in p53 lethality (see Table 3). Some mutations affect residues in the L1 loop, while others affect the DNA binding domain and also the tetramerization domain. The mutants could be functionally distinguished, since some of the toxic mutants also retained transcriptional capability.

There are several uses for a p53 class of toxic mutants. However, the presence of endogenous mutant proteins which may possess a dominant negative potential over wild type p53 could limit efficacy and alternative approaches are provided. A toxic allele such as p53-V122A can have the added benefit of being more potent and more specific. For example, cells would be directed more to an apoptotic mode of elimination if p21 induction were less efficient compare to bax inactivation. In addition, reduced p21 induction would suggest that combined treatments with commonly used chemotherapeutic agents might be more effective since there would not be a checkpoint control response.

Since the toxic p53 variants in yeast exhibit altered promoter recognition they could be useful in the functional dissection of downstream p53 pathways and in the identification of novel p53 targets. Altered DNA sequence specificity, could also be exploited to construct reporter systems that will preferentially be activated in cells transfected with such p53 mutations.

Since p53 plays a key role in preventing the development of cancer and most tumors associated with mutant p53 contain highly overexpressed missense mutant p53, reactivation or restoration of p53 function to tumor cells is a promising cancer therapy approach (Gallagher). Different strategies have been attempted aimed at specifically targeting mutant p53 tumor cells. For example, a defective adenovirus able to replicate only in the absence of p53 checkpoint function is under clinical trial (Bischoff et al). The idea of exploiting the high level of mutated protein to drive selective induction of a toxic gene has also been examined (Costa et al). Alternatively, tumor mutants with altered base pair recognition could be used to specifically induce a toxin (Gagnebin et al).

The identification of the p53-V122A mutation, as well as several other mutant sites that could lead to toxicity even when the mutant has an additional preexisting common tumor type mutation (i.e. V122A::G279E), suggests that there might be chemicals, peptides, small molecules or other agents that could modify functional consequences of a mutant protein and turn it into a toxin. These chemicals could be tumor targeted, since most tumors associated with mutant p53 contain highly overexpressed missence mutant p53. Examples of tumor targeting strategies are described in the literature. The number of p53 toxic mutants that we have identified, interactions with several known tumor mutations, and unique consequences in human cells, will be useful in several aspects of p53 based therapies as well as for analyzing p53 function and dissection of downstream pathways.

Supertransactivating Mutants

Isolation and Characterization of Yeast Colonies Expressing p53 Alleles with Increased Transcriptional Activation Using Variable Expression by the GAL1 Promoter.

The recognition of changes in promoter specificity and binding affinity, which may be associated with p53 mutations or post-translational modifications is useful in understanding p53 structure/function relationships, categorizing tumor mutations and may lead to the development of cancer therapies. This invention exploits variable expression of human p53 in yeast to develop screens for mutants exhibiting novel phenotypes that would correspond to altered promoter selectivity and affinity. The p53 cDNA regions coding for the DNA binding and tetramerization domains were subjected to random PCR mutagenesis and were cloned directly by recombination in yeast into a vector with a GAL1 promoter whose level of expression could be easily varied. A novel simple screen was developed that directly identifies p53 variants exhibiting greater than wild type levels of transactivation (supertrans) for the RGC responsive element. All the p53 mutants obtained with this screen were located in the DNA binding domain. Six were in the L1 loop region between amino acids 115 and 124. These supertrans mutants have not been observed in human tumors. The transactivation potential of a panel of supertrans p53 mutants on different promoters was evaluated using the p53 responsive elements, RGC, PIG3, p21 and bax. The sequence for the RGC response element is 5' GACCTTGC-CTGGACTTGCCTGGCCTTGCCT (SEQ ID NO: 1); the sequence for the p21 response element is 5'GAACATGTC-CCAACATGTTG (SEQ NO: 2); the sequence for the bax element is 5' TCACAAGTTAGAGACAAGC-CTGGGCGTGGGCTATATT (SEQ ID NO: 3) and the sequence for the Pig3 response element is 5' AGCTTGC-CCACCCATGCTCCAGCTTGCCCACCCATGCTC (SEQ ID NO: 4) Several patterns of induction were found based on strength and promoter specificity, suggesting that p53 mutants can be generated that can have a wide variety of biological responses. Interestingly, further analysis in yeast showed that the transactivation function could be retained even in the presence of dominant-negative p53 mutants that inhibited wild type p53. Many of the mutants affected amino acids located at protein positions distant from the DNA contact sites. Experiments in human cells correlated well with results in yeast in terms of growth suppression and effects on various promoters. These novel p53 mutants can be used to dissect p53 downstream pathways, understand specific interactions between p53 and the DNA, and can replace wild type p53 in cancer gene therapy protocols.

The yeast strains, plasmids, media and reagents were obtained as previously described above for the toxic mutants. The human p53 cDNA between nucleotide 124 and 1122 was PCR amplified using a TAQ DNA polymerase without proofreading activity under optimal reaction conditions.

Unpurified amplification products were used to perform GAP repair cloning in the yeast strain yIG397. An aliquot of the PCR amplification was used for GAP repair in pRDI-22 plasmid. Homologous recombination in yeast reconstitutes a constitutive p53 expression plasmid that utilizes the moderate ADH1 promoter to transcribe the p53 cDNA. Transformants are selected for the plasmid marker and p53 trasactivation function is tested on plates containing limiting adenine. This is possible since the yIG397 strains contains a p53-dependent reporter gene, ADE2, whose transcription can be monitored by a color assay. Transcription of ADE2 requires p53 because the upstream activating sequences of its yeast promoter have been deleted and replaced with three copies of a p53 binding sequence originally found in the human Ribosomal Gene Cluster (RGC). Since wild type p53 has been shown to act as a transcription factor also in S. cerevisiae, yeast transformant colonies expressing wild type p53 have a ade+ phenotype and produce normal size white colonies, while transformants expressing a non functional p53 will be ade– and produce smaller red colonies. The color is due to the accumulation of an intermediate in the adenine biosythesis. This color discrimination also allows the identification of intermediate phenotypes (i.e. pink colonies), possibly due to the expression of p53 alleles retaining partial function like temperature sensitive ones. Since the PCR product was obtained using wild type p53 as template sequence, the percentage of red colonies after GAP repair in pRDI-22 indicates the frequency of random p53 functional mutations generated by polymerase errors. In our experiments a 15 to 20 percent of red colonies was found (FIG. 8, panel A). While the GAP repair cloning in a constitutive expression plasmid is suitable for the isolation of nonfunctional p53 alleles it cannot discriminate between wild type p53 and p53 allelic variants that possess a "super" transactivation potential.

To obviate this limit GAP repair cloning was performed using a pGAL1 expression plasmid, pLS89, and exploiting variable expression of p53 by plating transformants on plates containing different carbon sources. yIG397 cells transformed with pLS89 produce dark red colonies on glucose plates, where the GAL1 promoter is repressed. The same clones produce lighter red colonies on raffinose plates where the GAL1 promoter is not repressed by glucose, but not induced. On galactose plates colonies are instead white, but growth is limited as the result of the inhibitory effect due to wild type p53 over-expression. p53 protein levels were checked by Western blot recovering cells after growth in different sugars. pGAL1 and pADH1 driven expression were also compared. Immunodetection confirmed that pGAL1 p53 expression on galactose is about tenfold higher than pADH1 expression on glucose. In glucose and raffinose cultures, pGAL1 driven p53 expression was respectively not detectable or barely detected. It was reasoned that GAP repair cloning in pGAL1 expression plasmid and plating on raffinose might allow the discrimination between wild type p53 and "super" wild type p53 for transactivation. Since wild type p53 produces light red colonies in this condition, the possibility to identify pink or white colonies might lead to the isolation of the "super" wild type p53's. As shown in FIG. 8, panel B white (and pink) colonies can be scored on raffinose plates. Their frequency is about 5% of the frequency of nonfunctional p53 mutants (i.e. red colonies in FIG. 8, panel A) or about 0.7-1% of the total number of transformants. Given the estimated number of base pairs where a substitution can affect the transcriptional activation function in the p53 cDNA (542 bp, Flaman) and assuming random polymerase errors, it was estimated that approximately 30 "super trans" p53 alleles could be generated with this approach among 3000 to 10,000 colonies examined. In four independent experiments 18 white colonies and 7 pink colonies were isolated and analyzed.

In order to confirm that the phenotype was due to the p53 region under study and not dependent for instance on variation of plasmid copy number inside the cell, plasmids were rescued and used to amplify the same p53 fragment. Gap repair was repeated and the phenotype confirmed in all isolates. A typical result is shown in FIG. 9. GAP repair transformants with a "super trans" allele and with wild type p53 as control were respectively plated on the left and right half of the same plate. Almost all colonies produced by the "super" transactivating p53 are larger and white. The small red colonies visible (one in the shown picture) likely represents ligated vector without p53 insert or nonfunctional p53 mutations occurred during amplification. Their low frequency (below 5%) compared to that obtained when wild type p53 is PCR amplified in the same experimental condition probably indicates that "supertrans" alleles can tolerate some second site missense mutations, remaining phenotypically wild type.

The phenotype of "supertrans" p53 isolates under control of pGAL1 promoter was then tested in glucose and galactose plates (FIG. 10). Upon over-expression all these p53 variants reduced the growth of yeast and in some cases resulted in a no-growth phenotype. This result is consistent with our previous observation (Inga and Resnick) that growth inhibition due to p53 expression in S. cerevisiae partly correlates with DNA binding and transactivation potential. Wild type p53 caused growth inhibition whereas nonfunctional tumor mutants have almost no effect. The phenotype of the "supertrans" mutants here reported confirms the hypothesis that DNA binding correlates with impact on growth of yeast. However, the "supertrans" p53 variants have a distinct phenotype compared to the lethal mutant p53-V122A and have to be considered a separate category of p53 alleles with altered functional properties.

The phenotypic consequences of constitutive expression of 25 of the p53 "supertrans" alleles were examined transferring them to ADH1 expression plasmids. Among 25 alleles, 21 produced large white colonies. Four of them, all originally isolated as white colonies on raffinose, prevented yeast growth when expressed under pADH1. This result confirms that p53 variants possessing increased transcriptional activation potential compared to wild type would not be identifiable in the original p53 functional assay because they are not distinguishable from wild type p53 or they prevent growth of yeast.

p53 "super trans" clones were then sequenced in order to determine the nature of the molecular alteration in the p53 cDNA that leads to this altered or "improved" function. Sequencing results are reported in Table 6 together with the phenotypic effect of each allele on glucose (pADH1 plasmid) raffinose or galactose (pGAL1 plasmid) plates. All the analyzed isolates contained at least a missense mutation in the region under study. In some cases the same base pair substitution was found in two independent clones. Seven clones showed two or three amino acid changes. In some cases the mutation responsible for the phenotype in these isolates can be indicated based on its effect as single change in other clones.

The nature of the mutation(s) in the p53 cDNA of 18 white and 7 pink supertrans clones was determined by DNA sequencing. Presented in Table 6 are the amino acid change(s), and the number of identical mutations that have been reported at the same codon in tumors. Among 25 independent clones there were 26 different amino acid changes and 17 mutants contained a single amino acid change, suggesting that the number of supertrans mutations have not been saturated. This invention therefore contemplates any supertransactivating mutations identified in the future by the screening methods of this invention. The L1 loop is a hotspot region for supertrans p53 mutants: 7 different changes at four positions.

The location of the affected amino acids based on the crystal structure of p53 DNA binding domain (Cho) is also reported in Table 6. Although the mutagenesis protocol involved a larger region, all mutations leading to supertrans p53s have amino acid changes in the DNA binding domain suggesting that the mutations may have a direct impact on DNA binding. Several mutations are in fact located in the L1 loop-sheet-helix motif and the L2 and L3 loops and the amino acids they affect are close to the DNA ($\leq 8A$)(see FIG. 18). Other mutations are far from the protein::DNA interface and affect amino acids that map to the β-sandwich and might increase its stability. The observation that these mutants exhibit enhanced transactivation only for specific responsive elements indicates that the amino acid changes indirectly affect DNA recognition instead of affecting general monomer/tetramer stability. Two sequence alterations were found in the tetramerization domain but in combination with at least another amino acid change. These two mutations were separated and tested under the control of the GAL1 promoter. Both F338L and N345S produced red colonies on raffinose plates. N345S was not phenotypically distinguishable from wild type p53, while F338L led to an even greater growth inhibition. When this altered protein was over-expressed on galactose tiny colonies appeared after five days of incubation having approximately one fourth the size of colonies containing wild type p53. Under control of the constitutive ADH1 promoter F338L appeared as wild type p53. It is possible that this amino acid change in the tetramerization domain is affecting tetramer stability leading to a slightly increased toxicity in yeast. As it was previously reported growth inhibition or toxicity due to p53 over-expression in yeast requires tetramerization.

The right columns in Table 6 report the occurrence in the p53 database of both deletions and amino acid changes at the nucleotide positions where "super trans" changes were observed. The presence in the database of amino acid changes identical to the ones isolated in this study is also reported. Most of the p53 allelic variants showing increased transcriptional activation are novel in the very large in vivo database (14,000 entries in the April 1999 release) and generally they affect cold spots of mutation in tumors. Seven among 18 "super trans" amino acid changes have also been reported in the database. Of these, four were found only in one tumor sample, while the other three (H178Y, T230I, and V274A) were detected in different tumor samples and tissues.

In order to confirm the increased transactivation capability of these alleles in yeast, some of the described p53"supertrans" alleles were tested by a gene reporter assay based on the β-galactosidase gene. Briefly, double transformants were selected containing a pGAL1 plasmid for p53 expression and a 2 micron vector containing the β-galactosidase gene under p53 control. The same RGC sequence mediates p53 binding and transcriptional activation in this vector. The following "supertrans" alleles were tested: S121F (w3), T123A (w4), C124Y (w6), D184G (p3), S240N (w15), and a constructed double mutant N288K::F338L (w17-d). β-galactosidase activity was determined after 8 hours of growth in liquid selective medium containing raffinose as carbon source (FIG. 11). "Supertrans" alleles induced β-galactosidase at a much higher level compared to wild type p53. This result confirms the observation that the novel yeast assay we developed is able to isolate p53 alleles with increased transactivation potential over the wild type.

Both the ADE2 and β-Gal reporters confirmed that single amino acid changes in p53 DNA binding domain can greatly enhance the transactivation activity of human p53 in yeast. It is possible that these mutations increase the affinity of the DNA binding domain for the p53 responsive element used in the screen (3xRGC). Alternatively, the mutations may have a stabilizing effect on p53 conformation or affect protein:: protein interactions. The amount of wild type p53 and four supertrans mutants in raffinose cultures was evaluated by western blot. All mutants showed a comparable and slightly reduced protein level compared to wild type p53 (FIG. 12). The slight reduction might be due to a minor effect of supertrans alleles on yeast growth even at low expression. When the GAL1, 10 promoter was repressed (in glucose medium) the amount of protein was markedly reduced and more homogeneous (only wt and T123A are shown). This result demonstrates that the supertrans phenotype is not due to an increased amount of p53.

Transactivation by Supertrans p53 Mutants at Different Expression Levels and with Various p53 Responsive Elements Since the supertrans alleles were identified using the RGC response element upstream from the ADE2 reporter, it was important to evaluate the generality of the supertrans effect. Many of the alleles were examined for their ability to transactivate with the p21, bax and PIG3 responsive elements in addition to the RGC using the same ADE2 reporter (26). A combination of raffinose and small amounts of galactose was also used to achieve variable levels of p53 induction. Among the nine mutants tested, the supertrans responses for RGC and PIG3 response elements were similar (Table 7). None of the mutants was supertrans with the p21 responsive element, while three mutants exhibited enhanced transactivation with the bax element. All supertrans mutants retained wild type levels of transactivation proficiency for the four responsive elements at higher level of expression (2% raffinose+0.015% galactose), but unlike wild type p53 they completely prevented growth at very high induction (raffinose+0.5% galactose). This result suggests that moderate expression of supertrans alleles under the ADH1 promoter may result in a white colony phenotype that is not distinguishable from wt p53. ADH1 expression plasmids for all the mutants in Table 6 were constructed and tested in yIG397 on glucose plates. All the mutants except S240N, which prevented growth, gave rise to white colonies. Thus, the supertrans alleles cannot be identified when p53 is constitutively expressed by the ADH1 promoter.

Testing the Dominance Potential of p53 "Supertrans" Alleles.

Some of the p53 tumor mutations and in particular mutation hotspots in tumors are considered to be the dominant negative phenotype over wild type in heterozygosis. This effect is generally explained by the ability of these mutants to form hetero-tetramers with wild type and reduce or compromise their function. Having generated p53 alleles that show increased transactivation compared to wild type we tested whether "supertrans" alleles might be resistant to the dominant negative phenotype of p53 tumor mutations.

Plasmids were constructed that express p53 alleles under the constitutive ADH1 promoter. These vectors were transformed in yeast together with differently marked but otherwise identical vectors expressing p53 mutations.

Double transformants were selected and tested for transactivation with the ADE2 based color assay. An example of this phenotypic analysis is shown in FIG. 13 while results are summarized in Table 8. Five supertrans alleles were tested against six p53 dominant-negative tumor mutants. Yeast transformants containing both tumor and either wild type or supertrans expression plasmids were obtained on double selective plates. Five of the six tumor mutants inhibited wild type activity (pink colonies) (Table 8). Interestingly, the S121F, T123A and V274A supertrans mutants were resistant to the dominant negative phenotype (white colonies). The S240N mutant prevented growth when expressed under ADH1 promoter and the presence of wild type p53 did not alleviate this phenotype. Co-expression of p53 tumor mutants allowed the appearance of white colonies, suggesting that mixed tetramers can be formed and that the DNA binding activity was partially affected but transactivation was retained. The H178Y mutant was similar to the wild type p53 when tested in combination with the various tumor mutants. At the same time colony color is close to that expected from wild type p53 expressing clones, suggesting that also S240N can tolerate the negative effect of p53 dominant mutations.

The test for dominance of the supertrans versus the tumor mutants was repeated with the bax response element since it exhibits a lower binding affinity for p53 and the dominant negative phenotype over the wild type is stronger (Table 9). Two supertrans mutants were tested against five dominant negative mutations. Interestingly, while wild type p53 was completely inhibited by the tumor mutations, both S121F and T123A retained full activity.

The invention also provides p53 allelic variants that discriminate between different p53 regulated pathways. For example, p53 mutants are identified that preferentially enhance transactivation of defined p53-regulated genes while retaining normal or even reduced activity for others. Thus, the system provides the opportunity to "tailor" p53 functional control for the various promoters recognized by p53 in terms of strength of induction by 53 (from none to supertrans) and for combinations of p53 responsive genes (i.e., some turned on, some turned off). This provides opportunities to change the p53 responsive pathways and therefore the biological outcomes in response to environmental challenges. New promoter response elements are identified that can be recognized by new (mutant) forms of p53. The system also provides the opportunity to identify or tailor mutant p53s that are dominant when expressed with other (i.e., common tumor p53) mutants.

Supertrans p53 mutants for the p21 and the bax responsive elements and additional supertrans for RGC have been isolated. These mutations are presented in Table 10. Amino acid changes in the L1 and L3 loops, H2 helix and also in strands S4 and S10 were identified. Some mutations exhibited supertrans phenotype with both bax and p21 or bax and RGC, while others appeared more specific for a responsive element. Most of the mutations have not been detected in tumors. A summary of the transactivation analysis for all the supertrans alleles identified so far is presented in Table 11. Different patterns of transactivation and supertransactivation have been observed ("pattern" summarizes the promoter elements that are turned on and turned off by the mutant p53, the level of response for each promoter element, and potential toxicity of a p53 mutant). Some mutants exhibit strong specificity for a given responsive element, while others appear more active than wild type for all the elements tested. These latter mutations may increase folding stability or introduce additional DNA contacts but without affecting specificity. Different amino acid changes at the same position in the L1 loop (121, 123 and 124) showed different patterns of transactivation specificity and affinity.

Expression of p53 "Supertrans" Alleles in Human Cells.

The results obtained in yeast convincingly indicate that the alleles we have isolated possess increased transactivation potential in gene reporter assays that utilize the human RGC sequence as p53 binding element. Moreover, the fact that several "supertrans" alleles are not commonly seen or have never been observed in tumors argue against the possibility that they have lost relevant functions for the p53 biology. It is possible that in some cases altered specificity explains increased trasactivation leaving the possibility that not all the p53 downstream genes can be equally activated. Besides, it is possible that yeast specific factors can modulate transactivation of p53 and conversely it is likely that yeast lacks proteins that play an accessory role in p53 mediated transactivation in human cells. For this reasons the effect of p53 "supertrans" alleles needs to be explored also in human cells. The present mutations and screening methods are valuable research tools in the further elucidation of p53 activities in humans.

Five supertrans mutants were therefore examined in p53 null Saos-2 tumor cells, in order to evaluate their biological effect when expressed in human cells. The cells were transfected with p53 mutants expressed from the strong CMV promoter. As shown in FIG. 14, the S121F, C124Y and S240N mutants cause a somewhat greater growth suppression than wild type p53 (5-7% vs 13% relative colony formation). The V274A mutant was unable to suppress growth; however, this mutant was temperature sensitive for transactivation in yeast 37° C.

Growth suppression by wild type p53 can be alleviated by excess expression of a dominant negative p53 tumor mutant (FIG. 14 and FIG. 15). As suggested from the above experiments in yeast, supertrans alleles might be resistant to this inhibition. To test this, co-transfection experiments were performed using a 1:4 plasmid ratio of wild type or supertrans (S121F and T123A) p53 vs the mutant G279E (FIG. 15). As expected, the dominant negative G279E tumor mutant reduced the activity of wild type p53 as evidenced by the much greater relative colony formation when G279E was present (50% vs 13%; see FIG. 5). Again, this shows that supertransactivating mutations can overcome dominant negative mutations.

A similar effect was observed for T123A+G279E. The presence of G279E appeared to have less of an effect in alleviating the S121F induced growth defect.

The ability of the various mutants to transactivate a luciferase reporter gene having the bax, MDM2 and p21 responsive element was also examined. Two plasmids, one for p53 expression and the other containing the reporter gene, were transfected into Saos-2 cells and the induction of luciferase was determined. The bax responsive element was the same as that used in yeast whereas the p21 and MDM2 elements were different as the complete p21 and MDM2 promoters were used in the Saos-2 cells. As shown in FIG. 16, V274A did not exhibit transactivation as expected from the results in yeast at 37° C. where it was temperature sensitive. The, S121F mutant was unable to activate the luciferase reporter despite very strong suppression of growth. While the levels differed, the other three super supertrans mutants T123A, C124Y and S240N, were all able to induce luciferase regardless of the responsive elements tested. The strongest response, which was somewhat greater than for wild type p53, was found with the MDM2 promoter. The levels of p53 protein expression in the transient transfections were comparable based on Western blot analysis (FIG. 17). As expected, the V274A mutant was better tolerated and the protein amount was higher. Using an antibody to p21, examined the ability of the various p53 alleles to induce the endogenous p21 from its own promoter was also examined. The S121F mutant showed a partial defect in p21 induction. T123A, C124Y and S240N all induced p21, as did the wild type p53 while V274A appeared completely defective. Thus, the results in yeast with the partial p21 responsive element (Tables 7 and 12) and the endogenous p21 promoter in Saos-2 cells were comparable.

Defects or changes in promoter specificity and affinity caused by mutations in the p53 DNA binding domain leading to partial or complete abrogation of p53 functions are a key event in tumor development. Even though a few major hotspots are observed, p53 tumor mutations occur throughout the DNA binding domain (Hernandez-Boussard et al.) possibly because its structure, consisting of a β-sandwich scaffold that supports a loop-sheet-helix and two $Zn^{2+}$ coordinating loops that contact DNA (Cho et al.), is highly susceptible to inactivating mutations. Recent in vitro studies quantitatively addressed the effect of a large panel of tumor mutations on folding stability and DNA binding activity of the p53 core domain aiming at better categorizing p53 mutations and understanding the effect of defined amino acid changes on protein structure/function (Bullock et al. (1997), Bullock et al. (2000)). The same approach was applied in the attempt to design more stable variants of the p53 DNA binding domain without affecting DNA binding affinity for a promoter element and understanding the mechanism of functional reactivation of tumor mutants by second-site suppressor mutations (Nikolova et al. (1998); Nikolova et al. (2000)).

It is interesting to note that the commonly used p53 functional assays in yeast (Flaman, Ishioka, Frebourg, Di Como, Brachmann), expresses the protein under control of the constitutive moderate ADH1 promoter. With these assays all "supertrans" alleles would have been considered wild type p53 or would have been missed because of a no-growth phenotype (see Table 6).

Further analysis in yeast revealed that over-expression of "supertrans" alleles led to a no-growth phenotype while wild type p53 led to moderate growth inhibition. Two different isolates prevented growth even when moderately expressed. In this condition wild type p53 has no effect. These results confirm the hypothesis that growth inhibition in yeast partially correlates with DNA binding potential of p53 and that either changes in affinities or in sequence selectivity can lead to a worse impact on colony formation and even to lethality. The selection for lethal p53 variants can be regarded as an alternative and complementary approach to identify novel p53 variants possibly exhibiting unusual functions.

A prediction with the finding of p53 alleles exhibiting increased transcriptional activation is that they might be more resistant than wild type p53 to the dominant negative effect of common tumor mutants. This dominant negative effect can be seen in heterozygosity and may explain the strong in vivo selection for missense p53 mutations. It is possible that in mixed tetramers, subunits possessing higher DNA binding affinities than wild type can still mediate enough interaction with p53 responsive elements to allow transactivation. Alternatively, at physiological level of expression the minimal amount of "supertrans" homotetramers, but not of wild type ones (statistically 1/16 of total proteins in the case of heterozygosity and equal stability) required to achieve transcriptional activation could be reached. Using a simple assay originally developed to evaluate the dominance of p53 mutants over wild type, we tested the effect of a series of dominant tumor mutations on the transactivation potential of some "supertrans" alleles. The data presented herein suggests that indeed "supertrans" alleles can overcome the negative effect of tumor mutants at equal and moderate level of expression. This result indicates that "supertrans" alleles exhibiting this feature for a variety of p53 responsive elements might be of great value in therapy as an alternative to wild type p53 in approaches aiming at restoring p53 activity to tumor cells. Recent data suggest that wild type p53 gene therapy in human cancer cells may fail because highly expressed endogenous mutations inhibit the effect of the exogenous wild type protein. p53 alleles with increased transcriptional activation might exhibit more resistance to mutants and lead to a better outcome of this treatment.

The approach of this invention to select for increased transcriptional potential in p53 allelic variants has utilized three p53 responsive elements of which only two correspond to promoters of p53 regulated genes (bax and p21). Some of the mutations exhibited enhanced activity with at least two responsive elements (see Tables 6, 10, 11, 12) while other appeared more specific for one element. Most of the mutants have not been detected in tumors, suggesting that these proteins retain wild type like tumor suppressor activity and might possess distinct functional features. Additional p53 response elements can be utilized in the assays taught.

Studies with four alleles (S121F, T123A, C124Y, S240N) show that they can suppress growth as well as wild type p53, indicating that relevant biological properties has not been lost. Conversely, the fact that V274A is a tumor p53 mutant suggests that its function is impaired. When tested at different temperatures in yeast V274A was defective for transactivation at 37° C., which is consistent with V274A not being functional when expressed in human cells. Co-transfection experiments with combination of "supertrans" and dominant mutant (mutant in excess) indicate that p53-S121F is resistant to the dominant negative effect of a DNA binding mutant (p53-G279E) (FIG. 15).

The assay provided herein can be used as a screening tool for subtle p53 mutants in tumor samples since they may go undetected with the common p53 functional assay. Novel or rare mutations have been recently identified by direct sequencing in tumor samples and shown to possess wild type like transactivation function in human cells (Smith et al.). p53 mutations that exhibit weak transactivation defects were recently identified with the yeast screen of this invention in bladder cancer tissues.

Moreover, the assay is useful for the generation and characterization of novel p53 alleles that exhibit an altered pattern of regulation of downstream genes and is useful for in vivo functional dissection of p53 responsive pathways and identification of additional p53 regulated genes. The transactivation analysis at low expression with the complete human p53 protein and various tetrameric responsive elements provide a better understanding of p53-DNA binding specificity/affinity and stability. This approach can complement recent in vitro studies that addressed p53 folding stability and DNA binding affinity (Bullock et al.; Nikolova et al.).

The sensitivity of the yeast assay to various levels of p53 expression could be used to identify compounds (i.e. chemicals, small molecules or peptides) or interacting factors that either enhance or reduce p53 function. Such agents might also be able to functionally reactivate p53 tumor mutants (Foster et al; Selivanova et al.). Alternatively, temporary inactivation of p53 function may also have therapeutic value (Komarov et al.). Finally, supertrans p53 alleles provided herein or identified according to the present methods that exhibit selectivity for the induction of the apoptotic pathway may have a higher therapeutic effect compared to wild type p53 for cancer gene therapy under conditions where functional p53 is delivered directly to the tumor tissues (Saller et al.; Vinyals et al; Swisher et al.).

A summary of the responses in yeast and Saos-2 cells is presented in Table 12. A very good correlation between growth inhibition/toxicity in yeast and growth suppression in human cells was observed. The only exception of the V274A mutation is explained by the observation that the mutant is temperature sensitive at 37° C. Transactivation results with the yeast assay and the luciferase reporter in Saos-2 are also compared. Even though the responsive elements in yeast and human reporter constructs are different in arrangement and copy number, similarity of responses was observed even though the supertransactivation phenotype is not easily reproducible. Transactivation results in yeast also correlates well with the analysis on induction of the endogenous p21 gene.

Methods developed to examine human supertrans and toxic p53 mutants can also be used to examine nonhuman p53 genes. Examples are shown for mouse p53 wild type and R270C and T122L mutants (corresponding to human amino acid positions 273 and 125) in Table 13. T122L has been found in mouse skin cancer and is toxic in yeast and super trans for bax and p21 but reduced for RGC.

This system provides a specific, broadly applicable approach for modification of genes (master genes) that regulate multiple down stream genes through consensus promoter elements. Therefore, it may be possible to regulate specific pathways. The regulatable promoters can be included in reporters similar to that described for p53. An example of pathway specificity resulting from a change in a master gene is found for lexA of *E. coli*. J Mol Biol 1987 Jan. 5; 193(1):27-40. Differential repression of SOS genes by unstable lexA41 (tsl-1) protein causes a "split-phenotype" in *Escherichia coli* K-12. Peterson K R, Mount D W This invention has demonstrated that p53 can have a variety of effects. Whereas wild type has a set number of p53 promoters that it turns on and each promoter is turned on to a given degree, the present invention shows that through the use of yeast as a screening tool, combined with mutations of the p53 gene and characterization of p53 mutants at different expression levels the pattern of p53 response is changed.

Throughout this application, various publications are referenced. The disclosures of these publications in their entireties are hereby incorporated by reference into this application in order to more fully describe the state of the art to which this invention pertains.

REFERENCES

Baker et al., (1990) Suppression of human colorectal carcinoma cell growth by wild type p53. Science 249, 912-915

Bischoff, J, R. Casso, D., Beach, D., (1992) Human p53 inhibits growth in *Schizosaccharomyces pombe*. Mol. Cell. Biol., 12, 1405-1411.

Bullock, A. N., Henckel, J., DeDecker, B. S., Johnson, C. M., Nikolova, P. V., Proctor, M. R., Lane, D. P., and Fersht, A. R. (1997) Thermodynamic stability of wild-type and mutant p53 core domain, Proc. Natl. Acad. Sci. USA 94: 14338-14342.

Bullock A. N., Henckel J., and Fersht, A. R. (2000) Quantitative analysis of residual folding and DNA binding in mutant p53 core domain: definition of mutant states for rescue in cancer therapy, Oncogene 19: 1245-56.

Brachmann, R., Yu, K., Eby, Y., Pavletich, N., Boeke, J. (1998) Genetic selection of intragenic suppressor mutations that reverse the effect of common p53 cancer mutations, *EMBO J.* 17, 1847-1859.

Candau, R., Scolnick, D., Darpino, P., Ying, C. Y., Halazonetis, T. D., Berger, S. L. (1997). Two tandem and independent sub-activation domains in the amino terminus of p53 require the adaptor complex for activity. Oncogene, 15, 806-817.

Caron De Fromentel, C., Gruel, N., Venot, C., Debusschei, L., Conseiller, E. et al. (1999) Restoration of transcriptional activity of p53 mutants in human tumour cells by intracellular expression of anti-p53 single chain Fv fragments, *Oncogene* 18, 551-557.

Casso D, Beach D (1996) A mutation in a thioredoxin reductase homolog suppresses p53-induced growth inhibition in the fission yeast *Schizosaccharomyces pombe*. Mol Gen Genet., 16; 252, 518-529.

Chene, P. Mutations at position 277 modify the DNA-binding specificity of human p53 in vitro. Biochem Biophys Res Commun. 263: 1-5, 1999.

Cho, Y., Gorina, S., Jeffrey, P. D., Pavletich, N. P., (1994) Crystal structure of a p53 tumor suppressor-DNA complex: understanding tumorigenic mutations. Science, 265, 346-355.

Conseiller, E., Debussche, L., Landais, D., Venot, C., Maratrat, M., Sierra, V., Toque, B., Bracco, L., (1998) CTS1: a p53-derived chimeric tumor suppressor gene with enhanced in vitro apoptotic properties. J. Clin. Invest., 101, 120-127.

Cook, J L, Zhang, Z., Alam, J., Re, R. (1999) Effects of chromosomal integration site upon p53 interactions with DNA consensus sequence homologies, *Oncogene* 18, 2373-2379.

Da Costa, L., Jen, J., He, T., Chan, T., Kinzier, K. et al. (1996) Converting cancer genes into killer genes, *Proc. Natl. Acad. Sci. USA* 93, 4192-4196.

Di Como, C. J., Prives, C. (1998) Human tumor-derived p53 proteins exhibit site selectivity and temperature sensitivity for transactivation in a yeast-based assay. Oncogene 16, 2527-2539.

Flaman, J. M., Frebourg, T., Moreau, V., Charbonnier, F., Martin, C., Chappuis, P., Sappino, A. P., Limacher J. M., Bron, L., Benhattar, J., Tada, M., VanMeir, E. G., Estreicher, A., Iggo, R. D., (1995). A simple functional assay for screening cell lines, blood, and tumors. PNAS., 92, 3963-3967.

Flaman, J. M., Robert, V., Lenglet, S., Moreau, V., Iggo, R., Frebourg, T., (1998) Identification of human p53 mutations with differential effects on the bax and p21 promoters using functional assays in yeast. Oncogene 16, 1369-1372.

Foster, B. A., Coffey, H. A., Morin, M. J., and Rastinejad, F. (1999) Pharmacological rescue of mutant p53 conformation and function, Science 286: 2507-10.

Freedman, D., Levine, A. (1999) Regulation of the p53 protein by MDM2 oncoprotein-thirty-eighth G. H. A. Clowes memorial award lecture, *Cancer Res.* 59, 1-7.

Freeman, J., Schmidt, S., Scharer, E., Iggo, R. (1994) Mutation of conserved domani II alters the sequence specificity of DNA binding by the p53 protein. EMBO J., 13, 5393-5400.

Gagnebin, J., Kovar, H., Kajava, A., Estreicher, A., Jug, G. et al. (1998) Use of transcription reporters with novel p53 binding sites to target tumour cells expressing endogenous or virally transduced p53 mutants with altered sequence-specificity, *Oncogene* 16, 685-690.

Gallagher, W., Brown, R. (1999) p53-oriented cancer therapies: current progress, Ann. Review Oncol., 10, 139-150

Giaccia, A., Kastan, M. (1998) The complexity of p53 modulation: emerging patterns from divergent signals, *Genes Dev.* 12, 2973-3983.

Greenblatt, M., Bennett, W., Hollstein, M., Harris, C. (1994) Mutations in the p53 tumor suppressor gene: clues to cancer etiology and molecular pathogenesis, *Cancer Res.* 54, 4855-4878.

Gualberto, A., Aldafe, K., Kozakiewicz, K., Tlsty, T. (1998) An oncogenic form of p53 confers a dominant, gain-of-function phenotype that disrupts spindle checkpoint control, *Prot. Natl. Acad. Sci. USA* 95, 5166-5171.

Hernandez-Boussard, T., Rodriguez-Tome, P., Montesano, R., and Hainaut, P. IARC p53 mutation database: a relational database to compile and analyze p53 mutations in human tumors and cell lines. International Agency for Research on Cancer, Hum Mutat. 14: 1-8, 1999.

Hainaut P, Hernandez T, Robinson A, et al. (1998) IARC Database of p53 gene mutations in human tumors and cell lines: updated compilation, revised formats and new visualisation tools Nucleic Acids RES. 26, 205-213.

Hovland, P. Flick, J. Johnston, M. Sclafani, R. A. (1989) Galactose as a gratuitous inducer of GAL gene expression in yeasts growing on glucose. Gene 83, 1, 57-64.

Ishioka, C., Englert, C., Winge, P., Yan, Y. X., Engelstein, M., Friend, S. (1995) Mutational analysis of the carboxy-terminal portion of p53 using both yeast and mammalian cell assays in vivo. Oncogene, 10, 1485-1492.

Kern, S. E., Pietenpol, J. A., Thiagalingam, S., Seymour, A., Kinzler, K. W., Vogelstein, B., (1992) Oncogenic forms of p53 inhibit p53-regulated gene expression.

Ko, L., Prives, C. (1996) p53: puzzle and paradigm, *Genes Dev.* 10, 1054-1072.

Komarov, P. G., Komarova, E. A., Kondratov, R. V., Christov-Tselkov, K., Coon, J. S., Chernov, M. V., and Gudkov, A. V. (1999) A Chemical Inhibitor of p53 that Protects Mice from the Side Effects of Cancer Therapy, Science 285: 1733-1737.

Lee et al., (1997) Human p53 binds Holliday junctions strongly and facilitates their cleavage JBC., 272, 7532-7539.

Lewis, K. L., Kirchner, J. M., and Resnick, M. A. (1998) Requirement for end-joining and checkpoint functions, but not RAD53-mediated recombination, after EcoR1 endonuclease cleavage of *Saccharomyces cerevisiae* DNA. Mol. Cell. Biol. 18: 1891-1902.

Ludwig, R., Bates, S., Vousden, K. (1996) Differential activation of target cellular promoters by p53 mutants with impaired apoptotic function, *Mol. & Cel. Biol.* September, 4952-4960.

Matsumura, I., Ellington, A. D. (1999) In vitro evolution of thermostable p53 variants. Protein Science 8, 731-740.

McLure, K., Lee, P. (1998) How p53 binds DNA as a tetramer, *EMBO J.* 17, 3342-3350.

Meek, D. (1998) New developments in the multi-site phosphorylation and integration of stress signalling at p53, *Int. J. Radiat. Biol.* 74, 729-737.

Mummenbrauer et al., (1996) p53 Protein exhibits 3'-to-5' exonuclease activity Cell, 85, 1089-1099

Nigro, J. M., Sikorski, R., Reed, S. I., Vogelstein, B., (1992). Human p53 and CDC2Hs genes combine to inhibit the proliferation of *Saccharomyces cerevisiae*. Mol. Cell. Biol., 12, 1357-1365.

Nikolova, P., Henckel, J., Lane, D., Fersht, A. (1998) Semi-rational design of active tumor suppressor p53 DNA binding domain with enhanced stability, *Proc. Natl. Acad. Sci. USA* 95, 14675-14680.

Nikolova, P. V., wong, K. B., DeDecker, B., Henckel, J., and Fersht, A. R. (2000) Mechanism of rescue of common p53 cancer mutations by second-site suppressor mutations, EMBO J. 19: 370-378.

Prives, C., Hall, P. (1999) The p53 pathway, *J. Pathol.* 187, 112-126.

Resnick-Silverman, L., Clair, S. S., Maurer, M., Zhao, K., Mafredi, J. (1998) Identification of a novel class of genomic DNA-binding sites suggests a mechanism for selectivity in target gene activation by the tumor suppressor protein p53, *Genes Dev.* 12, 2102-2107.

Roland Walker, D., Bond, J., Tarone, R., Harris, C., Makalowski, W. et al. (1999) Evolutionary conservation and somatic mutation hotspot maps of p53: correlation with p53 protein structural and functional features, *Oncogene* 19, 211-218.

Saller, E., Tom, E., Brunori, M., Otter, M., Estreicher, A., Mack, D. H., and Iggo, R. Increased apoptosis induction by 121F mutant p53, Embo J. 18: 4424-37, 1999.

Selivanova, G., Ryabchenko, L., Jansson, E., Iotsova, V., and Wiman, K. G. (1999) Reactivation of mutant p53 through interaction of a C-terminal peptide with the core domain, Mol. Cell. Biol. 19: 3395-402.

Sharer, E., Iggo, R. (1992) Mammalian p53 can function as a transcription factor in yeast, *Nucleic Acids Res.* 20, 1539-1545.

Smith, P. D., Crossland, S., Parker, G., Osin, P., Brooks, L., Waller, J., Philp, E., Crompton, M. R., Gusterson, B. A., Allday, M. J., and Crook, T. (1999) Novel p53 mutants selected in BRCA-associated tumors which dissociate transformation suppression from other wild-type p53 functions, Oncogene. 18: 2451-9.

Soussi, T., May, P., (1996) Structural aspects of the p53 protein in relation to gene evolution: a second look. J. Mol. Biol., 260, 623-637.

Stommel, J., Marchenko, N., Jimenez, G., Moll, U., Hope T. et al. (1999) A leucine-rich nuclear export signal in the p53 tetramerization domain: regulation of subcellular localization and p53 activity by NES masking, EMBO J. 18, 1660-1672.

Stott F J et al., (1998) EMBO J., 17, 5001-5014.

Swisher, S. G., Roth, J. A., Nemunaitis, J., Lawrence, D. D., Kemp, B. L., Carrasco, C. H., Connors, D. G., El-Naggar, A. K., Fossella, F., Gilsson, B. S., Hong, W. K., Khuri, F. R., Kurie, J. M., Lee, J. J., Lee, J. S., Mack, M., Merritt, J. A., Nguyen, D. M., Nesbitt, J. C., Perez-Soler, R., Pisters, K. M., Putnam, J. B., Jr., Richli, W. R., Savin, M., Waugh, M. K. and et al. (1999) Adenovirus-mediated p53 gene transfer in advanced non-small cell lung cancer, J. Natl. Cancer Inst. 91: 763-71.

Thornborrow, E. C. and Manfredi, J. J. One mechanism for cell type-specific regulation of the bax promoter by the tumor suppressor p53 is dictated by the p53 response element, J Biol Chem. 274: 33747-56, 1999.

Thukral, S. K., Lu, Y., Blain, G. C., Harvey, T. S., and Jacobsen, V. L. Discrimination of DNA binding sites by mutant p53 proteins, Mol Cell Biol. 15: 5196-202, 1995.

Tokino, T., Thiagalingam, S., El-Deiry, W., Waldman, T., Kinzler, K. et al. (1994) p53 tagged sites from human genomic DNA, Human Mol. Gen. 3, 1537-1542.

Tran, H. T., Keen, J. D., Kricker, M., Resnick, M. A., Gordenin, D. A. (1997) Hypermutability of homonucleotide runs in mismatch repair and DNA polymerase proofreading yeast mutants. Mol. Cell. Biol., 17, 2859-2865.

Venot, C., Maratrat, M., Dureuil, C., Conseiller, E., Bracco, L. et al. (1998) The requirement for the p53 proline-rich functional domain for mediation of apoptosis is correlated with specific PIG3 gene transactivation and with transcriptional repression, EMBO J. 17, 4668-4679.

Venot, C., Maratrat, M., Sierra, V., Conseiller, E., Debussche, L. (1999) Definition of a p53 transactivation function-deficient mutant and characterization of two independent p53 transactivation subdomains, Oncogene 18, 2405-2410.

Vinyals et al., (1999) A Failure of wild-type p53 gene therapy in human cancer cells expressing a mutant p53 protein, Gene therapy 6, 22-23

Waldman et al., (1997) Nat, Med., 3, 1034-1036

Wang Y, Prives C (1995) Increased and altered dna-binding of human p53 by s and G2/M but not G1 cyclin-dependent kinases. Nature 376, 88-91

Wieczorek, A., Waterman, J., Waterman, M., Halazonetis, T. (1996) Structure-based rescue of common tumor-derived p53 mutants, Nat. Med. 2, 1143-1146.

Waldman et al., (1997) Nat, Med., 3, 1034-1036

Wang Y, Prives C (1995) Increased and altered dna-binding of human p53 by s and G2/M but not G1 cyclin-dependent kinases. Nature 376, 88-91

Wieczorek, A., Waterman, J., Waterman, M., Halazonetis, T. (1996) Structure-based rescue of common tumor-derived p53 mutants, Nat. Med. 2, 1143-1146.

TABLE 1

Phenotypic consequence of co-expression of p53-V122A and another wild type or p53 mutant.

| | single mutant | | single mutant + V122A | |
|---|---|---|---|---|
| p53 alleles | growth* | color | growth | color |
| GAL1 promoter | | | | |
| control vector | ++++ | red | -- | N.A. |
| V122A | -- | N.A. | -- | N.A. |
| wild type | + | white | -- | N.A. |
| P151S | +++ | red | +/- | red |
| P152L | +++ | red | +/- | red |
| P177H | +++ | red | +/- | red |
| R213Stop | ++++ | red | -- | N.A. |
| S241F | +++ | red | +/- | red |
| C242Y | +++ | red | +/- | red |
| G279E | +++ | red | +/- | red |
| Q331Stop | +++ | red | -- | N.A. |
| ADH1 promoter | | | | |
| control vector | ++++ | red | -- | N.A. |
| V122A | -- | N.A. | -- | N.A. |
| wild type | ++++ | white | -- | N.A. |
| P177H | ++++ | red | +++ | red |
| G279E | ++++ | red | +++ | red |
| Q331Stop | ++++ | red | -- | N.A. |

*For the GAL1 promoter, growth was monitored on galactose plates; for the constitutive ADH1 promoter, growth was scored on glucose plates.

TABLE 2

Phenotypic consequence of overexpression of double mutant p53 containing the V122A and another mutation.

| P53 double mutant | growth* | color |
|---|---|---|
| GAL1 promoter** | | |
| V122A::Q331Stop | +++ | red |
| V122A::P177H | + | red |
| V122A::M246L | + | red |
| V122A::E258K | + | red |
| V122A::G279E | + | red |
| V122A::R282Q | +/- | red |
| control vector | ++++ | red |
| wild type p53 | + | white |
| V122A | - | N.A. |
| ADH1 promoter | | |
| V122A::Q331 Stop | ++++ | red |
| V122A::G279E | ++++ | red |
| V122A::P177H | ++++ | red |
| control vector | ++++ | red |
| wild type p53 | ++++ | white |
| V122A | - | N.A. |

*For the GAL1 promoter, growth was monitored on galactose plates; for the constitutive ADH1 promoter, growth was scored on glucose plates.
**All the single tumor mutants grew well on galatose

TABLE 3 p53 mutants that prevent growth[a] when expressed in yeast.

| Mutant | Codon change | Amino acid change | Structural location[b] | p53 tumor database[c] Del.-miss./identical change[d] |
|---|---|---|---|---|
| 2 | GTG > GCG | V122A | L1 | 2-0/0 |
| 3 | GCA > ACA | A76T | outside | 2-4/0 |
| | GTG > GCG | V122A | L1 | 2-0/0 |
| 4 | GTT > ATT | V274I | S10 | 5-37/2 |
| | TGT > TGG | C277W | S10-H2 | 3-43/0 |

TABLE 3-continued p53 mutants that prevent growth[a] when expressed in yeast.

| Mutant | Codon change | Amino acid change | Structural location[b] | p53 tumor database[c] Del.-miss./identical change[d] |
|---|---|---|---|---|
| 5 | TGT > CGT | C277R | S10-H2 | 3-43/0 |
|   | TTC > TTA | F338L | TD | 0-0/0 |
| 6 | GGG > AGG | G279R | H2 | 9-26/6 |

[a]Growth is prevented by expression of the mutant p53 from a GAL1 inducible promoter under conditions of galactose-induced high level expression or the lower level ADH1 constitutive expression. Microcolonies appeared after 4-5 days when the p53 mutant was under the ADH1 promoter, similar to what was observed with p53-V122A.
[b]Based on the crystal structure of the DNA binding domain (9). "Outside" indicates external to the DNA binding domain that has been examined.
[c]Based on the January 1999 release of the p53 tumor database that contains 10396 entries (44).
[d]Changes appearing in the p53 tumor database at the particular codon: "del" = deletions or frameshifts; "miss." = missense changes; "identical change" = number of tumor mutants in the p53 database that have the same amino acid substitution identified in the yeast assay.

TABLE 4

Phenotypic consequence of second site mutations in p53-V122A when over-expressed under the GAL1 promoter in yPH-p21 and yPH-bax.

| p53 double mutant | yPH-bax growth* | yPH-bax color | yPH-p21 growth* | yPH-p21 color |
|---|---|---|---|---|
| V122A::P177H | ++ | red | ++ | pink |
| V122A::M246L | ++ | red | ++ | pink |
| V122A::L252F | + | pink | + | white |
| V122A::E258K, | ++ | red | ++ | red |
| V122A::G279E | + | red | ++ | white |
| V122A::R282Q | +/– | white | +/– | white |
| V122A::Q331Stop | +++ | red | +++ | pink |
| control vector | +++ | red | +++ | red |
| wild type p53 | + | white | + | white |

TABLE 4-continued

Phenotypic consequence of second site mutations in p53-V122A when over-expressed under the GAL1 promoter in yPH-p21 and yPH-bax.

| p53 double mutant | yPH-bax growth* | yPH-bax color | yPH-p21 growth* | yPH-p21 color |
|---|---|---|---|---|
| V122A | – | N.A. | – | N.A. |
| V122A::H296R | – | N.A | – | N.A |

**All the single tumor mutants grew well and originated red colonies
N.A. = not assessable

TABLE 5

Summary of effects of various p53 mutations in yeast and human cells.

| | wt p53 | V122A | G279E | R28Q | V122A:: G279E | V122A:: R282Q |
|---|---|---|---|---|---|---|
| Response in human cells: | | | | | | |
| p21 induction | +++ | ++ | +/– | ++ | + | +/– |
| luciferase induction | ++ | ++ | – | +++ | ++ | +++ |
| growth* | ~10% | ~10% | ~70% | ~30% | ~25% | ~20% |
| Response in yeast (GAL1 promoter): | | | | | | |
| growth | + | – | ++ | + | + | +/– |
| lethality | NO | YES | NO | NO | No | No |
| Transcriptional activation | +++ | – | – | – | – | – |

*Growth corresponds to the number of stable transfectants obtained with the indicated p53 allele compared to vector control

TABLE 6 p53 alleles showing increased transcriptional activation compared to wild type p53 for RGC response element.

| Mutant | phenotype in pADH1 glucose | phenotype in pGAL1 raffinose | phenotype in pGAL1 galactose | amino acid change | Location[a] | p53 database[b] Del.-miss./ | identical change |
|---|---|---|---|---|---|---|---|
| w1 | white | white | no growth | TCT > CCT S96P | out | 0-1/ | 0 |
|    |       |       |           | CAT > CGT H115R | L1 | 0-2/ | 0 |
| w2a | white | white | no growth | TCT > TGT S121C | L1 | 1-0/ | 0 |
|     |       |       |           | T140T | | | |
| w3 | white | white | no growth | TCT > TTT S121F | L1 | 2-0/ | 0 |
| w4, w5 | white | white | no growth | ACT > GCT T123A | L1 | 0-0/ | 0 |
| w6 | white | white | no growth | TGC > TAC C124Y | L1 | 2-3/ | 0 |
| w7 | white | white | no growth | TGC > TTG C124F | L1 | 2-3/ | 5 |
|    |       |       |           | CAG > CGG Q167R | L2 | 13-12/ | |
|    |       |       |           | P309P | | | |
| w8 | white | white | no growth | GAG > AAG E171K | L2 | 16-7/ | 2 |
| w9 | white | white | no growth | CAC > TAC H178Y | H1 | 8-36/ | 6 |
| w10 | white | white | no growth | CAC > TAC H178Y | H1 | 8-36/ | 6 |
|     |       |       |           | TCA > TTA S183L | L2 | 6-2/ | 1 |
|     |       |       |           | T284T | | | |
| w11 | white | white | no growth | GAT > TAT D184Y | L2 | 5-8/ | 3 |
| w12 | white | white | no growth | ACC > ATC T231I | S8 | 1-9/ | 2 |
| w13 | white | white | no growth | ACC > ATC T231I | S8 | 1-9/ | 2 |
|     |       |       |           | H115H | | | |

TABLE 6-continued p53 alleles showing increased transcriptional activation compared to wild type p53 for RGC response element.

| Mutant | phenotype in pADH1 glucose | phenotype in pGAL1 raffinose | phenotype in pGAL1 galactose | amino acid change | Location[a] | p53 database[b] Del.-miss./ | identical change |
|---|---|---|---|---|---|---|---|
| w14 | no growth | white | no growth | CCT > CTT P191L | L2 | 19-13/ | 2 |
|  |  |  |  | AGT > AAT S240N | L3 | 5-24/ |  |
|  |  |  |  | S269S |  |  |  |
| w15, w16 | no growth | white | no growth | AGT > AAT S240N | L3 | 5-24/ | 0 |
| w2 | no growth | white | no growth | TCT > ACT S116T | L1 | 0-4/ | 0 |
|  |  |  |  | AAT > AAA N208K | after H2 | 4-9/ | 0 |
|  |  |  |  | TTC > CTC T378L | TD | 1-0/ | 0 |
| w17 | white | white | no growth | AGT > ACT S215T | S7 | 9-37/ | 2 |
|  |  |  |  | AAT > AAA N288K | after H2 | 4-9/ | 0 |
| p1 | white | pink | no growth | ACT > TCT T123S | L1 | 0-0/ | 0 |
|  |  |  |  | AAT > AGT N345S | TD | 1-0/ | 0 |
| p2 | white | pink | no growth | ACT > TGT T123S | L1 | 0-0/ | 0 |
| p3, p4 | white | pink | no growth | GAT > GGT D184G | L2 | 5-8/ | 1 |
| p5 | white | pink | no growth | GAA > GTA E198V | S5 | 14-6/ | 0 |
| p6a | white | pink | no growth | ACC > ATC T230I | S8 | 1-9/ | 5 |
| p6 | white | pink | no growth | GTT > GCT V274A | S10 | 6-45/ | 9 |

[a] according to the crystal structure of the DNA binding domain (Cho et al.,)
[a] jan 99 release: 10396 entries.
Del = deletions or frameshifts
miss. = missense changes reported at that codon.
Identical change = same amino acid substitution as found by the yeast assay.

TABLE 7

Transactivation with various responsive elements by supertrans p53 mutants at different levels of protein expression.

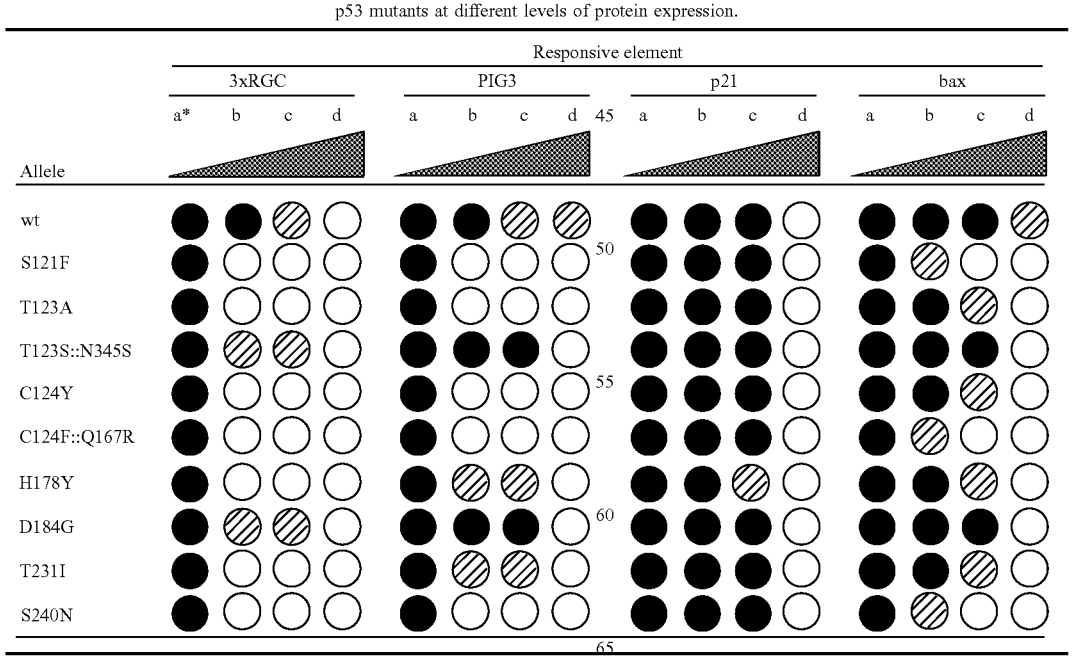

| Allele | 3xRGC a* | 3xRGC b | 3xRGC c | 3xRGC d | PIG3 a | PIG3 b | PIG3 c | PIG3 d | p21 a | p21 b | p21 c | p21 d | bax a | bax b | bax c | bax d |
|---|---|---|---|---|---|---|---|---|---|---|---|---|---|---|---|---|
| wt | ● | ● | ◍ | ○ | ● | ● | ◍ | ◍ | ● | ● | ● | ○ | ● | ● | ● | ◍ |
| S121F | ● | ○ | ○ | ○ | ● | ○ | ○ | ○ | ● | ● | ● | ○ | ● | ◍ | ○ | ○ |
| T123A | ● | ○ | ○ | ○ | ● | ○ | ○ | ○ | ● | ● | ● | ○ | ● | ● | ◍ | ○ |
| T123S::N345S | ● | ◍ | ◍ | ○ | ● | ● | ● | ○ | ● | ● | ● | ○ | ● | ● | ● | ○ |
| C124Y | ● | ○ | ○ | ○ | ● | ○ | ○ | ○ | ● | ● | ● | ○ | ● | ● | ◍ | ○ |
| C124F::Q167R | ● | ○ | ○ | ○ | ● | ○ | ○ | ○ | ● | ● | ● | ○ | ● | ◍ | ○ | ○ |
| H178Y | ● | ○ | ○ | ○ | ● | ◍ | ◍ | ○ | ● | ● | ◍ | ○ | ● | ● | ◍ | ○ |
| D184G | ● | ◍ | ◍ | ○ | ● | ● | ● | ○ | ● | ● | ● | ○ | ● | ● | ● | ○ |
| T231I | ● | ○ | ○ | ○ | ● | ◍ | ◍ | ○ | ● | ● | ● | ○ | ● | ● | ◍ | ○ |
| S240N | ● | ○ | ○ | ○ | ● | ○ | ○ | ○ | ● | ● | ● | ○ | ● | ◍ | ○ | ○ | a* = 2% glucose; b = 2% raffinose; c = 2% raffinose + 0.003% galactose; d = 2% raffinose + 0.015% galactose

TABLE 8 p53 supertrans alleles can overcome the dominant-negative effect of p53 tumor mutants for transactivation from the 3xRGC::ADE2 reporter

| | | | Allele 1 | | | | |
|---|---|---|---|---|---|---|---|
| | | | supertrans mutant | | | | |
| Allele 2 | no p53 | wild type | S121F | T123A | H178Y | S240N | V274A |
| no p53 | ● | ○ | ○ | ○ | ○ | no growth | ○ |
| wild type | ○ | ○ | ○ | ○ | ○ | no growth | ○ |
| tumor mutation | | | | | | | |
| P177H | ● | ⊘ | ○ | ○ | ⊘ | ○ | ○ |
| C242Y | ● | ⊘ | ○ | ○ | ⊘ | ○ | N.T. |
| G245D | ● | ⊘ | ○ | ○ | ⊘ | ○ | ○ |
| G279E | ● | ⊘ | ○ | ○ | ⊘ | ○ | N.T. |
| D281E | ● | ⊘ | ○ | ○ | N.T. | N.T. | N.T. |
| E286G | ● | ○ | ○ | ○ | N.T. | ○ | ○ |

○ = white colony    ◌ = white colony reduced growth
⊘ = pink colony    ● = red colony
N.T. = not tested
The yIG397 strain was transformed with the various p53 mutants under control of the ADH1 promoter

TABLE 9 p53 supertrans alleles can overcome the dominant-negative effect of p53 tumor mutants for transactivation from the bax::ADE2 reporter

| | | Allele 1 | | |
|---|---|---|---|---|
| | | | supertrans mutant | |
| Allele 2 | no p53 | wild type | S121F | T123A |
| no p53 | ● | ○ | ○ | ○ |
| wild type | ○ | ○ | ○ | ○ |
| tumor mutation | | | | |
| P177H | ● | ● | ○ | ○ |
| C242Y | ● | ● | ○ | ○ |
| G245D | ● | ● | ○ | ○ |
| G279E | ● | ● | ○ | ○ |
| D281N | ● | ● | ○ | ○ |

○ = white colony    ● = red colony
The yPH-bax strain was transformed with the various p53 mutants under control of the ADH1 promoter

TABLE 10 p53 alleles showing enhanced transcriptional activation compared to wild type p53 selected using the RGC or p21 or bax responsive elements.

| | phenotype in pADH1 | | phenotype in pGAL1 | | | p53 database[b] | identical |
|---|---|---|---|---|---|---|---|
| Mutant | glucose | raffinose | galactose | amino acid change | Location[a] | Del.-miss./ | change |
| Selected by 3xRGC::ADE2 reporter | | | | | | | |
| w19 | white | white | no growth | TGG > CGG W91R | out | 11-1/ | 0 |
| w20 | white | white | no growth | TCT > CCT S96P | out | 0-1/ | 0 |
| | | | | ATC > GTC I162V | S4 | 5-21/ | 3 |
| w21 | white | white | no growth | ATC > GTC I232V | S8 | 5-32/ | 2 |
| | | | | ACT > ATA T284I | H2 | 3-9/ | 0 |
| w22 | white | white | no growth | GCC > ACC A159T | S4 | 6-59/ | 5 |
| w23 | white | white | no growth | AAC > AGC N210S | S6-S7 | 4-6/ | 2 |
| Selected by p21::ADE2 reporter | | | | | | | |
| w24 | white | white | no growth | TGG > CGG W91R | out | 11-1/ | 0 |
| w25 | white | white | no growth | CTG > CGC L137R | S2'-S3 | 6-16/ | 0 |
| w26 | white | white | no growth | TCT > CCT S96P | out | 0-1/ | 0 |
| | | | | AAC > AGC N268S | S10 | 1-8/ | 5 |
| | | | | ACT > ATA T284I | H2 | 3-9/ | 0 |
| w27 | no growth | white | no growth | GAG > GCG E285A | H2 | 11-88/ | 0 |
| W28 | no growth | white | no growth | AAT > AAA N288K | H2 | 4-9/ | 0 |
| w29 | no growth | white | no growth | ACA > GCA T118A | L1 | 1-0/ | 0 |
| w30 | no growth | white | no growth | ACT > CCT T123P | L1 | 0-0/ | 0 |
| w31 | no growth | white | no growth | ATG > ACG M160T | S4 | 0-21/ | 0 |

TABLE 10-continued p53 alleles showing enhanced transcriptional activation compared to wild type p53 selected using the RGC or p21 or bax responsive elements.

| Mutant | phenotype in pADH1 glucose | phenotype in pGAL1 | | amino acid change | Location[a] | p53 database[b] Del.-miss./ | identical change |
|---|---|---|---|---|---|---|---|
| | | raffinose | galactose | | | | |

Selected by bax::ADE2 reporter

| Mutant | glucose | raffinose | galactose | amino acid change | Location | Del.-miss./ | change |
|---|---|---|---|---|---|---|---|
| w32 | no growth | white | no growth | AAC > TAC N239Y | L3 | 19-49/ | 4 |
| w33 | no growth | white | no growth | ACT > CCT T123P | L1 | 0-0/ | 0 |
| w34 | no growth | white | no growth | AGT > AAT S240N | L3 | 5-24/ | 0 |
| w35 | no growth | white | no growth | CCT > TCT P75S | out | 1-0/ | 0 |
| | | | | TAC > TTC Y107F | L1 | 4-0/ | 0 |

[a]Based on the crystal structure of the DNA binding domain (Cho et al., 1994). "Out" indicates external to the crystallized fragment

[b]Based on the April 1999 release of the p53 tumor database that contains 11110 entries (Hainaut et al., 1999).

Changes appearing in the p53 tumor database at the particular codon: "del" = deletions or frameshifts; "miss." = missense changes; "identical change" = number of tumor mutants in the p53 database that have the same amino acid substitution identified in the yeast assay.

TABLE 11

Summary of toxic and supertrans p53 mutants in yeast: (toxic p53's prevent growth at modest levels of induction)

| p53 allele | 3x RGC | PIG3 | bax | p21 | p53 position |
|---|---|---|---|---|---|
| wt | + | + | + | + | |
| W91R | +++ | | | | |
| H115R S96P | +++ | | | | L1 Loop |
| S116T N228K | +++ | | | | " |
| F338K | | | | | |
| T118A | | | | +++ | |
| S121F | +++ | +++ | +++ | + | " |
| S121C | +++ | +++ | + | + | " |
| V122A toxic | ≤+ | ≤+ | +++ | +++ | " |
| T123A | +++ | +++ | + | + | " |
| T123S N345S | +++ | +++ | ++ | + | |
| T123S | ++ | + | + | + | " |
| T123P | +++ | | +++ | ++ | " |
| C124Y | +++ | +++ | + | + | " |
| C124F Q167R | +++ | + | + | + | " |
| L137R | +++ | ++ | +++ | +++ | S2 |
| A159T | +++ | | | | |
| M160T | +++ | ++ | +++ | +++ | S4 |
| I162V | +++ | | | | S4 |
| Q167R | +++ | | | | L2 Loop |
| E171K | +++ | | | | L2 Loop |
| H178Y tumor | +++ | ++ | + | + | H1 |
| H178Y S183L | +++ | | | | L2 Loop |
| D184Y | +++ | | | | L2 ZN |
| D184G | ++ | + | + | + | " |
| E198V | ++ | | | | " |
| N210S | +++ | | | | S6-S7 |
| S215T N288K | +++ | | | | S7, >H2 |
| N288K | | | +++ | | H2 |
| T230I | +++ | | | | S8 |
| T231I | +++ | ++ | + | + | S8 |
| I232V | +++ | | | | S8 |
| N239Y | | +++ | | | L3 |
| S240N | +++ | +++ | +++ | + | L3 |
| S240N P191L | +++ | | | | |
| N268S | +++ | +++ | + | +++ | S10 |
| V274A | +++ | | + | | " |
| ts 37C | | | | | |
| C277R toxic | ≤+ | ≤+ | ≤+ | +++ | Helix2 |
| C277W toxic | ≤+ | ≤+ | ≤+ | +++ | " |
| G279R toxic | ≤+ | ≤+ | ≤+ | + | " |
| E285A | ++ | ++ | +++ | +++ | " |
| A76 T V122A | | | | | |
| A76 influence | | | | | |
| V122A toxic effects | | | | | |
| F338L (may affect tetramer stability) | | | | | |
| C124R, Q136K T150A multiple mutant is toxic | | | | | |
| T150A may contribute to toxicity | | | | | |

TABLE 12

Similarity of responses in yeast and SAOS2 cells of p53 mutants:
CHARACTERIZATION IN HUMAN SAOS2 CELLS
OF HIGHLY EXPRESSED P53 MUTANTS GENERATED IN YEAST

| | | | Transactivation | | | | |
|---|---|---|---|---|---|---|---|
| | | | From reporter ## | | | | |
| p53 allele$^\Sigma$ | yeast or mammal | growth inhibition | MDM2 Saos2 only | RGC* 3X in yeast 13 X in SAOS2 | BAX Same oligo in yeast and Saos2 | p21** oligo in yeast and complete in Saos2 | From endogenous p21 |
| wt | yeast | + | | + | + | + | |
| | mammal.. | + | + | + | + | + | + |
| G279$^\Sigma$ (tumor) | yeast | − | | − | − | − | |
| | mamm | − | − | − | − | − | − |
| V122A toxic | yeast | +++ | | − | ++ | +++ | |
| | mammal | + | + | + | ++ | + | + |
| V122A:: G279E | yeast | + | | − | − | + | |
| | mammal | +/− | + | + | − | +/− | +/− |
| R282Q$^\Sigma$ tumor | yeast | +/− | | − | − | + | |
| | mammal | +/− | | + | | + | +/− |
| V122A:: R282Q | yeast | + | | − | − | + | |
| | mammal | +/− | + | + | | + | +/− |
| T123A supertrans | yeast | ++ | | +++ | ++ | + | |
| | mammal | + | ++ | | +/− | ++ | + |
| C124Y | yeast | ++ | | +++ | + | + | |
| | mammal | ++ | ++ | | +/− | + | + |
| S240N | yeast | +++ | | +++ | ++ | + | |
| | mammal | ++ | ++ | | ++ | +/− | + |
| S121F | yeast | ++ | | +++ | + | + | |
| | mammal | ++ | − | +/− | − | − | +/− |
| V274A#$^\Sigma$ (ts at 37) | yeast | ++ | | +++ | + | + | |
| | mammal | − | − | − | − | − | − |

$^\Sigma$previously identified
**p21--5' response element in yeast. In human cells, the complete 2.4 kb promoter

TABLE 13

Similarity of responses in yeast and SAOS2 cells of mouse p53 mutants:
CHARACTERIZATION IN HUMAN SAOS2 CELLS
OF HIGHLY EXPRESSED P53 MUTANTS ISOLATE FROM MOUSE TUMORS

| | | | Transactivation | | | | |
|---|---|---|---|---|---|---|---|
| | | | From reporter ## | | | | |
| p53 allele$^\Sigma$ | yeast or mammal | growth inhibition | MDM2 Saos2 only | RGC* 3X in yeast 13 X in SAOS2 | BAX Same oligo in yeast and Saos2 | p21** oligo in yeast and complete in Saos2 | From endogenous p21 |
| wt mouse | yeast | + | | + | + | + | |
| | mammal.. | + | + | + | + | + | + |
| mouse T122L^ | yeast | +++ | | − | ++ | ++ | |
| | mammal | − | +/− | +/− | + | + | +/−− |
| mouse R270C^ | yeast | − | | − | − | − | |
| | mammal | − | − | − | − | − | − |

$^\Sigma$previously identified
**p21--5' response element in yeast. In human cells, the complete 2.4 kb promoter
Integrated in yeast and on plasmid in Saos2
Additional notes:
Transactivation in yeast used the ADE2 reporter, in mammalian it was luciferase on a reporter plasmid or using antibody to p21 expressed from the endogenous reporter.

The invention claimed is:

1. An isolated human p53 polypeptide containing the mutation V122A introduced into the wild-type human p53 molecule.

2. An isolated nucleic acid encoding the polypeptide of claim 1.

* * * * *

SEQUENCE LISTING

<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 1
gaccttgcct ggacttgcct ggccttgcct                                         30

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 2
gaacatgtcc caacatgttg                                                    20

<210> SEQ ID NO 3
<211> LENGTH: 37
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 3
tcacaagtta gagacaagcc tgggcgtggg ctatatt                                 37

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 4
agcttgccca cccatgctcc agcttgccca cccatgctc                               39